United States Patent [19]

Toyama

[11] Patent Number: 5,412,203

[45] Date of Patent: May 2, 1995

[54] CYLINDRICAL CONTAINER INNER SURFACE TESTER

[75] Inventor: Kouichi Toyama, Kawasaki, Japan

[73] Assignee: Fuji Electric Co., Ltd., Japan

[21] Appl. No.: 157,908

[22] Filed: Nov. 24, 1993

Related U.S. Application Data

[63] Continuation-in-part of Ser. No. 914,332, Jul. 15, 1992, Pat. No. 5,233,199, and Ser. No. 970,280, Nov. 2, 1992, Pat. No. 5,338,000.

[30] Foreign Application Priority Data

| Jul. 15, 1991 | [JP] | Japan | 3-172940 |
| Sep. 12, 1991 | [JP] | Japan | 3-232093 |
| Sep. 30, 1991 | [JP] | Japan | 3-249946 |
| Oct. 15, 1991 | [JP] | Japan | 3-265134 |
| Nov. 1, 1991 | [JP] | Japan | 4-286934 |
| Nov. 25, 1992 | [JP] | Japan | 4-313827 |

[51] Int. Cl.⁶ .................................. G01N 9/04
[52] U.S. Cl. ....................... 250/223 B; 209/526
[58] Field of Search ............ 250/559, 223 B, 223 R; 209/524, 526; 382/8

[56] References Cited

U.S. PATENT DOCUMENTS

| 4,513,316 | 4/1985 | Kobayashi et al. | |
| 4,580,045 | 4/1986 | Kulig | 250/223 B |
| 4,948,956 | 8/1990 | Fukuchi | 250/223 B |
| 5,072,107 | 12/1991 | Apter | 250/223 B |

FOREIGN PATENT DOCUMENTS

| 0362679 | 4/1990 | European Pat. Off. |
| 0491663 | 6/1992 | European Pat. Off. |
| 2171640 | 7/1990 | Japan. |

*Primary Examiner*—David C. Nelms
*Assistant Examiner*—K. Shami
*Attorney, Agent, or Firm*—Greer, Burns, Crain, Ltd.

[57] ABSTRACT

A cylindrical container inner surface tester which illuminates an opening of a test container. The test container is located at a predetermined position with its opening set levelly to capture the opening through a TV camera. The tester also detects black and white spots on the inner surface of the cylindrical container. This is accomplished by analyzing an image obtained by the TV camera using defect detecting means. The tester includes a frame memory which stores a multi-value continuous tone image signal as image data. The image signal is obtained by A/D-converting from a continuous tone image signal obtained by scanning the captured image. The tester also includes an area detecting unit which generates a binary image signal by binary-converting from a multi-value continuous tone image signal read by horizontally or vertically scanning the frame memory. This is accomplished using a predetermined threshold. The area detecting unit is also used to determine a test area. The test area falls within the area between the first rise point and the last fall point of each scanning line of the controlled binary image signal.

9 Claims, 47 Drawing Sheets

PB
LEFT ADJACENT POINT

PA
RIGHT ADJACENT POINT

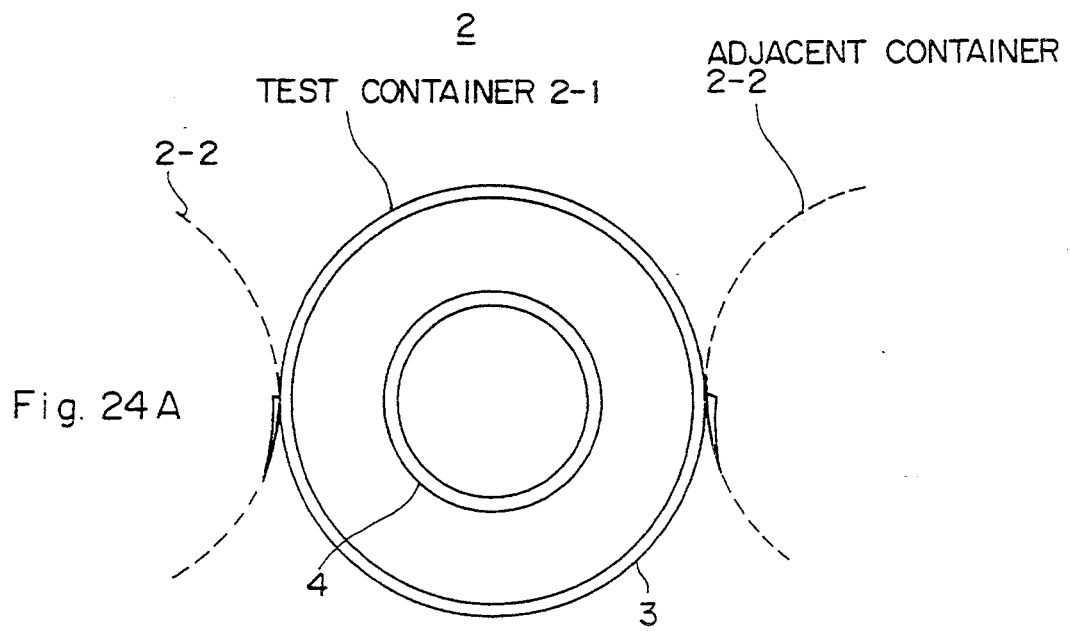
Fig. 24A
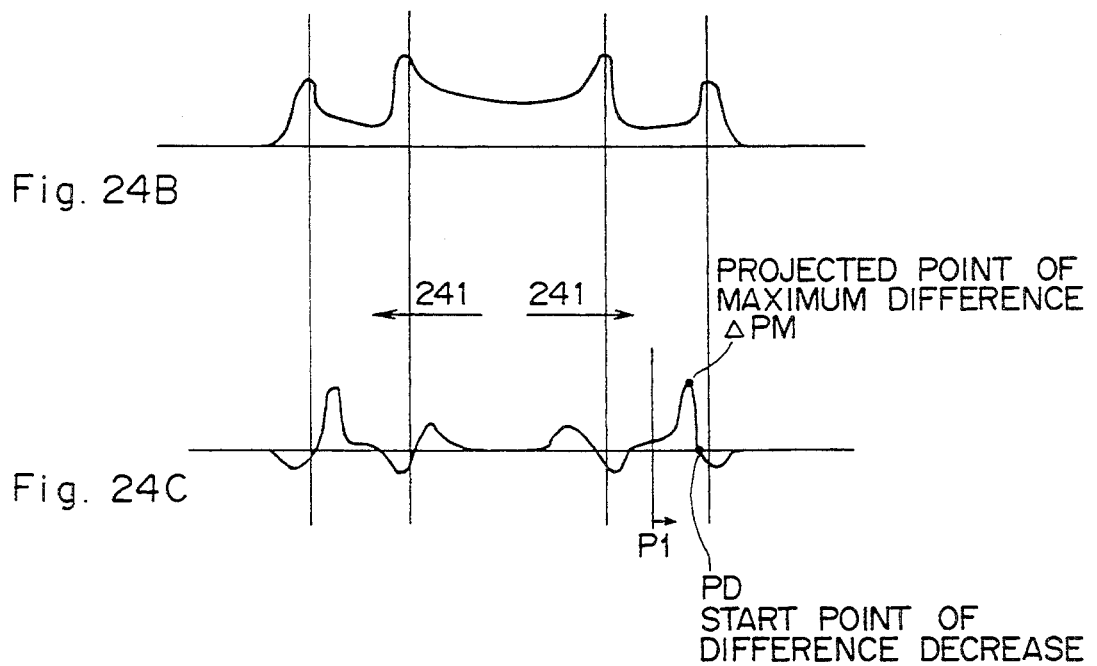
Fig. 24B
Fig. 24C

CYLINDRICAL CONTAINER INNER SURFACE TESTER

CROSS REFERENCE TO RELATED APPLICATION

This application is a continuation-in-part application of both U.S. patent application Ser. No. 07/914,332 filed on Jul. 15, 1992, now U.S. Pat. No. 5,233,199, and U.S. patent application Ser. No. 07/970,280 filed on Nov. 2, 1992, now U.S. Pat. No. 5,338,000.

BACKGROUND OF THE INVENTION

1. Field of the Invention

The present invention relates to an image processing device, and more specifically to a cylindrical container inner surface tester for checking the inner surface of a cylindrical container having a joint in the side of a beer can with metal luster, a paper cup, etc. to be carried on a conveyor, and for detecting foreign substances, dust, scratches, etc. on the surface.

2. Description of the Prior Art

FIGS. 1A and 1B are views for explaining a highlighted portion of a sample aluminum beer can when observed from above. FIG. 1A is a top view (image) of the container (can) and FIG. 1B is its sectional view. 2 is a container; 1 is a ring illumination for illuminating the container 2 from above; 3 is a highlighted portion at the opening of the container; and 4 is a valley highlighted portion. Thus, the portions 3 and 4 are highlighted at the opening and the bottom of the container. They are specifically highlighted if the container has metallic raster inside.

FIGS. 2A and 2B show intensity variations represented by the scanning line Q - Q1 on the top view of the container 2. The intensity variations can be classified into 5 level area from W1 to W5. First area W1 refers to the highlighted opening portion 3; second area W2 refers to the internal upper middle part of the container indicating comparatively high intensity; third area W3 refers to the internal lower middle part of the container subject to less amount of light of the illumination 1 shown in FIG. 1A indicating intensity lower than other portion of the container; fourth area W4 refers to the highlighted portion of the bottom; and fifth area W5 refers to the inner bottom of the container.

Conventionally, these areas W1-W5 are provided with a window individually and assigned thresholds used for detecting defects such as blacks spots (black points) and white spots (white points) according to the optical characteristics of each area. One method of detecting a defect is, for example, to convert by a predetermined threshold a multi-value continuous tone image signal of 8 bits, etc. to a binary value. The signal is obtained by A/D-converting an analog video signal (analog continuous tone image signal) obtained by scanning a target image. Another method is a differentiation method in which the above-described video signal is differentiated through a differentiation circuit as shown in FIG. 3 to extract a defect signal. In the differentiation method, a differentiation signal can be obtained for the contour of a test object. While either of a positive pulse or a negative pulse is generated by the differentiation along the contour of a test object, these pulses are generated simultaneously at a fine defective point, thereby extracting a defect.

That is, if the following expressions exist between the a value $P(i,j)$ and values $P(i-\alpha, j)$ and $P(i+\beta, j)$, where $P(i,j)$ indicates a target point (coordinates $x=i$ and $y=j$) referred to by a signal $P(x,y)$ obtained by differentiating an analog continuous tone image signal generated by a raster scanning operation, and $P(i-\alpha, j)$ and $P(i+\beta, j)$ indicate the points $\alpha$ picture elements forward and $\beta$ picture elements backward of the above-described point $P(i,j)$ in the x direction of the scanning line.

$$P(i,j) - P(i-\alpha, j) > TH1 \text{ and}$$

$$P(i+\beta, j) - P(i,j) > TH1$$

where TH1 indicates a predetermined threshold (positive value).

A binary function values $PD(i,j)=1$ and $PD(i,j)=0$ are defined for detecting a defect on a target point and respectively indicate an abnormal black point and a normal point.

However, in the above-described defect detecting method, an optimum value of a threshold TH1 to be determined by optical characteristics of a container's inner surface is subject to change. Accordingly, in the conventional method, a number of concentric circle windows are necessary as shown by windows W1-W5 in FIG. 2B (five windows in this case). Simultaneously, these windows must be assigned different thresholds TH1 (and coordinates $\alpha, \beta$). Thus, much time is wasted during the raster scanning operation, thereby offering a bottleneck to a high speed defect detection.

FIGS. 4A to 4C are views for explaining the problem in the conventional defect detecting method based on the differentiation method. FIG. 4A shows an example of intensity variations (analog continuous tone image signal) represented by the scanning line Q-Q1; FIG. 4B shows an example of an analog differentiation signal shown in FIG. 4A; and FIG. 4C shows an example of a digital differentiation signal shown in FIG. 4A. The portions indicated by BDs shown in FIGS. 4A-4C refer to black spots. That is, there are following problems in the conventional defect detecting method in which a black level defect BD is extracted by a signal in the area having intensity variations as shown in FIG. 4A. In the analog differentiation method, a differentiation signal indicating a small defective point is superposed on a basic intensity differentiation signal according to a time constant of a filter circuit as shown in FIG. 4B. In the digital differentiation method, a signal indicates unstable values as shown in FIG. 4C, and a differentiation signal indicating a defective point is embedded in noise components, thereby getting in difficulties in detecting a defect signal according to a predetermined threshold.

FIG. 5A is a sample top view of a container 2 having a projecting portion $2a$ which often generates highlighted portions 4-1, 4-2, etc. in series according to the form of the container's bottom or the variations in the reflection of a light off the side of the container. Specifically, most metallic containers have a mirror like inner surface and cause the above described problems.

Such highlighted portions can be hardly removed only by appropriately using an illumination. Therefore, the conventional defect detecting method has, in vain, to solve the above described uneven illumination generated as a highlighted portion inside a test container in testing its inner surface.

The first object of the present invention is to provide a cylindrical container's inner surface tester for detecting a defective portion stably and precisely even though there is uneven illumination inside a test container.

FIG. 6A shows a paper cup 5, that is, a typical cylindrical container, and the sectional view of a ring illumination 1 provided above the paper cup 5. FIG. 6B shows an example of an image (image data stored in a frame memory of the tester) obtained by capturing the inner surface of the paper cup 5 from above the paper cup 5 by a wide-angle-lens camera not shown in FIG. 6A. As shown in FIG. 6B, a joint 6 is detected in the side of the cup in the image. The joint 6 can be considered to be a generally straight line. However, since the opening of the paper cup 5 is formed as a curled rim for reinforcement, a top-end joint 7 is not in the line of the joint 6, indicating irregularity. Furthermore, since a normal cylindrical container can rotate at any angle while it is carried on a conveyor, the position of the joint 6 in the side of the container cannot be specified in a test image.

Assume that a spot 8 exists around the top-end joint 7 indicating the irregularity at the end of the straight line. Conventionally, the joint 6 is considered to be a straight line, and a multi-value continuous tone image signal (image data) read from a frame memory is converted to a binary value according to a predetermined threshold to generate a binary image signal. Then, the coordinate of each point of picture elements forming the joint can be determined by scanning the binary image signal and storing the coordinate indicating a change in binary image signals. Next, it is determined whether or not each point is in the joint. If a coordinate is obtained as being in the straight line, then it indicates that the point is in the joint. Then, an image indicating a spot is detected around the joint. For example, a regression line is obtained from the coordinate of each change point; the distance from the regression line to each of the above described coordinates is obtained; and all distance values are added up. An image indicating a spot around the joint 6 can be determined by checking the sum whether or not it is equal to or smaller than a predetermined threshold.

However, the top-end joint 7 detected at the curled rim indicates irregular data compared with the joint 6, and is not in the joint 6 according to the above described conventional method of detecting a picture element indicating a spot. Therefore, if the top-end joint 7 is included in the determination, the difference between the top-end joint 7 and an approximated line of the joint 6 is accumulated as an error when the above described sum is obtained, thereby lowering the precision of a test around the joint 6. Accordingly, the deterioration in precision cannot be prevented if the joint 6 and the top-end joint 7 are tested as being processed in the same test area. Thus, it is necessary to process each of the joint 3 and the top-end joint 7 in a separate test area. Since the cylindrical container (paper cup 5) freely rotates as described above, the position of the joint 6 is calculated according to a binary image signal generated for each test image. According to the result, the position of the top-end joint 7 can be determined.

A method of processing the top-end joint 7 in a separate area can be to detect a picture element indicating a spot by specifying the area between a broken line 9 and the circumference of the container as an independent test area according to an outline detecting method and performing a binary conversion using an appropriate threshold. However, according to this method, a test area specified as the area around the top-end joint 7 is exceedingly large, thereby taking a long time in performing an arithmetic operation to test a single paper cup 5. As a result, the test cannot be practically carried out at a container production speed.

As described above, an efficient method of testing the area around the top-end joint 7 by limiting it to a small area has been required, but has not been developed yet. The second object of the present invention is to provide a cylindrical container inner surface tester for practically testing a picture element indicating a spot around the top-end joint 7 at a high speed enough to perform a test at a production speed and with high precision.

SUMMARY OF THE INVENTION

The present invention relates to a cylindrical container inner surface tester for determining a spot on the inner surface of the side of an axis-symmetrical cylindrical container of a predetermined form having a linear joint in its side surface, by illuminating the inside of the cylindrical container from above, capturing through a TV camera the illuminated surface of the cylindrical container from above in the axis direction of the cylindrical container, and analyzing the captured image.

To solve the above described first problem, the cylindrical container's inner surface tester illuminates from above in the axis direction of a container the inner surface of an axis-symmetrical cylindrical container. A TV camera captures the illuminated area of the cylindrical container from above in the axis direction. Then, the captured image is analyzed to determine a black or white spot inside the cylindrical container.

The cylindrical container's inside surface tester comprises a frame memory for storing as image data corresponding to the captured image a multi-value tone continuous image signal (PO, etc.), that is, an A/D conversion signal of a continuous tone image signal obtained by scanning the captured image; and an area detecting unit (area detecting circuit) for generating a binary image signal by converting with a predetermined threshold (THG, etc.) into a binary value a multi-value continuous tone image signal read by a horizontal or vertical scanning of the frame memory, and for determining a test target area from the first rise point to the last fall point of the binary image signal in each scanning process.

The cylindrical container inner surface tester further comprises a window gate circuit for masking with predetermined masking pattern data an area having different optical properties in a test target area detected by the area detecting unit with, for example, a mask rise point 63 and a mask fall point 64.

A target picture element value and two background picture element values are extracted. The target picture element value (coordinates x=i and y=j) at a target point PO(i,j) are associated with a multi-value continuous tone image signal PO(x,y) based on the raster scanning operation. The background picture element values of two background points PO(i+α, j) and PO(i−α, j) indicate the value of the points each picture elements forward and backward of the above described point PO(i,j) in the x direction of the scanning line are extracted. Then, the intensity relationship where the relationship among these three points indicates a valley when detected as a black level while it indicates a peak when detected as a white level is detected (that is, the difference in intensity between a background picture element value and a target picture element value is detected). The target picture element value PO(i,j) is determined to be a defective picture element when the absolute value indicating the difference in the intensity exceeds a predetermined threshold THD.

FIGS. 7A and 7B show the principle of the valley-detection binary-conversion method which is the most important point in the present invention. FIG. 7A shows an example of a multi-value continuous tone image signal PO(x,y) in the scanning line Q-Q1 (y=j).

However, the multi-value continuous tone image signal PO is read by scanning a frame memory, and is extracted as a signal for a portion, of a fixed binary-conversion signal corresponding to the signal PO, within a test target area from the first rise point to the last fall point.

11 is a target point in a non-defective portion; and 12 and 13 are forward background point and backward background point of a non-defective portion respectively picture elements forward and backward of the target point 11 in the scanning line.

Likewise, 14 is a target point in a defective portion; and 15 and 16 are forward background point and backward background point of a non-defective portion respectively picture elements forward and backward of the target point 11 in the scanning line.

If the following expressions exist when the coordinates of a target point are (i,j) (that is, x=i and y=j), a binary function value POD(i,j)(referred to as a binary defective peak/valley image signal) for detecting a defect on a target point equals 1, and the target point is determined to be a valley (defect).

$$PO(i-a, j) - PO(i,j) > THD \qquad (1) \text{ and}$$

$$PO(i+a, j) - PO(i,j) > THD \qquad (2)$$

where THD indicates a predetermined threshold (positive value).

The non-defective portion shown in FIG. 7A does not apply to the above described expression (2), and no defects are detected. However, expressions (1) and (2) exist in the defective portion shown in FIG. 7A and a valley defect is detected. FIG. 7B shows the above described peak/valley binary image signal POD (x,j) as an output of defect determination.

Thus, an optimum detecting performance can be realized by dividing the waveform shown in FIG. 7A into a plurality of small areas and appropriately assigning to each of the small areas a threshold THD and the number $a$ of picture elements indicated in expressions (1) and (2) above.

When a peak (defect) is detected by the present invention, the target point is determined to be a defective peak having the peak/valley binary image signal POD-(i,j)=i if the following expressions exist where the position of the difference paragraph in each of the above described expressions (1) and (2) is exchanged with the other paragraph as follows.

$$PO(i,j) - PO(i-a, j) > THD \qquad (1A) \text{ and}$$

$$PO(i,j) - PO(i+a, j) > THD \qquad (2A)$$

The cylindrical container's inner surface tester illuminates from above in the axis direction of a container by a ring illumination 1 the inner surface of an axis-symmetrical cylindrical container. A TV camera captures the illuminated area of the cylindrical container from above in the axis direction. Then, the captured image is analyzed to determine a spot or deformation inside the cylindrical container.

The image of the inner surface of the cylindrical container is scanned along a concentric circle or spiral scanning line (hereinafter referred to as a circular scanning line) which is centered on the center of the image and varies sequentially per cycle of a radius varying every one or more picture elements predetermined. Then, the absolute value indicating the difference between the intensity of the target picture elements among a plurality of picture elements arranged at intervals such that one or more picture elements are arranged between two target picture elements and the intensity of background picture element predetermined number of a plurality of picture elements forward or backward of the target picture element is compared with a threshold predetermined according to the position of the circular scanning line. The above described processes are repeated for each target picture element, and a defect detecting unit determines a defective container inner surface when an absolute value larger than the value of the difference between the above described intensity values is detected.

The above mentioned threshold must be set as the optimum threshold per circle of the circular scanning line.

The intensity of the background picture element refers to an average intensity value among the picture elements in a predetermined one-dimensional or two-dimensional local area centered on the background picture element.

The tester according to the present invention illuminates from above in the axis direction of a container the inner surface of an axis-symmetrical cylindrical container using a ring-shaped illuminator. When a TV camera captures the illuminated area of the cylindrical container from above in the axis direction and the captured image is analyzed, the distribution of the continuous tone on the container inner surface is concentrically generated. Taking this into account, a picture element string is obtained by scanning the container inner surface along the ring or spiral circular scanning line. When a defective concave exists, it appears as a continuous tone in the scanned picture element string. Thus, the absolute value $\Delta P$ indicating the difference between the intensity P0 of the target picture elements in a scanned picture element string and the intensity P1 of the background picture element d picture elements forward or backward of the target picture element is calculated by the following equation.

$$\Delta P = \| P_0 - P_1 \|$$

A threshold THP is assigned to each of the windows W1 through W5 shown in FIG. 2B, and the threshold THP is compared with the absolute value P indicating the difference between the intensity values. If P is larger than the THP, the target picture element is determined to be a picture element of a defective inner surface such as a concave, etc.

However, the threshold THP can be set per circle of the circular scanning line, for example, according to its position. The intensity P1 of the background picture element can be an average intensity value among picture elements in a one-dimensional local area (that is, a series of n picture elements on the scanning line) or a two-dimensional local area (that is, a local area comprising n picture elements by n picture elements.

To solve the second problem, the cylindrical container inner surface tester according to the present invention comprises a frame memory for storing a multi-value continuous tone image signal obtained by A/D-converting a continuous tone image signal obtained by scanning the captured image; an area specifying circuit for generating a ring-shaped window pattern such that the image of the joint in the side of the container is included in the pattern; a change point storage circuit for converting to a binary value according to a predetermined threshold a multi-value continuous tone image signal read by a horizontal or vertical scanning operation from an area specified by a ring-shaped window pattern generated by the area specifying circuit, and for storing for each scanning operation the coordinate of a signal change point of a binary image signal generated by the converting process; a position determining circuit for determining the position of a line similar to the joint in the side surface of the container according to the coordinate of a signal change point stored in the change point storing circuit; an intersection calculating circuit for calculating the coordinate of an intersection between a line determined by the position determining circuit and the ring-shaped window pattern; a reference coordinate determining circuit for determining a generation reference coordinate of a subwindow by adding a predetermined offset value to the intersection coordinate obtained by the intersection calculating circuit; and a target area extracting circuit for generating a subwindow of a predetermined form according to the generation reference coordinate of a subwindow determined by the reference coordinate determining circuit, and for determining as a test target area to be searched for a spot an image area, in the frame memory, corresponding to the area of the subwindow.

The cylindrical container inner surface tester according to the present invention can also be designed as further comprising a binary image signal generating circuit for generating a binary image signal by converting to a binary value a multi-value continuous tone image signal in the sub-window according to a predetermined threshold for use in detecting the background of the cylindrical container, wherein the target area extracting circuit determines as a test target area to be searched for a spot an image area, in the frame memory, corresponding to the area obtained by excluding the background of the cylindrical container from the sub-window area.

The present invention can be applicable as a cylindrical container inner surface tester for determining a spot on the inner surface of the side of a cylindrical container of a predetermined form having a linear joint in its side surface, by capturing through a TV camera the illuminated surface of the cylindrical container obliquely from above in the axis direction of the cylindrical container, and by analyzing the captured image.

In the present invention, the cylindrical container inner surface tester according to the present invention comprises a frame memory for storing a multi-value continuous tone image signal obtained by A/D-converting a continuous tone image signal obtained by scanning the captured image; a fixed area specifying circuit for generating a fixed window pattern such that the image of the joint in the side of the container is included in the pattern; a change point storage circuit for converting to a binary value according to a predetermined threshold a multi-value continuous tone image signal read by a horizontal or vertical scanning operation from an area specified by a fixed window pattern generated by the fixed area specifying circuit, and for storing for each scanning operation the coordinate of a signal change the point of a binary image signal generated by the converting process; a position determining circuit for determining the position of a line similar to the joint in the side surface of the container according to the coordinate of a signal change point stored in the change point storing circuit; an intersection calculating circuit for calculating the coordinate of an intersection between a line determined by the position determining circuit and the ring-shaped window pattern; a reference coordinate determining circuit for determining a generation reference coordinate of a subwindow by adding a predetermined offset value to the intersection coordinate obtained by the intersection calculating circuit; and a target area extracting circuit for generating a subwindow of a predetermined form according to the generation reference coordinate of a subwindow determined by the reference coordinate determining circuit, and for determining as a test target area to be searched for a spot an image area, in the frame memory, corresponding to the area of the subwindow.

The cylindrical container inner surface tester according to the present invention can also be designed as further comprising a binary image signal generating circuit for generating a binary image signal by converting to a binary value a multi-value continuous tone image signal in the sub-window according to a predetermined threshold for use in detecting the background of the cylindrical container, wherein the target area extracting circuit determines as a test target area to be searched for a spot an image area, in the frame memory, corresponding to the area obtained by excluding the background of the cylindrical container from the sub-window area.

The present invention can be applicable as a cylindrical container inner surface tester for determining a spot on the inner surface of the side of a cylindrical container of a predetermined form having a linear joint in its side surface, by capturing through a TV camera the illuminated surface of the cylindrical container obliquely from above in the axis direction of the cylindrical container, and by analyzing the captured image.

BRIEF DESCRIPTION OF THE DRAWINGS

One skilled in the art can easily understand additional features and objects of this invention from the description of the preferred embodiments and some of the attached drawings. In the drawings:

FIGS. 24A to 24C show how to detect an adjacent point according to the present invention;

DESCRIPTION OF THE PREFERRED EMBODIMENT

Figure 4A:
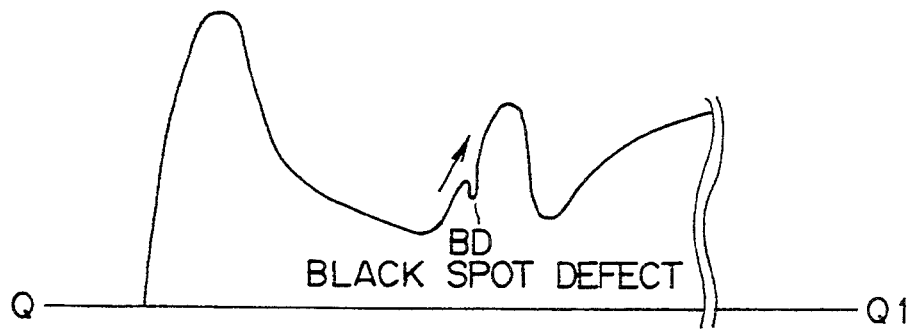
FIGS. 4A to 4C show the conventional method of detecting a defect.
Figure 4B:
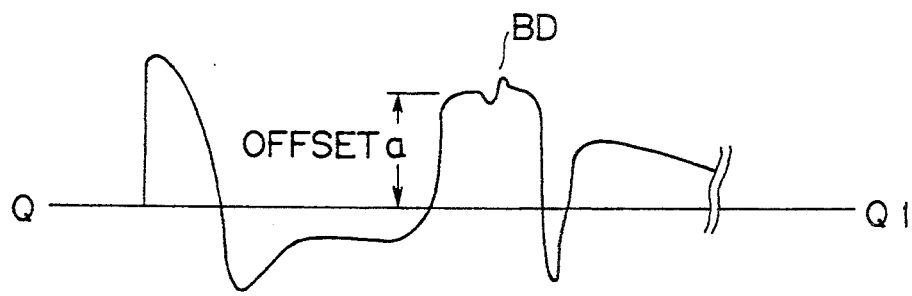
Figure 4C:
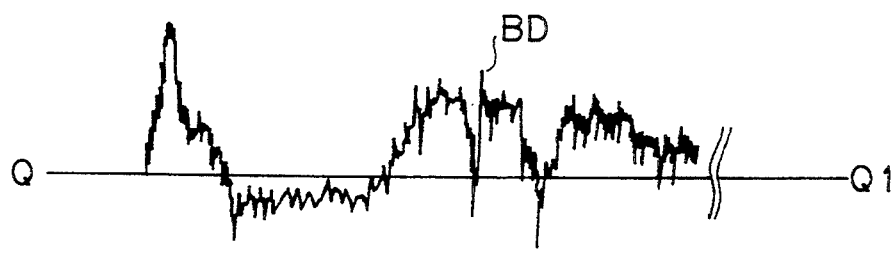

FIGS. 4A to 4C are views for explaining the problem in the conventional defect detecting method based on the differentiation method. FIG. 4A shows an example of intensity variations (analog continuous tone image signal) represented by the scanning line Q-Q1; FIG. 4B shows an example of an analog differentiation signal shown in FIG. 4A; and FIG. 4C shows an example of a digital differentiation signal shown in FIG. 4A. The portions indicated by BDs shown in FIGS. 4A-4C refer to black spots. That is, there are following problems in the conventional defect detecting method in which a black level defect BD is extracted by a signal in the area having intensity variations as shown in FIG. 4A. In the analog differentiation method, a differentiation signal indicating a small defective point is superposed on a basic intensity differentiation signal according to a time constant of a filter circuit as shown in FIG. 4B. In the digital differentiation method, a signal indicates unstable values as shown in FIG. 4C, and a differentiation signal indicating a defective point is embedded in noise components, thereby getting in difficulties in detecting a defect signal according to a predetermined threshold.

Figure 5A:
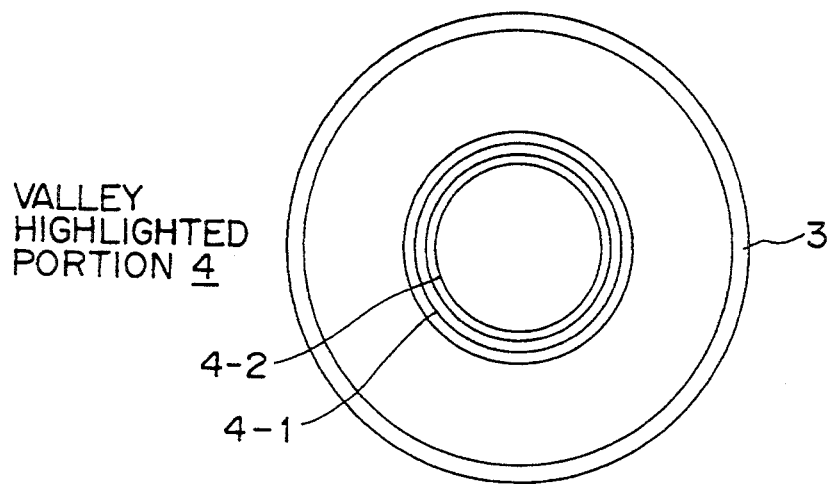
FIGS. 5A and 5B show the highlighted portion inside a container having an unusual valley shape.
Figure 5B:
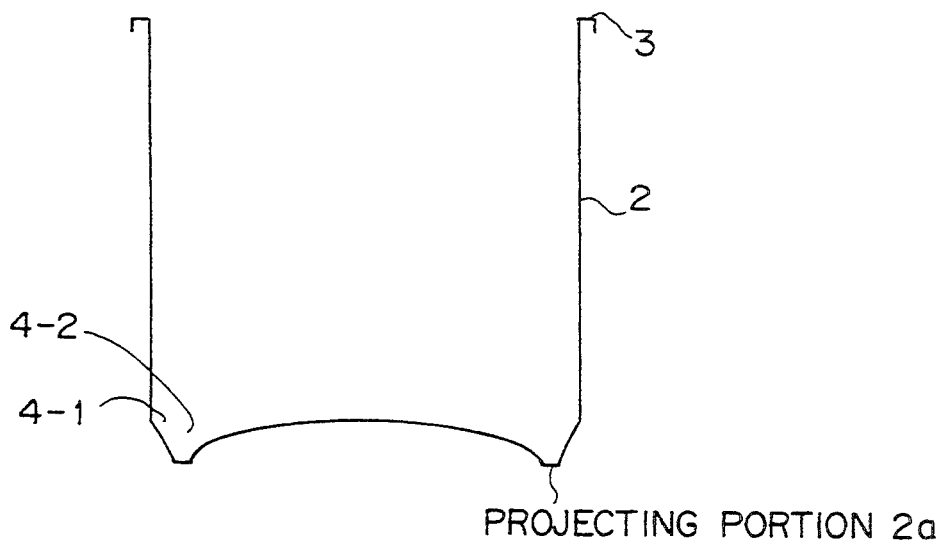
Figure 6A:
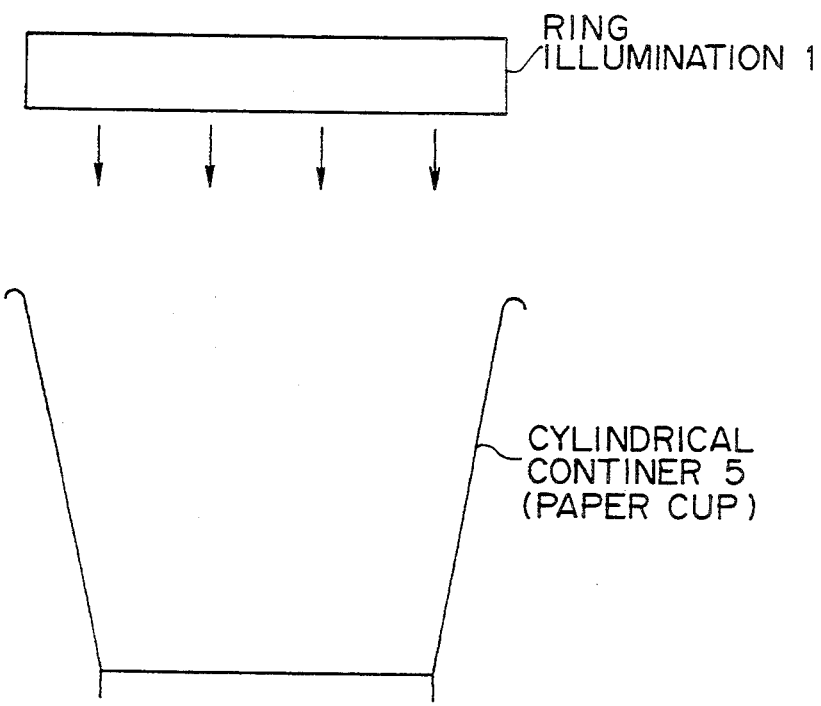
FIGS. 6A and 6B show an example of an image obtained by capturing a cylindrical container using an illuminator in a connection method.
Figure 6B:
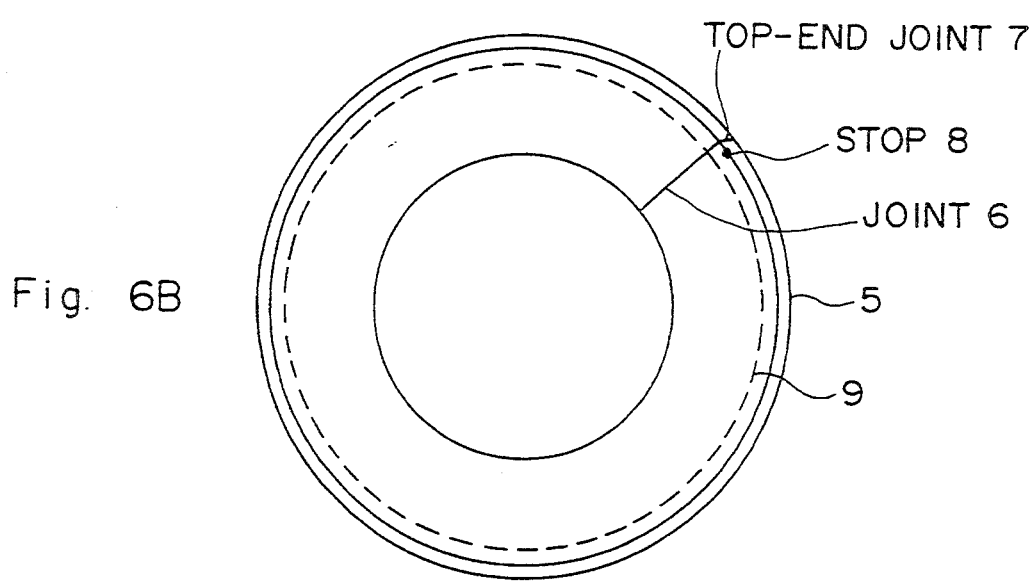

FIGS. 5A and 5B are sample top views of a container 2 having a projecting portion 2a which often generates highlighted portions 4-1, 4-2, etc. in series according to the form of the container's bottom or the variations in the reflection of a light off the side of the container.

Specifically, most metallic containers have a mirror like inner surface and cause the above described problems.

Such highlighted portions can be hardly removed only by appropriately using an illumination. Therefore, the conventional defect detecting method has, in vain, to solve the above described uneven illumination generated as a highlighted portion inside a test container in testing its inner surface.

An object of the present invention is to provide a cylindrical container's inner surface tester for detecting a defective portion stably and precisely even though there is uneven illumination inside a test container.

To solve the above described problems, the cylindrical container's inner surface tester illuminates from above in the axis direction of a container (for example, by a ring illumination 101) the inner surface of an axis-symmetrical cylindrical container (2, for example). A TV camera picks up the illuminated area of the cylindrical container from above in the axis direction. Then, the picked-up image is analyzed by a defect detecting unit (for example, a defect detecting circuit 27, a detected defect determining circuit 32, etc.) to determine a black or white spot inside the cylindrical container.

The tester is also provided with a circularity tester (an image edge detecting circuit 26, a highlighted portion determining circuit 31, etc.) for testing the circularity of a highlighted area in the picked-up image, and determines the acceptability of the inner surface of the cylindrical container according to the check results of the defect detecting unit and the circularity tester (through a general determining circuit 35, etc.).

To solve the above described problems, the cylindrical container's inner surface tester illuminates from above in the axis direction of a container (for example, by a ring illumination 1) the inner surface of an axis-symmetrical cylindrical container (2, for example) capable of being arranged adjacently to others in a predetermined direction (for example, in the horizontal direction). A TV camera picks up the illuminated area of the cylindrical container from above in the axis direction. Then, the picked-up image is analyzed by a defect detecting unit (for example, a defect detecting circuit 27, a detected defect determining circuit 32, etc.) to determine a black or white spot inside the cylindrical container.

The tester comprises a scanning-line-direction position specifier (an image edge detecting circuit 26, etc.). The specifier obtains a binary image signal by performing a binary conversion, for the purpose of obtaining a binary image of the highlighted opening (3, for example) of the cylindrical container, on an image signal (for example, a multi-value continuous tone image signal PO) obtained by scanning the picked-up image. Then, it specifies the position of the test cylindrical container in the scanning-line direction according to the coordinates of the middle points (MA, MB, etc.) between first rise points (A0, B0, etc.) and last fall points (A1, B1, etc.) in the same scanning line of a binary image signal, among the above described binary image signals, in the area not affected by the above described adjacent arrangement (area except the area E, etc.).

In the cylindrical container's inner surface tester, the above described position specifier defines an average value of a plurality of coordinates of middle points in the scanning lines as a specific value indicating the above described position.

To solve the above described problems, the cylindrical container's inner surface tester illuminates from above in the axis direction of a container (for example, by a ring illumination 1) the inner surface of an axis-symmetrical cylindrical container (2, for example) capable of being arranged adjacently to others in a predetermined direction (for example, in the horizontal direction). A TV camera picks up the illuminated area of the cylindrical container from above in the axis direction. Then, the picked-up image is analyzed by a defect detecting unit (for example, a defect detecting circuit 27, a detected defect determining circuit 32, etc.) to determine a black or white spot inside the cylindrical container.

The tester comprises a projector (a Y projecting circuit 30, etc.) and an adjacent area isolator (a process area determining circuit 34, etc.). The projector obtains a binary image signal by performing a binary conversion, for the purpose of obtaining a binary image of the highlighted opening (3, for example) of the cylindrical container, on an image signal (for example, a multi-value continuous tone image signal PO) obtained by scanning the picked-up image. Then, it projects the above described binary image signal in the direction perpendicular to the above described adjacent arrangement direction (in the Y direction, etc.). The adjacent area isolator obtains the difference in the number of image elements between the normal image and the projected image, checks the difference in the number of picture elements from the center of the image of the cylindrical container to its circumference (to the opening of the container), detects a point where the difference in the number of picture elements exceeds a predetermined threshold (for example, the maximum difference projection point PM) in the area from the center to a point where the difference in the number of picture elements first falls to a negative, adds a predetermined correction value ($\beta$, for example) to the coordinates of the detected point, and extracts the above described adjacent arrangement area using the resultant coordinates.

To solve the above described problems, the cylindrical container's inner surface tester illuminates from above in the axis direction of a container (for example, by a ring illumination 1) the inner surface of an axis-symmetrical cylindrical container (2, for example). A TV camera picks up the illuminated area of the cylindrical container from above in the axis direction. Then, the picked-up image is analyzed to determine a black or white spot inside the cylindrical container.

The cylindrical container's inside surface tester comprises a defective peak/valley determiner (for example, an antecedent of an AND gate in a peak/valley detection and binary-conversion circuit 44), an image test area divider, and a value changer.

The defective peak/valley determiner determines that a target picture element is defective if two differences obtained by subtracting the value (for example, PO(i,j)) of a target picture element in the same picture element scanning line for a continuous tone image signal (test area continuous tone image signal 43a, etc.) which is obtained by scanning the above described picked-up image from the values (PO(i+a, j), PO(i−a, j), etc.) of two background picture elements (hereinafter referred to as a forward background picture element and a backward background picture element respectively) a predetermined number of picture elements (hereinafter referred to as picture elements) backward or forward of the target picture element indicate the same polarity, if an absolute value of one of the above described two differences is larger than a predetermined first threshold (THD, for example) corresponding to the polarity, and if the other absolute value is larger than a predetermined second threshold (THD, for example).

The divider divides (into Z1–Z4, Za–Zc, etc.) the test area of a target image of the defective peak/valley determiner according to the optical features of a cylindrical container's inner surface illuminated by the above described illuminator.

The value changer changes at least one value among the number of the above described $\alpha$ picture elements, the first threshold, and the second threshold.

The tester comprises a frame memory for storing as the data for the above described captured image a multi-value continuous tone image signal A/D-converted from a continuous tone image signal obtained by scanning the captured image, and an area detecting unit for generating a binary image signal by binary-converting using a predetermined threshold a multi-value continuous tone image signal read by horizontally or vertically scanning the frame memory and for determining as a test area the area between the first rise point and the last fall point of each scanning line of the binary image signal.

Another cylindrical container inner surface tester according to the above described tester further comprises a masking unit for masking using predetermined mask pattern data an area different in optical characteristics from that in a test area detected by the area detecting unit.

Another configuration is described below.

The captured image is analyzed to determine a black or white spot inside the cylindrical container. The image of the inner surface of the cylindrical container is scanned along a ring or spiral scanning line (hereinafter referred to as a circular scanning line) which is centered on the center of the image and varies sequentially per cycle of a radius varying every one or more picture elements predetermined. Then, the absolute value indicating the difference between the intensity of the target picture elements among a plurality of picture elements arranged at intervals such that one or more picture elements are arranged between two target picture elements and the intensity of background picture element predetermined number of a plurality of picture elements forward or backward of the target picture element is compared with a threshold predetermined according to the position of the circular scanning line. The above described processes are repeated for each target picture element, and a determining unit determines a defective container inner surface when an absolute value larger than the value of the difference between the above described intensity values is detected.

The above mentioned threshold must be set as the optimum threshold per circle of the circular scanning line.

The intensity of the background picture element refers to an average intensity value among the picture elements in a predetermined one-dimensional or two-dimensional local area centered on the background picture element.

Defects can be detected precisely by divisionally extracting highlighted portions after a binary conversion and checking the circularity of the divisionally extracted patterns to collectively detect the deformation, irregular concave, and black dust spots on test objects. Then, black and white spots are checked concurrently in the same window area, thereby reducing the number of window areas and performing the whole process at a high speed.

An average value of the coordinates of middle points between first rise points and last fall points in the same scanning line of a binary image signal in the area not affected by the above described adjacent arrangement is obtained to specify the position of a test cylindrical container prior to this circularity check.

The projected amount of the binary image of the highlighted portion at the opening projected in the direction perpendicular to the adjacent arrangement of containers is obtained to isolate a test area from the area of an adjacent container. Then, the difference between the normal image and the projected image is searched for from the center to the edge of the container so that the adjacent point can be detected.

A target picture element value and two background picture element values are extracted. The target picture element value (coordinates x=i and y=j) at a target point PO(i,j) are associated with a multi-value continuous tone image signal PO(x,y) based on the raster scanning operation. The background picture element values of two background points PO(i+$\alpha$, j) and PO(i−$\alpha$, j) indicate the value of the points each picture elements forward and backward of the above described point PO(i,j) in the x direction of the scanning line are extracted. Then, the intensity relationship where the relationship among these three points indicates a valley when detected as a black level while it indicates a peak when detected as a white level is detected (that is, the difference in intensity between a background picture element value and a target picture element value is detected). The target picture element value PO(i,j) is determined to be a defective picture element when the absolute value indicating the difference in the intensity exceeds a predetermined threshold THD.

Figures 7A, 7B:
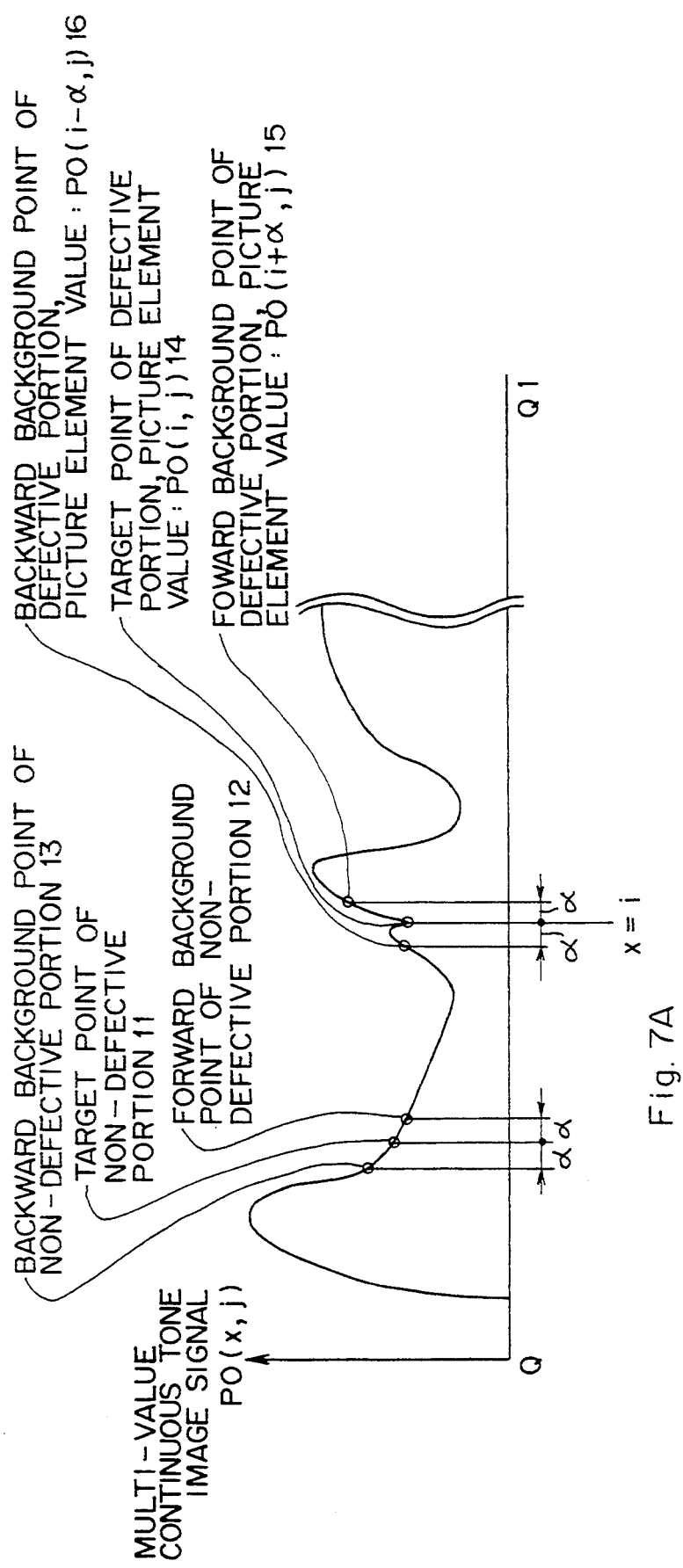
FIGS. 7A and 7B show the principle of the method of detecting a valley and performing a binary conversion.

FIGS. 7A and 7B show the principle of the valley-detection binary-conversion method which is the most important point in the present invention. FIG. 7A shows an example of a multi-value continuous tone image signal PO(x,y) in the scanning line Q-Q1 (y=j), where 11 is a target point in a non-defective portion; and 12 and 13 are forward background point and backward background point of a non-defective portion respectively picture elements forward and backward of the target point 11 in the scanning line.

Likewise, 14 is a target point in a defective portion; and 15 and 16 are forward background point and backward background point of a non-defective portion respectively picture elements forward and backward of the target point 11 in the scanning line.

If the following expressions exist when the coordinates of a target point are (i,j) (that is, x=i and y=j), a binary function value POD(i,j)(referred to as a binary defective peak/valley image signal) for detecting a defect on a target point equals 1, and the target point is determined to be a valley (defect).

$$PO(i-\alpha, j) - PO(i,j) > THD \quad (1) \text{ and}$$

$$PO(i+\alpha, j) - PO(i,j) > THD \quad (2)$$

where THD indicates a predetermined threshold (positive value).

The non-defective portion shown in FIG. 7A does not apply to the above described expression (2), and no defects are detected. However, expressions (1) and (2) exist in the defective portion shown in FIG. 7A and a valley defect is detected. FIG. 7B shows the above described peak/valley binary image signal POD (x,j) as an output of defect determination.

Thus, an optimum detecting performance can be realized by dividing the waveform shown in FIG. 7A into a plurality of small areas and appropriately assigning to each of the small areas a threshold THD and the number $\alpha$ of picture elements indicated in expression (1) and (2) above.

When a peak (defect) is detected by the present invention, the target point is determined to be a defective peek having the peak/valley binary image signal POD-(i,j)=1 if the following expressions exist where the position of the difference paragraph in each of the above described expressions (1) and (2) is exchanged with the other paragraph as follows.

$$PO(i,j) - PO(i-\alpha, j) > THD \quad (1A)$$

$$PO(i,j) - PO(i-\alpha, j) > THD \quad (2A)$$

Figure 2A:
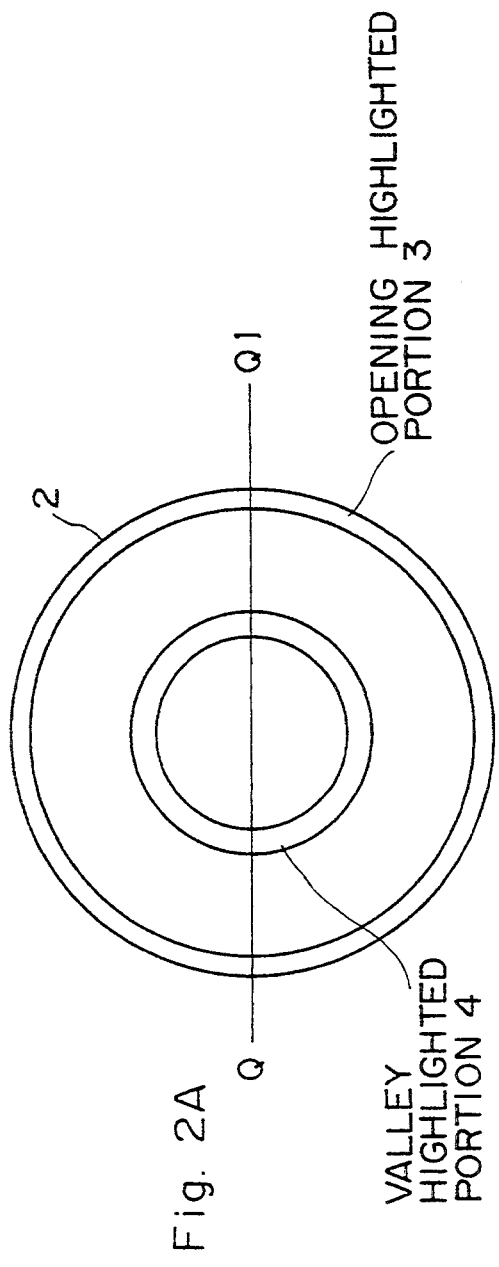
FIGS. 2A and 2B show the relationship between the intensity variations inside a cylindrical container and the conventional division of a window.
Figure 2B:
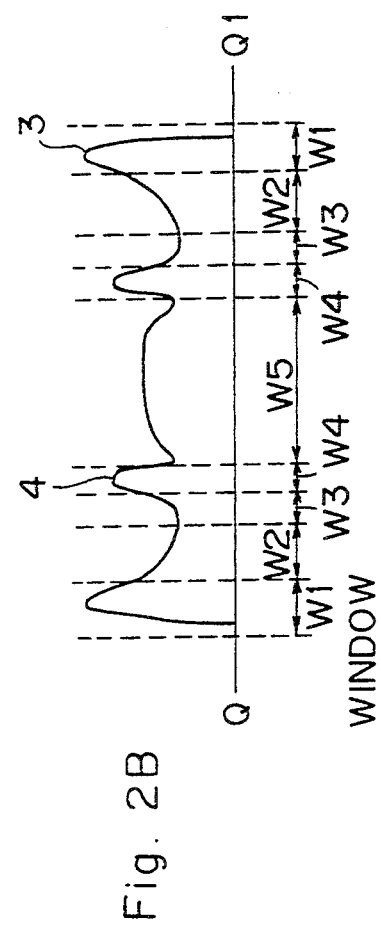
Figure 3:
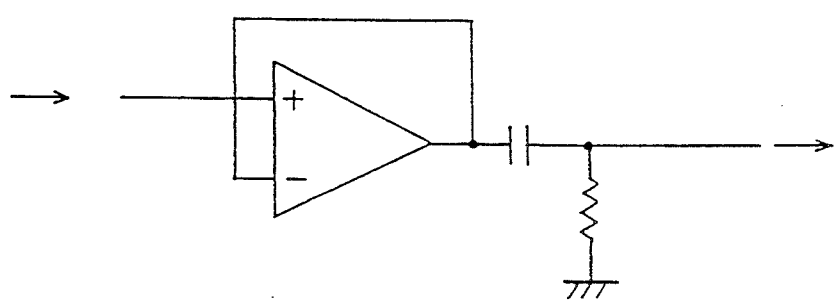
FIG. 3 shows an example of an analog differentiation circuit.

The tester for easily detecting defective concaves illuminates from above in the axis direction of a container the inner surface of an axis-symmetrical cylindrical container using a ring-shaped illuminator. When a TV camera captures the illuminated area of the cylindrical container from above in the axis direction and the captured image is analyzed, the distribution of the continuous tone on the container inner surface is concentrically generated as shown in FIGS. 2A and 2B. Taking this into account, a picture element string is obtained by scanning the container inner surface along the ring or spiral circular scanning line. When a defective concave exists, it appears as a continuous tone in the scanned picture element string. Thus, the absolute value $\Delta P$ indicating the difference between the intensity PO of the target picture elements in a scanned picture element string and the intensity P1 of the background picture element d picture elements forward or backward of the target picture element is calculated by the following equation.

$$\Delta P = || PO - P1 \Delta$$

A threshold THP is assigned to each of the windows W1 through W5 shown in FIG. 2B, and the threshold THP is compared with the absolute value $\Delta P$ indicating the difference between the intensity values. If $\Delta P$ is larger than the THP, the target picture element is determined to be a picture element of a defective inner surface such as a concave, etc.

However, the threshold THP can be set per circle of the circular scanning line, for example, according to its position. The intensity P1 of the background picture element can be an average intensity the value among picture elements in a one-dimensional local area (that is, a series of n picture elements on the scanning line) or a two-dimensional local area (that is, a local area comprising n picture elements by n picture elements.

Figure 8:
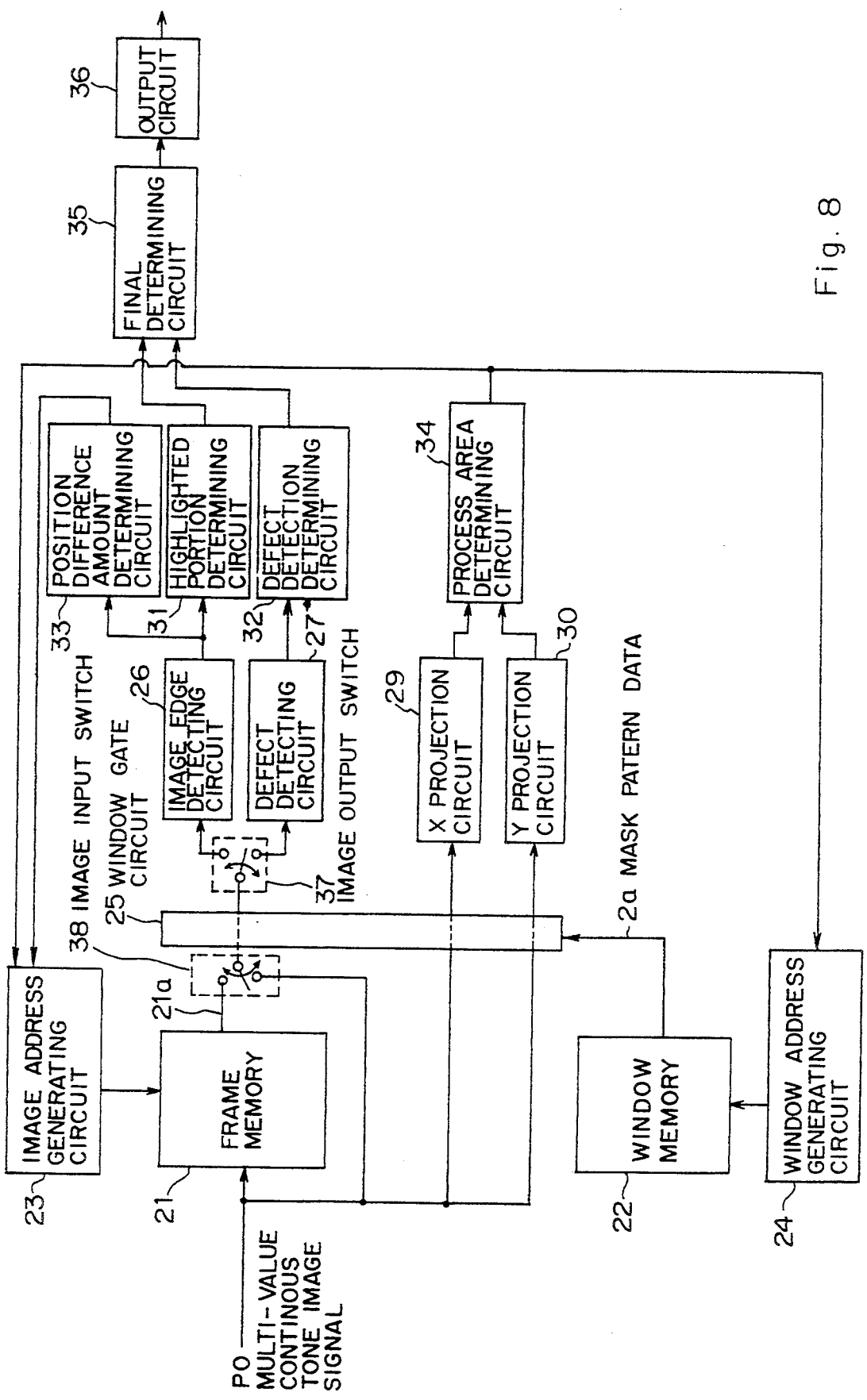
FIG. 8 is a block diagram of the hardware configuration of the embodiment of the present invention.

An embodiment of the present invention is explained by referring to FIGS. 8 through 25. FIG. 8 is a block diagram of hardware as an embodiment of the present invention. In FIG. 8, PO is a multi-value (example, 8-bit, for example) continuous image signal generated by AD-converting a video signal obtained by raster-scanning a screen of a TV camera; a frame memory 21 receives this multi-value continuous tone image signal PO and stores it as a piece of multi-value screen data; and an address generating circuit 23 generates addresses for the frame memory 21. A window memory 22 stores a mask pattern prepared for each window; an address generating circuit 24 generates addresses for the window memory 22; and a window gate circuit 25 masks a multi-value continuous tone image signal PO or an image signal 21a read from the frame memory 21 with a mask pattern data 22a from the window memory 22, and passes the image signal PO or the image signal 21a in a specified window area.

An image input switch 38 selectively switches either to the multi-value continuous tone image signal PO or to the frame memory image signal 21a. The switch 38 applies to an image edge detecting circuit 26 the latest multi-value continuous tone image signal PO in parallel with an input of the signal PO to the frame memory 21 so that a position difference amount determining circuit 33 described later can be operated.

An image output switch 37 switches an output image signal from the image input switch 38 received through the window gate circuit 25 to the image edge detecting circuit 26 or a defect detecting circuit 27.

The image edge detecting circuit 26 detects the edge of an image, that is, the outer point (point in an outer circumference) and the inner point (point in the inner circumference) of a ring-shaped highlighted portion. In the detecting operation, an inputted image signal is converted into binary data using a threshold predetermined for detecting the position of a target image and for use in a circularity test, etc. Then, the coordinates of rise points and fall points of the binary signal are stored as image edge data in a memory (26A through 26D described later by referring to FIG. 13) of the image edge detecting circuit 26.

A circuit 31 checks the circularity on the coordinates of the points in an outer or inner circumference detected by the image edge detecting circuit 26.

To open a window at the right position relative to a target image, the position difference amount determining circuit 33 detects the difference amount between the center of the current target image detected by the input of the latest multi-value image signal P0 from the image edge detecting circuit 26 and the center of a predetermined window.

The defect detecting circuit 27 detects a defect (black or white spot) by the differentiation method described in the prior art technology and calculates an area, etc. A defect detection determining circuit 32 compares a detection result of the circuit 27 with a predetermined value to determine the acceptability.

An X projection circuit 29 obtains an X-direction projection pattern of a target image using a multi-value image signal PO received through the window gate circuit 25. Likewise, a Y projection circuit 30 obtains a Y-direction projection pattern of a target image. A process area determining circuit 34 determines the image area of a test container not adjacent to images of other containers using the data outputted from the two projection circuits 29 and 30.

A final determining circuit 35 receives determination results from the highlighted portion determining circuit 31 and the defect detection determining circuit 32 to give a final determination, An output circuit 36 indicates the acceptability of a test container according to an output determination signal outputted by the final determining circuit.

Figure 9A:
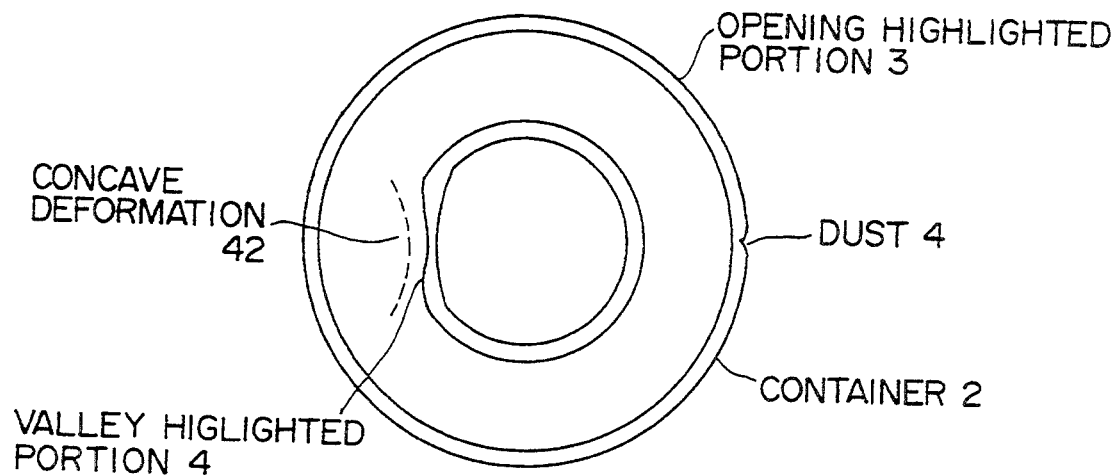
FIGS. 9A and 9B show the influence of a defective inner surface of a container on a highlighted portion.
Figure 9B:
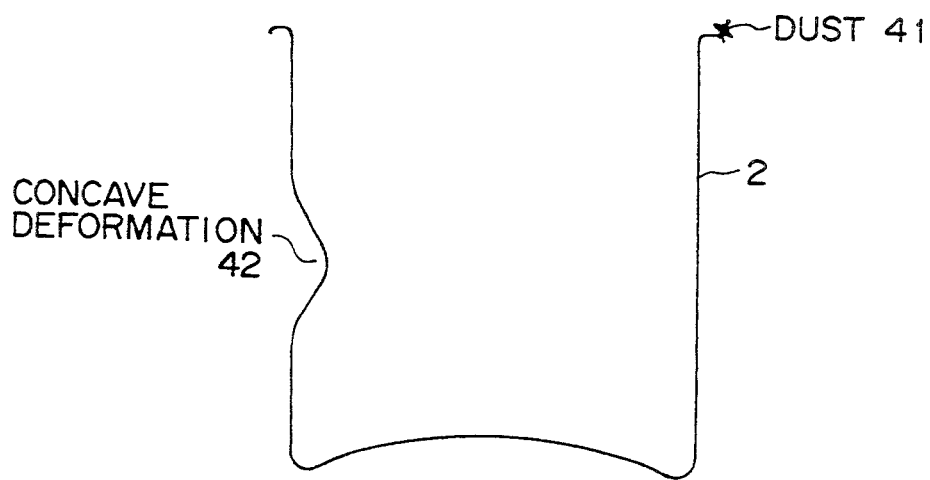

FIGS. 9A and 9B show the influence of a defect in the highlighted portion of a can, which has a defect in the inner surface, observed from above. FIG. 9A is a plan view; and FIG. 9B is a sectional view. When there is dust detected at the opening of a container 2, it is detected as a lack in a circumference which indicates the highlighted portion 3 at the opening as shown in FIG. 9A. If there is a big concave deformation 42 on the side of a container, it can be detected as a deformation in the highlighted bottom portion 4. However, unlike dust, etc., since a concave deformation indicates a small contrast difference, the concave deformation 42 can be easily detected by the circularity check performed on the highlighted bottom portion 4.

Figure 10:
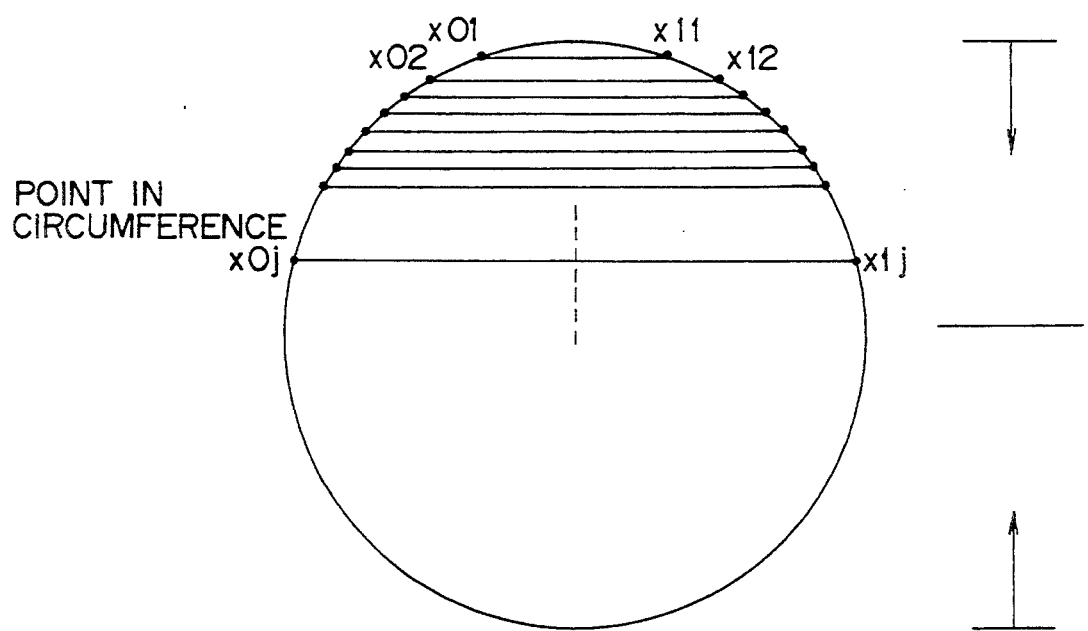
FIG. 10 is a view of points in the circumference of a highlighted portion which are used in a circularity test.

FIG. 10 is a view for explaining the circularity detecting method operated by the highlighted portion determining circuit 31. In FIG. 10, "x0j" and "x1j" respectively indicate a rise point and a fall point of coordinates of a point in an outer circumference which indicates a highlighted portion of a non-defective container (where $j=1,2,\ldots$, that is, j is a parameter corresponding to a coordinate of "y" in the horizontal scanning line). First, the coordinate variation $X_{k+1}-X_k$ of a non-defective container is calculated. Then, the maximum value (max (a, b) described later) and the minimum value (min (a, b) described later) which provide the above described allowable range are respectively stored in the maximum value table TB1 and the minimum value table TB2 each shown in FIG. 11 as allowable value tables TB. In this case, the value k is 0j or 1j.

In FIG. 10, since images are not stable at a several lines near the top and the bottom, they must be excluded or assigned a large allowable value. Therefore, the allowable value of $X_{K+1}-X_K$ is determined as follows based on the coordinate variation of a non-defective container.

$$\min(a,b)-\alpha < X_{k+1}-X_k < \max(a,b)+\alpha$$

where max(a,b) means the maximum value "a" or "b" (shown below) whichever is larger. Likewise, min(a,b) means the minimum value "a" or "b" whichever is smaller.

$$a = X_k - X_{k-1}$$

$$b = X_{k+2} - X_{k+1}$$

α is a fixed value for moderating a detected sensitivity in consideration of a quantization error, etc. Generated when an image is converted to a digital image.

"a" and "b" can also be assigned to determine the allowable range of two lines as follows.

$$a = X_{k-1} - X_{k-2}$$

$$b = X_{k+3} - X_{k+2}$$

Figure 11:
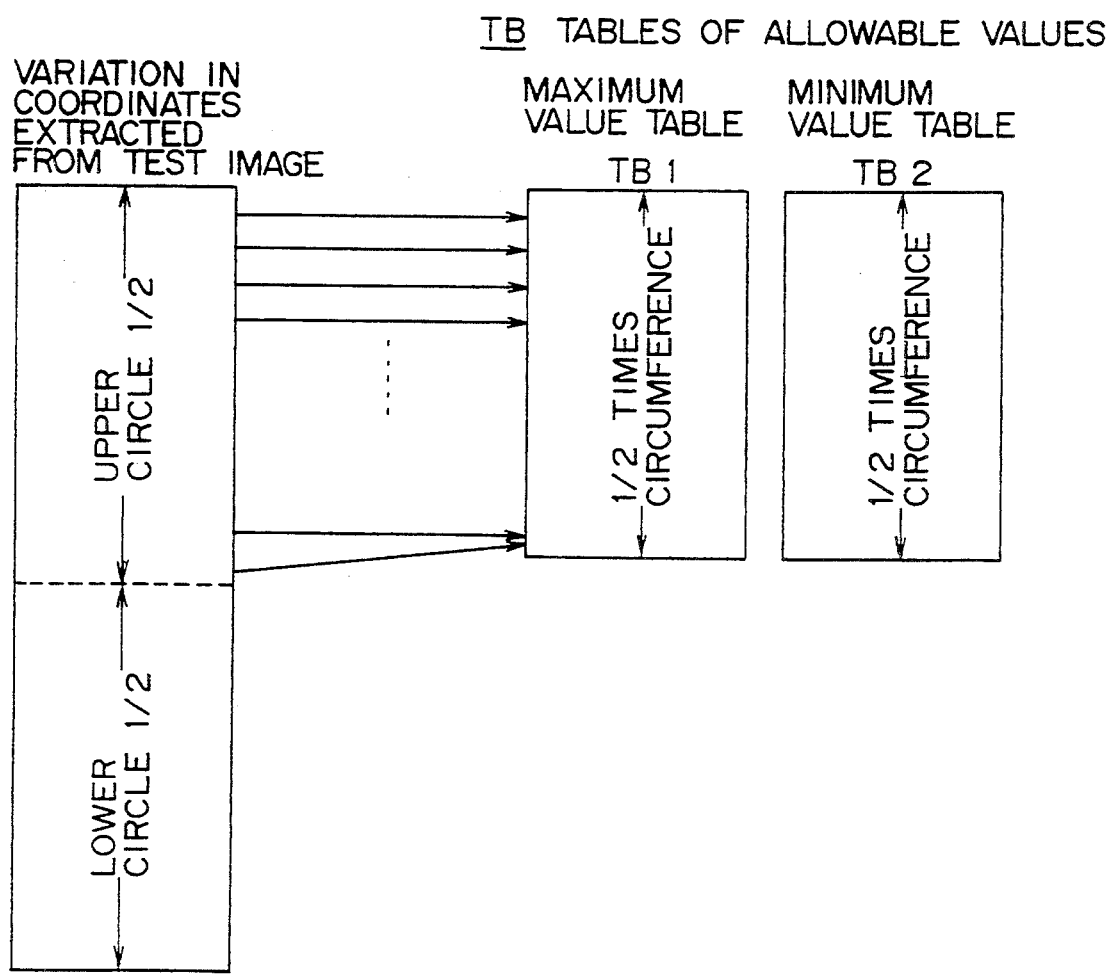
FIG. 11 is a block diagram for explaining the determination of the circularity.

Thus, the highlighted portion determining circuit 31 stores an allowable value of a non-defective container for each line as a maximum table TB1 and a minimum table TB2 shown in FIG. 11, and serially compares for a circularity test the variation in coordinates of a test image with the allowable value indicated in the table TB1 or TB2.

If a predetermined number of scanning lines of a non-defective container does not match the number of scanning lines of a test image, the above described comparison is performed serially from the top or the bottom of the container to its center. The difference in the number of scanning lines is balanced around the center where the variation is smaller than in upper or lower lines. That is, when the number of lines shown in the allowable table of a non-defective container is smaller, the comparison is performed using the allowable value for the center line (refer to FIG. 11). In FIG. 11, the same process is performed twice for an upper circle and a lower circle, and the allowable value table stores the values only for half a circle.

The above described test is performed for an outer circumference. The test method for an inner circumference is explained below.

Figure 12A:
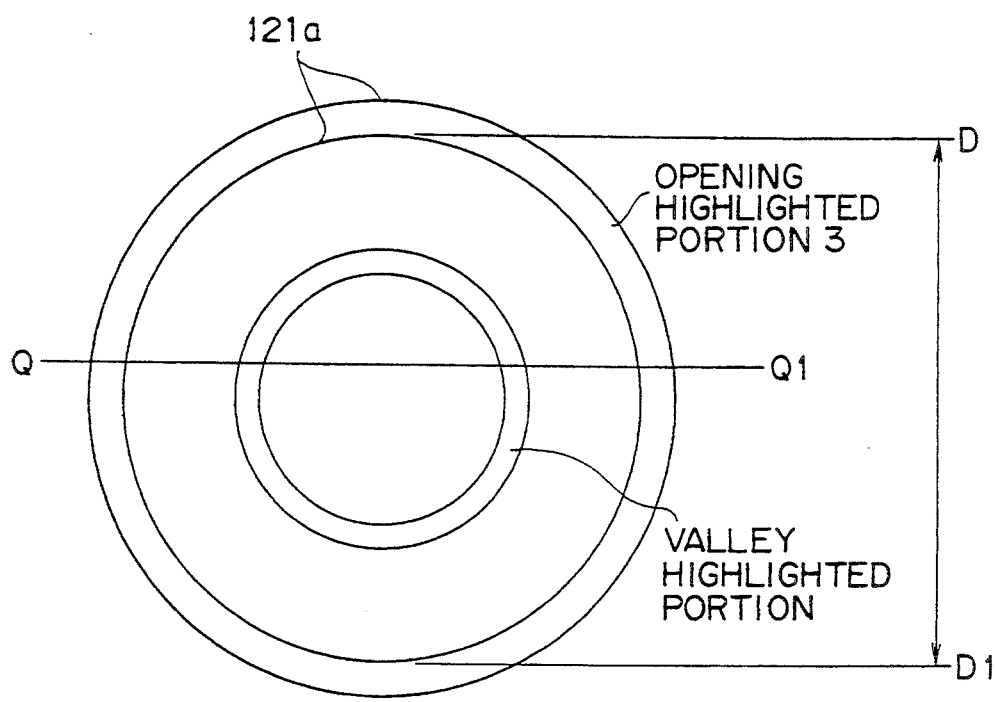
FIGS. 12A and 12B show how to detect a point in an inner circumference of a highlighted portion.
Figure 12B:
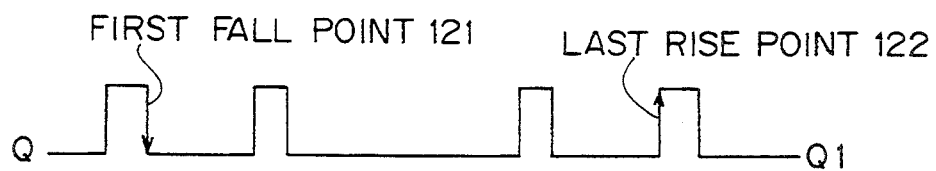

FIGS. 12A and 12B show how to detect coordinates in an inner circumference of a highlighted portion. FIG. 12A is a plan view of a test container; and FIG. 12B shows in binary how continuous tone image signals change at the highlighted portions in the scanning line Q-Q1. First fall points of binary signals 121 in scanning lines shown in FIG. 12B detect the coordinates 121a indicated as the bold curves shown in FIG. 12A. Since the coordinates in the inner circumference range between D and D1, the line D-D1 is determined to be the line where the coordinate variation shows inversion, thereby obtaining the coordinates of the left half inner circle. Likewise, each of the last rise points 122 in each scanning line generates the right half inner circle. Thus, the circularity test is performed on the inner circumference.

Figure 13:
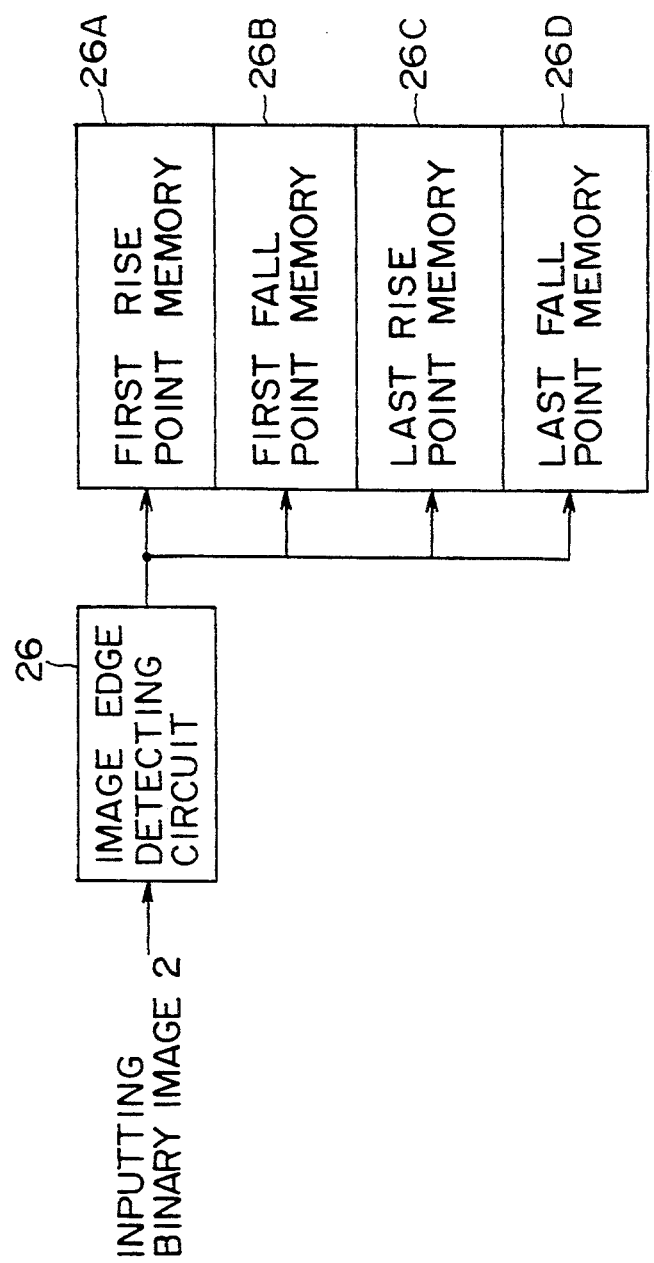
FIG. 13 is a block diagram of the detailed configuration of the image edge detecting circuit.

FIG. 13 shows the further detailed configuration of the image edge detecting circuit 26 shown in FIG. 8. In FIG. 13, a memory 26A stores a first rise point; a memory 26B stores a first fall point; a memory 26C stores a last rise point; and a memory 26D stores a last fall point. The data in the memories 26A and 26D enable an outer circumference to be detected, and the data in the memories 26B and 26C enables an inner circumference to be detected.

Figure 14:
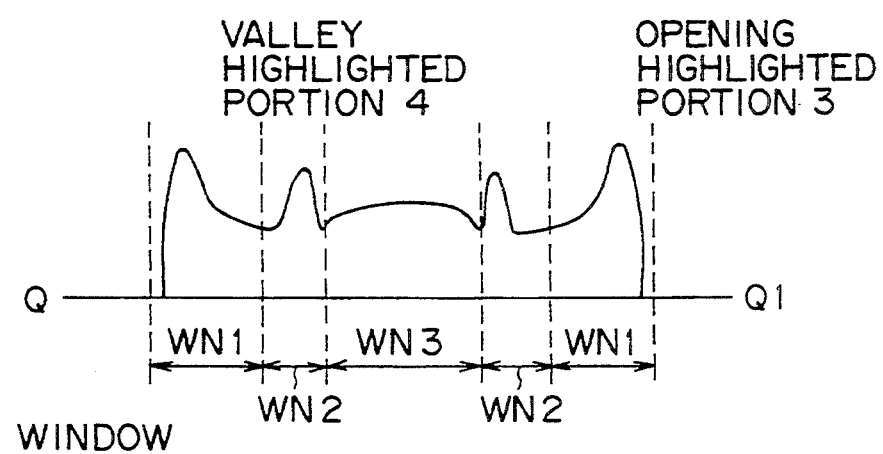
FIG. 14 shows the relationship between the intensity carnations inside a cylindrical container and the division of a window based on the present invention.

The deformation and a concave on a container, and dust attracted to it can be detected with a high defect-detection precision when the above described outer circumference is tested in a circularity test on the highlighted portions. Therefore, the number of windows can be reduced by concurrently detecting black and white spots through the circularity test and the conventional defect detecting circuit. FIG. 14 corresponds to FIG. 2B, and shows an embodiment of a window based on the present invention. That is, in FIG. 14, a new window WN1 is generated by combining a window W1 including the highlighted opening portion 3 shown in FIG. 2B and the adjacent window W2. Likewise, a new window WN2 is generated by combining a window W4 including the highlighted bottom portion 4 shown in FIG. 2B and the adjacent window W3. Another new window WN3 corresponds to a window W5 for the central part of the bottom shown in FIG. 2B. Thus, there are three window areas WN1, WN2, and WN3, thereby decreasing the number of areas.

Figure 15:
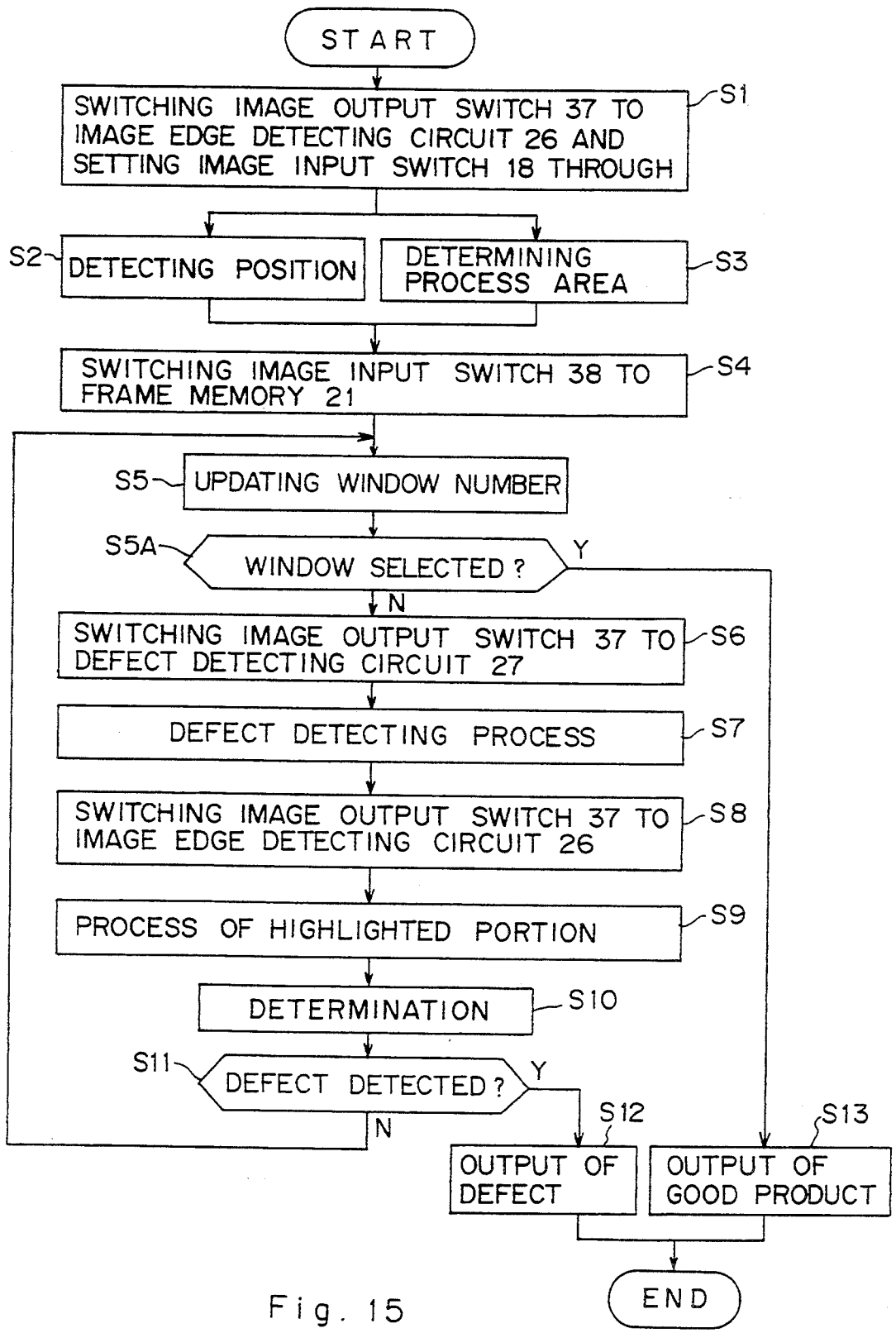
FIG. 15 is a flowchart for explaining the procedure of the operation associated with the configuration.

FIG. 15 is a flowchart indicating the procedure of the operation shown in FIG. 8. The operation is explained by referring to FIG. 15. Numbers S1–S13 indicate the step numbers shown in FIG. 15. First, the image output switch 37 is switched to the image edge detecting circuit 26. Simultaneously, the image input switch 38 is put through, that is, switched to directly input a multi-value image signal PO (S1). Thus, the difference in the position of a target image is detected (S2). Simultaneously, a process area is determined through the X projection circuit 29, the Y projection circuit 30, and the process area determining circuit 34 (S3).

That is, in step S2, the position difference amounts Δx and Δy of a container image are obtained through the position difference amount determining circuit 33, and a value for correcting a horizontal position difference is sent to the image address generating circuit 23 so that a window can be generated at the right position. In step S3, a container image is isolated from another if they are arranged adjacent to each other by the process area determining circuit 34 so that one scanning area does not contain adjacent container images.

Then, the image input switch 38 is switched to the frame memory 21 (S4), and the following acceptability determining process is performed based on the continuous tone image data 21a in the frame memory 21. First, a test window area of a test can refers to the area of the window WN1 including the highlighted opening portion 3 and masks other window areas WN2 and WN3 (S5). Next, the process in step S6 is performed until the test is completed for all the windows (branch to N in step S5A). In step S6, the image output switch 37 is switched to the defect detecting circuit 27 to detect a defect through the defect detecting circuit 27 and the defect detection determining circuit 32 (S7). The defect detecting circuit 27 detects black or white spots by the differentiation method, etc. to count the number of defective picture elements. The defect detection determining circuit 32 compares the counted number of defective picture elements with a predetermined value to determine the acceptability and output the result to the final determining circuit 35 in the step described later.

Then, the image output switch 37 is switched to the image edge detecting circuit 26 to operate the image edge detecting circuit 26 again, represent highlighted portion in binary as described above so that coordinates or an area of an outer or inner circle can be calculated (S9), perform the circularity test and compare the results with the standard area value through the highlighted portion determining circuit 31 so that the acceptability can be determined, and output the determination result to the final determining circuit 35 in the step described later.

The final determining circuit 35 instructs the output circuit 36 to output a defect (S12) if either the highlighted portion determining circuit 31 or the defect detection determining circuit 32 determines a defect (S10 to S11, branch to Y). If the test container is determined to be a non-defective product in step S11, control is returned to step S5 again, the next test area is the window area WN2 containing the highlighted bottom portion 4, the other areas WN1 and WN3 are masked, and the following steps up to step 12 are repeated. When the tests on all the windows are completed up to the window WN3 (in step SSA, branch to Y), the output circuit 36 is instructed to output the non-defective product through the final determining circuit 35 (S13).

Figure 16:
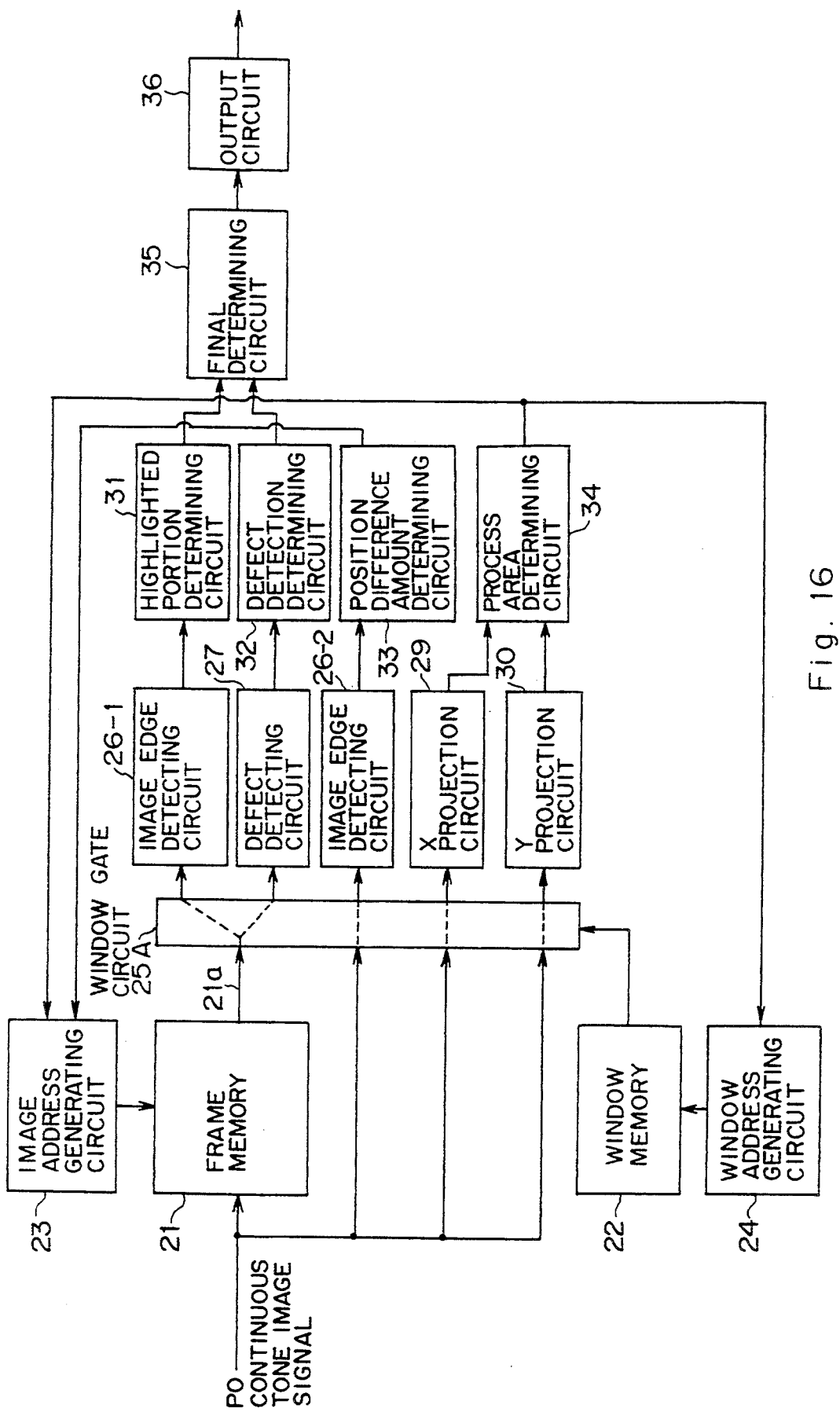
FIG. 16 is a block diagram of the hardware configuration of the embodiment of the present invention.

FIG. 16 shows the block circuit in which the process shown in FIG. 8 can be performed in a high speed. In FIG. 16, the image input switch 38 shown in FIG. 8 is omitted and the window circuit 25 is revised as a new window circuit 25A, two circuits 26-1 and 26-2 corresponding to the image edge detecting circuit 26 are provided where one image edge detecting circuit 26-2 directly receives a multi-value image signal PO (through the window gate circuit 5A) and provides the detection result for the position difference amount determining circuit 33. Furthermore, the image output switch 37 shown in FIG. 8 is omitted and the output image signal 21a from the frame memory is provided concurrently for the other image edge detecting circuit 26-1 and the defect detecting circuit 27 (through the window gate circuit 5A) to concurrently perform the processes by the highlighted portion determining circuit and the defect detecting circuit 31.

Figure 17:
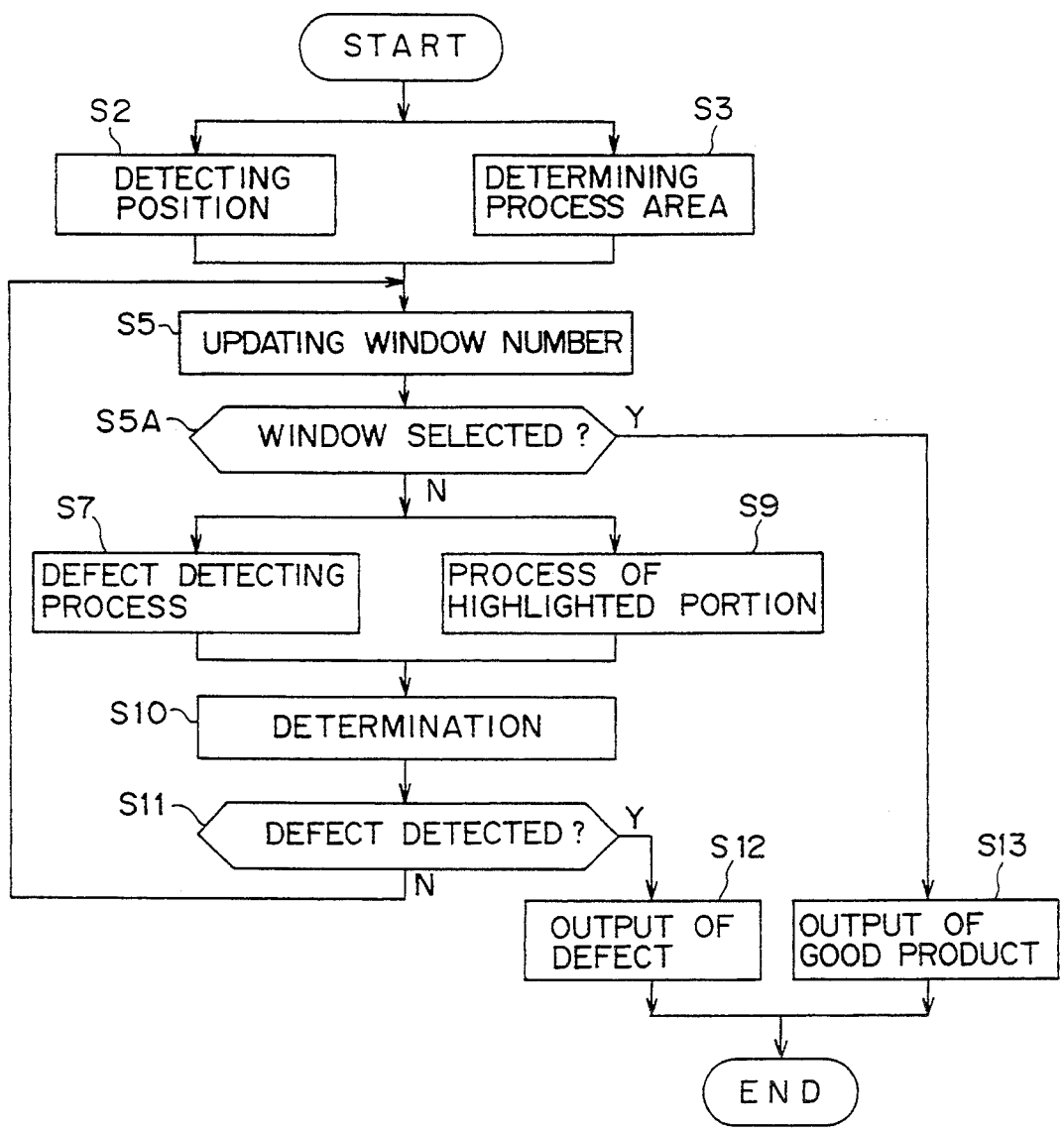
FIG. 17 is a flowchart for explaining the procedure of the operation associated with the configuration.

FIG. 17 is a flowchart for describing the procedure of the operation shown in FIG. 16, where the switching steps S1, S4, S6, and S8 of the switches 37 and 38 are omitted from the procedure shown in FIG. 15. Additionally, the defect detecting process in step S7 and the process of highlighted portions in step S9 are performed concurrently.

Figure 19:
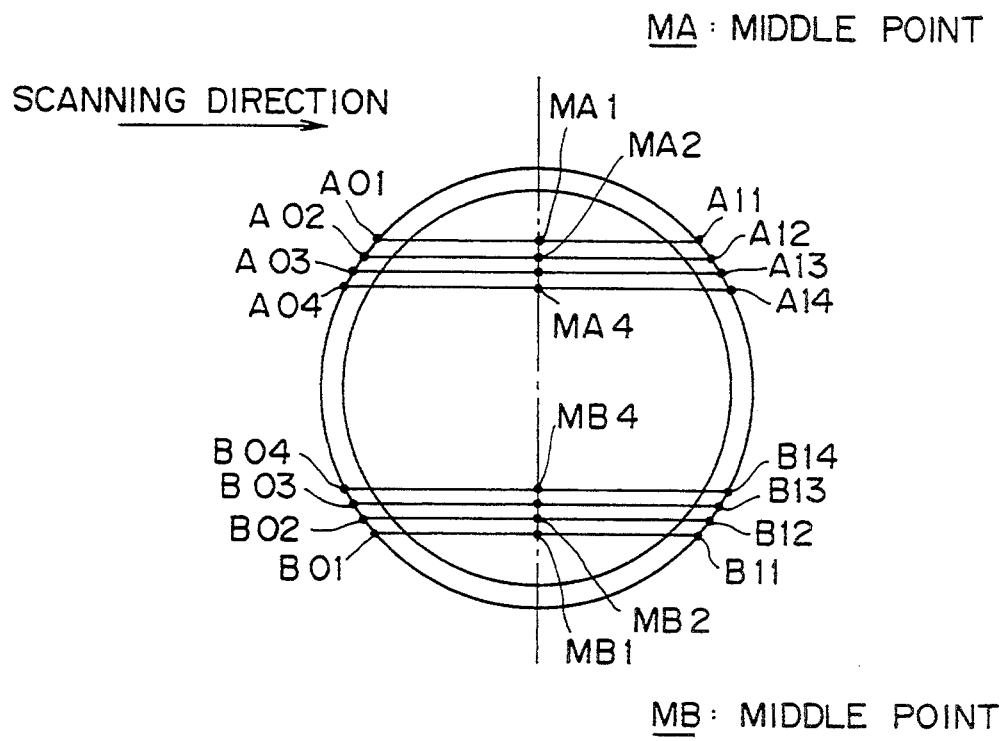
FIG. 19 shows the detailed drawing for supplementing FIG. 18.
Figure 20:
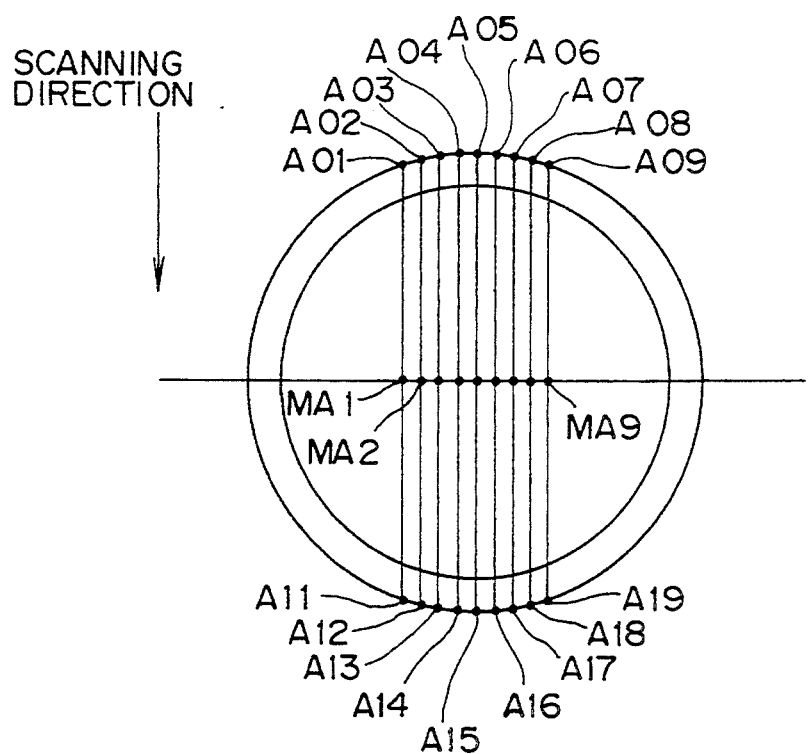
FIG. 20 show hot to detect a target image in the embodiment of the present invention.

FIGS. 19 and 20 are explanatory views of a highlighted bottom portion of a container whose bottom is formed uniquely. FIG. 19 is a plan view (image); and FIG. 20 is a sectional view. In this embodiment, the highlighted bottom portion 4 is generated as 4-1 and 4-2. In this way, a highlighted bottom portion can be generated concentrically in more than one circle depending on the shape of the bottom part of a container. In this case, the bottom area is appropriately divided and the number of windows is increased correspondingly. Step S5 shown in FIGS. 15 and 17 shows a conditional branch involved. Since a bottom portion is a comparatively small area to be scanned, it can be processed at a high speed even though the number of windows is increased to some extent.

Figure 18:
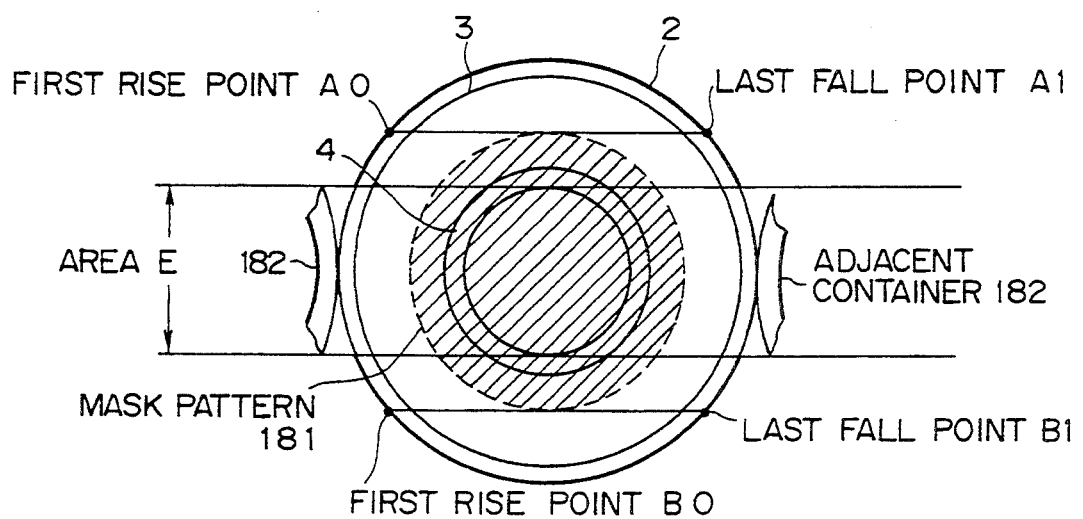
FIG. 18 shows how to detect the position of a target image in the embodiment.

Additional explanation about an embodiment of a position detecting operation performed for a test image by the image edge detecting circuit 26 (FIG. 8) is given below by referring to FIGS. 34 and 37. FIG. 18 shows an image of a highlighted portion converted to the binary representation by the image edge detecting circuit 26. In FIG. 18, 181 is a mask pattern, and 182 is a container adjacent to a test container 181. That is, the highlighted bottom portion 4 is masked by the mask pattern 181 through the window gate circuit 25 shown in FIG. 8. The coordinates indicated by the bold curves shown in FIG. 18 can be obtained when first rise points such as A0 and B0 and last fall points such as A1 and B1 are detected in the scanning direction in a binary image. However, incorrect coordinates are obtained in the area E when any container is adjacent to the test container. Therefore, the position of the test container must be detected by the lines near the longest possible lines such as A0-A1 and B0-B1 in the horizontal scanning lines connecting the above described coordinates indicated by the bold curves out of the area E.

FIG. 19 shows how the center positions (x coordinates) along horizontal scanning lines of a test container are obtained by calculating middle points MA (MA1 . . . MA4) of lines A01-A11, . . . , A04-A14 near the lines A0-A1 and B0-B1 out of the area E as described above by referring to FIG. 18, likewise by calculating the middle points MB (MB1 . . . MB4) of lines B01-B11, . . . , B04-B14, and by calculating the average value of these middle points MA1 . . . MA4 and MB1 ... MB4.

The y coordinates can be obtained by calculating the average value of the coordinates of both ends (upper and lower limits) of the X direction projected pattern obtained by the X projection circuit 29 shown in FIG. 8.

FIG. 20 shows an example of a position detection by the method similar to the above described method in which an image is scanned vertically (in the Y direction) after the image is inputted to the frame memory 21a. That is, if containers are conveyed horizontally (in the X direction), they are not adjacent to one another vertically (in the Y direction). Therefore, there is no need to consider the area E shown in FIG. 18.

In FIG. 19, a multi-value continuous tone image signal PO can be used directly. However, in FIG. 20, an image signal 21a must be used from the frame memory 21, thereby causing delay and incorrect position detection of a target image. However, the delay can be minimized by limiting the scanning operation shown in FIG. 20 to a local area.

Figure 21A:
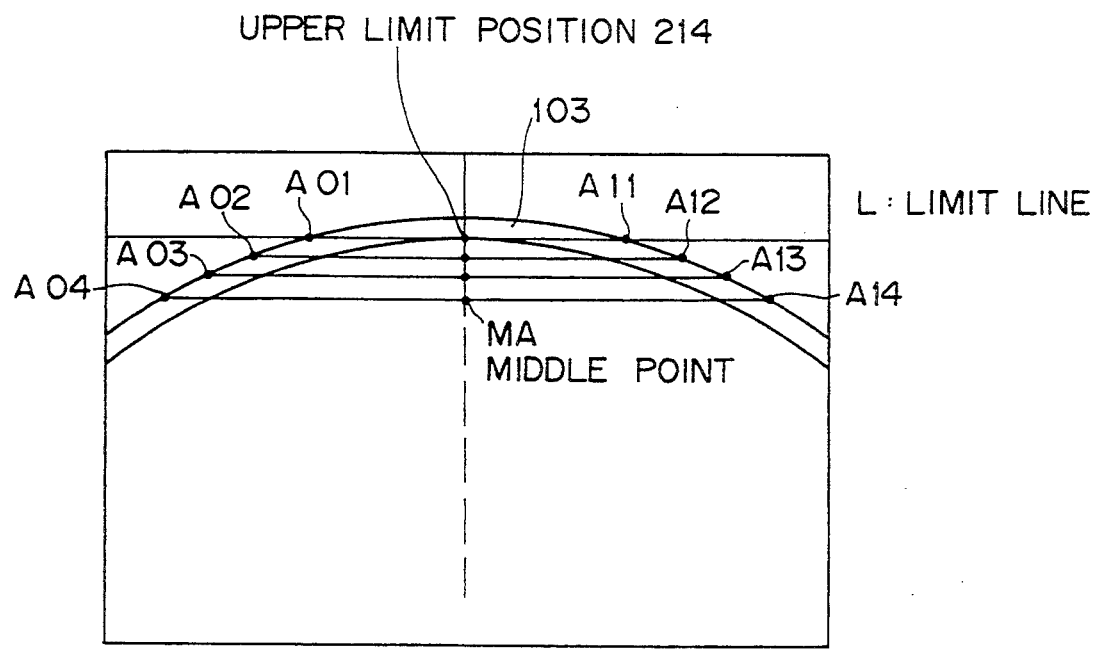
FIGS. 21A and 21B show how to detect a target image in the embodiment of the present invention.
Figure 21B:
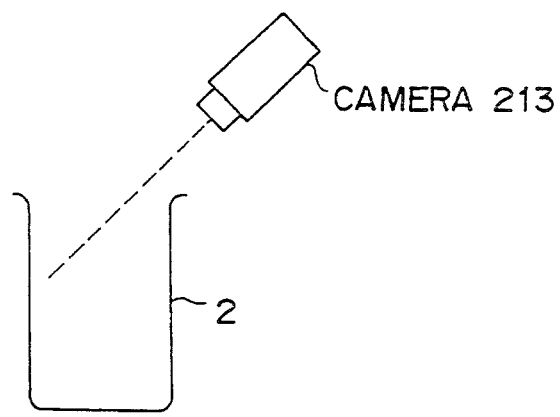

FIGS. 21A and 21B show another example of detecting the position of a container by regarding highlighted portions. This example is picked up by a camera 213 as an oblique top view of the container 2. The highlighted opening portion 3 is observed as a binary image as shown in FIG. 21A. In this detected image, first rise points A01 ... A04 and last fall points A11 ... A14 are obtained in each horizontal scanning line. Then, an average value MA of the middle points of lines A01-A11, ..., and A04-A14 are calculated to specify the horizontal position of the test container. The vertical position of the test container can be specified by obtaining the limit line L at which the length of the horizontal scanning line falls below a predetermined value, thereby specifying the upper limit of the horizontal position of the test container.

This position detecting method can be applied when the upper limit of a container is specified as a predetermined position determination point.

Figure 22A:
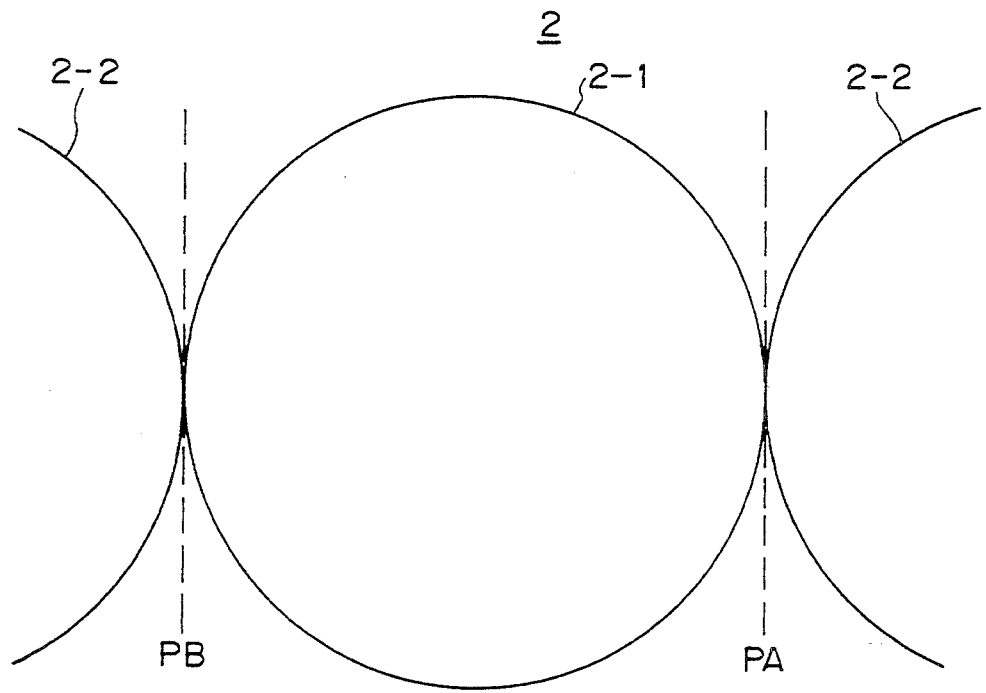
FIGS. 22A to 22C show the conventional method of detecting a container adjacent point.
Figure 22B:
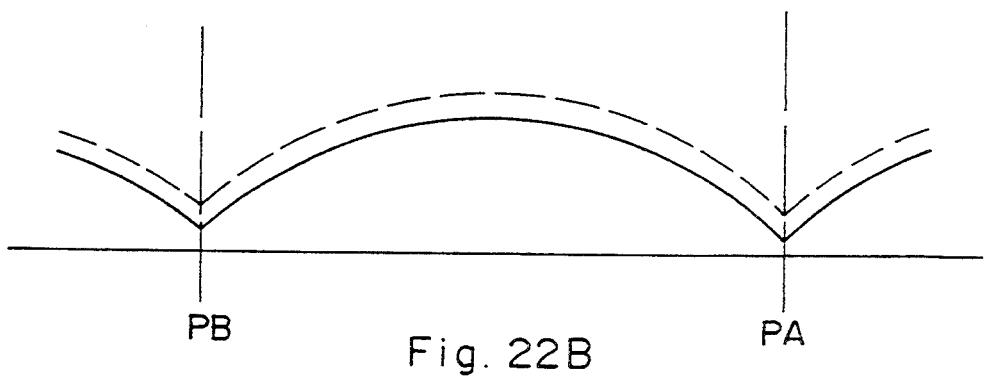
Figure 22C:
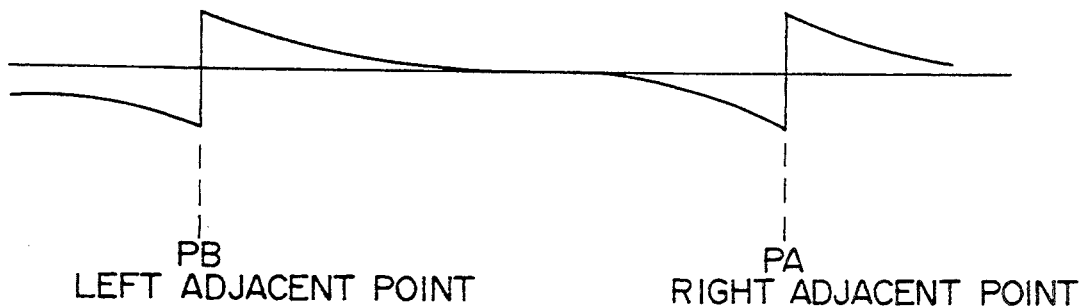

Additional explanation is given below, by referring to FIGS. 22 through 25, about an embodiment of a process area determining operation when a test container is adjacent to other containers. The process area determining circuit 34 shown in FIG. 8 performs an arithmetic operation of determining a process area according to the information from the X projection circuit 29 and the Y projection circuit 30. FIGS. 22A, 22B and 22C show the conventional method of determining a process area. FIG. 22A shows a binary image converted to the binary. representation of the whole container based on a threshold, where 2-1 is a test container; and 2-2 is a container adjacent to the test container 2-1. In this case, the containers are horizontally adjacent to one another.

FIG. 22B shows the number of projected picture elements of the image shown in FIG. 22A calculated in the vertical direction. FIG. 22C shows the difference obtained by subtracting the projected amount (the number of projected picture elements). In a relatively simple pattern shown in FIG. 22B, a right adjacent point PA and a left adjacent point PB can be detected by a change point shown in FIG. 22C, thereby isolating the adjacent containers.

Figure 23A:
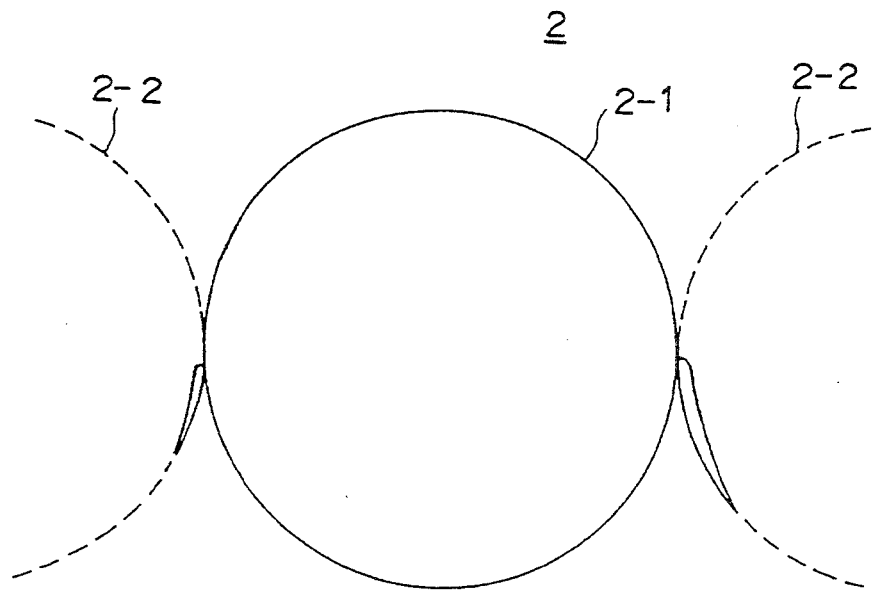
FIGS. 23A to 23C show an example where an adjacent point cannot be detected in the method shown in FIGS. 22A to 22C.
Figure 23B:
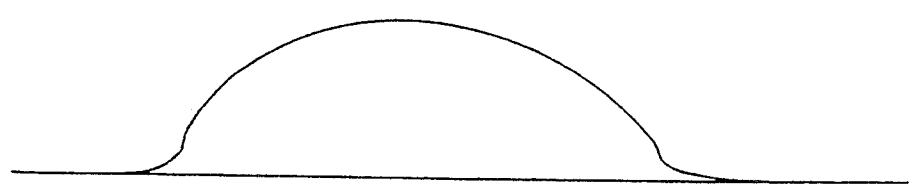
Figure 23C:
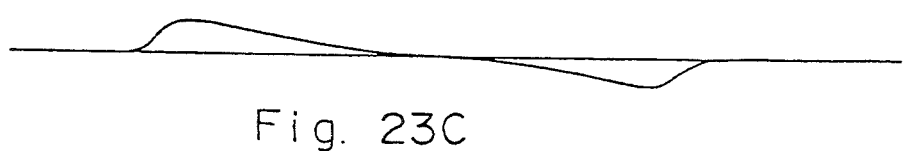

FIGS. 23A to 23C are views for explaining the conventional method similar to one shown in FIGS. 22A to 22C in which adjacent points cannot be detected easily. That is, as shown by the actual test image in FIG. 23A, only a part of adjacent containers may be detected in binary. Therefore, the projection pattern comes out as shown in FIG. 23B, and the difference projection pattern is represented as shown in FIG. 23C, thereby preventing the containers from being isolated easily.

FIGS. 24A to 24C are views for explaining the process area determining method based on the present invention for testing a container adjacent to other ones. That is, a threshold is determined to detect by the Y projection circuit 30 a highlighted opening portion 3 as a ring-shaped image, a multi-value continuous tone image signal PO is converted to the binary representation to obtain a binary image shown in FIG. 24A, and then a projection pattern of this binary image shown in FIG. 24B can be obtained by calculating the projection in the Y direction vertical to the adjacent direction (horizontally, that is, the X direction).

Next, the process area determining circuit 34 calculates the difference in the projected amount (the number of projected picture elements) shown in FIG. 24B from the center to the opening of a test container 2-1 as shown by the arrow 241 in FIG. 24C, and obtains a difference projection pattern as shown in FIG. 24C. Then, adjacent points can be obtained as follows.

That is, to obtain the right adjacent point PA, a detecting operation is performed from a side point P1 to the opening portion shown in FIG. 24C to obtain the point $\Delta$PM at which the maximum difference projected amount is obtained (maximum difference projection point) within the range to the point PD at which the difference projection pattern graph first indicates a turn to decrease (difference decrease start point).

Figure 25:
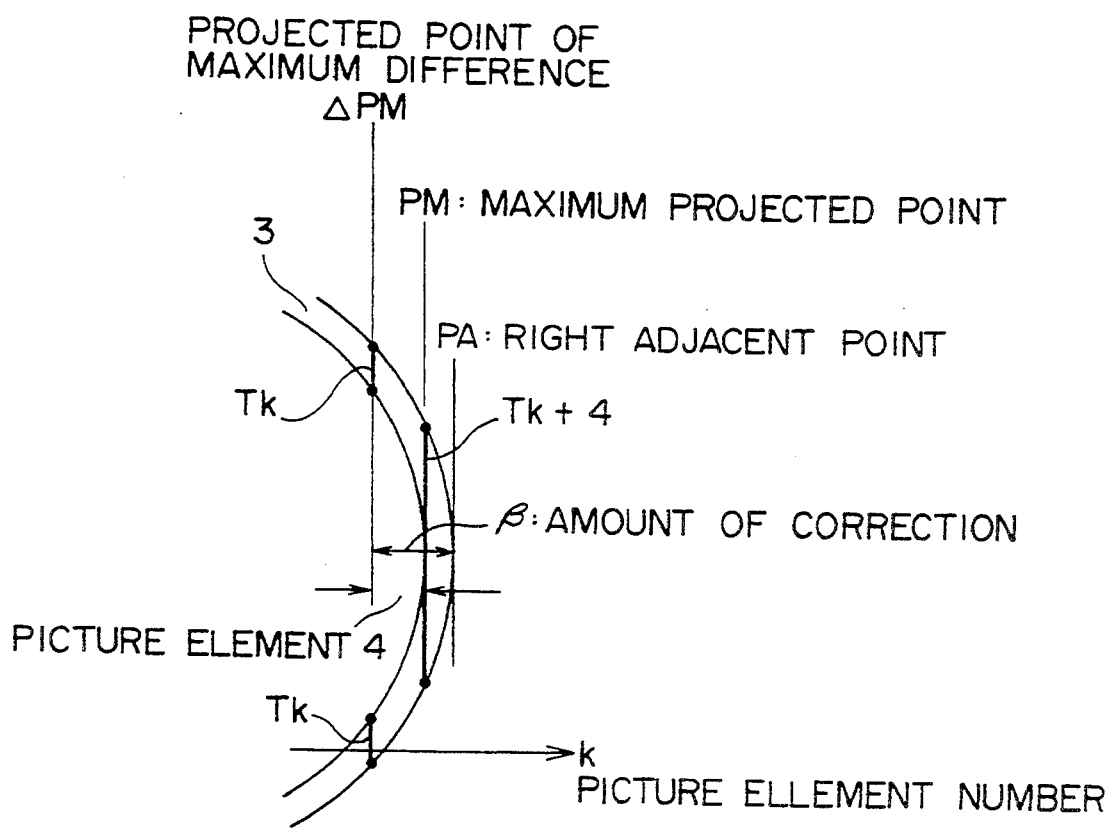
FIG. 25 is an enlarged view of FIGS. 24A to 24C.

FIG. 25 is a view enlarged around the point $\Delta$PM. In FIG. 25, PM marks the maximum projected amount in the highlighted opening. portion 3 (referred to as the maximum projection point). $\Delta$PM is a point near the maximum projection point PM and can be obtained as follows relative to the maximum projection point PM, That is, the picture element number k is sequentially assigned from the center of the test container 2 to the X direction. The number of projected picture elements is Tk at the position of the picture element number k. The difference between the Tk and the number of the projected picture elements $T_{k+4}$ at the point four picture elements apart to the right can be obtained as follows.

$$\Delta T_k = T_{k+4} - T_k$$

If thus calculated differences generate a difference projection pattern, $\Delta$PM indicating the maximum value of $\Delta T_k$ is determined to be the point four picture elements inside the maximum projection point PM.

In the present invention, the right adjacent point PA can be obtained by adding a predetermined correction value $\alpha$ to the maximum difference projection point $\Delta$ PM. According to the result, adjacent containers are isolated and the resultant coordinates determine a process area.

The maximum difference projection point $\Delta$ PM is obtained first because it can be detected as stable coordinates while the maximum projection point PM is subject to the influence of the fluctuation of the ring width of the highlighted opening portion 103 caused by the intensity of the illumination applied to the test container.

Thus, the present invention can reduce the influence of adjacent containers by detecting an adjacent point from the center to the opening of a test container by regarding the highlighted opening portions 3.

Figure 26:
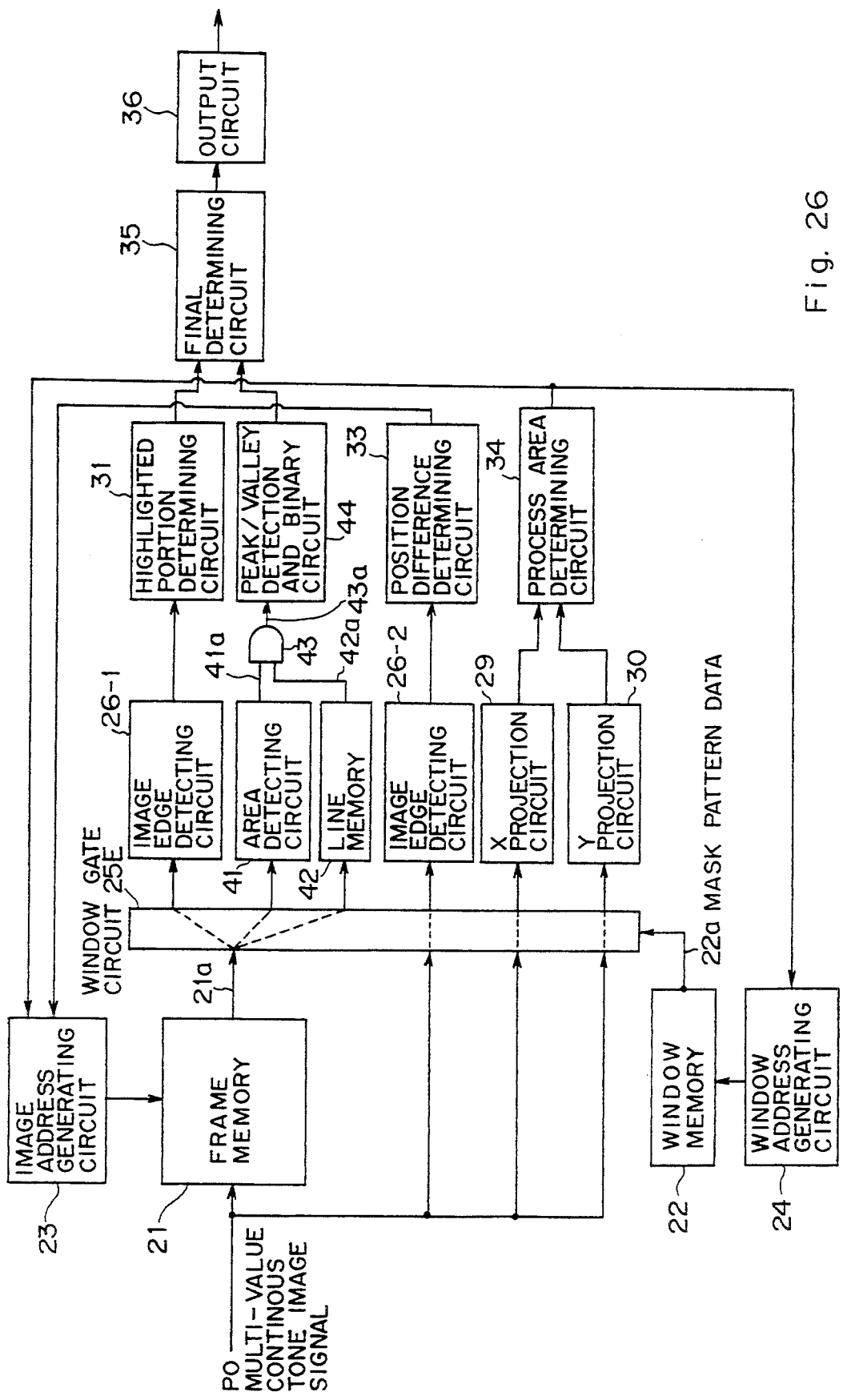
FIG. 26 is a block diagram for explaining the hardware configuration of the embodiment of the present invention.

Another embodiment of the present invention is described below by referring to FIGS. 7 and 26 through 32. FIG. 26 is a block diagram of a hardware as an embodiment of the present invention. In FIG. 26, a multi-value (8 bits, for example) continuous tone image signal PO is obtained by AD-converting the video signal provided by raster-scanning the surface of a TV camera not shown in FIG. 26. A frame memory 21 receives a multi-value continuous tone image signal PO to store them as multi-value image data; an address generating circuit 23 is provided for the frame memory; a window memory 22 stores a mask pattern for each window; an address circuit 24 is provided for the window memory; a window gate 25E masks with a mask pattern data 22a obtained from the window memory 22a multi-value continuous tone image signal PO or an image signal 21a read from the frame memory 21, and passes only the image signal PO or the image signal la for the specified window area.

Image edge detecting circuits 26-1 and 26-2 detect the edge of an image, that is, the outer edge (the point in the outer circumference) and the inner edge (the point in the inner circumference) of a ring-shaped highlighted portion. In this case, an inputted image signal is converted to the binary representation using a predetermined threshold used for detecting the position of a target image or performing the circularity test. Then, the image edge detecting circuit 26-1 and 26-2 store the rise point and the fall point coordinates of the binary signals each indicating the edge of an image in their own memories. A circuit 31 performs the circularity test on the coordinates of the points in the outer and inner circumferences detected by the image edge detecting circuit 26-1.

A circuit 33 detects the difference between the center position of an actual target image detected by the image edge detecting circuit 26-2 by applying the latest multi-value continuous tone image signal PO and the central position of a predetermined window.

An area detecting circuit 41 receives a multi-value continuous tone signal 21a through the frame memory 21 and the window gate circuit 25E, and outputs an area signal 41a as a signal for specifying an area to be scanned (that is, an area within the contour of a test container) for a defect on each of the horizontal scanning lines for the purpose of detecting a defective image.

A line memory 42 receives an image signal 21a for each of the horizontal scanning lines in synchronous with the area detecting circuit 41, and temporarily stores it.

A AND gate 43 ANDs an area signal 41a and a continuous tone image signal 42a outputted by the line memory 42 as an image signal for each of the horizontal scanning lines corresponding to an area signal 41a, and outputs a continuous tone image signal for an area to be searched for a defect (referred to as a test area continuous tone image signal).

A peak/valley detection and binary-conversion circuit 44 is an important part of the present invention and detects from an image signal 43a a defective picture element including a defective peak/valley.

An X projection circuit 29 obtains an X-direction projection pattern of a target image using a multi-value image signal PO which has passed through the window gate circuit 25E. Likewise, a Y projection circuit 30 obtains a Y-direction projection pattern of a target image. A process area determining circuit 34 determines using these output data of the projection circuits 29 and 30 the area of a test container image not adjacent to other container images.

A final determining circuit 35 receives a determination result from the peak/valley detection and binary-conversion circuit 44 to make final determination; and an output circuit 36 outputs the acceptability according to a determination signal outputted by the final determining circuit 35.

In the present invention, the area detecting circuit 41, detects the contour of a container as a test area, and the area is searched for a detect according to the equations (1), (2), (1A), and (2A) shown in FIGS. 7A and 7B.

Additional information about the multi-value continuous tone image signal PO is described below. That is, an analog video signal obtained by rescanning the image taken by a TV camera can be converted to a digital signal using an A/D converting circuit, etc. by a common method. Then, the multi-value continuous tone image signal PO is a digital signal converted by -the A/D converting circuit, etc.

Figure 27A:
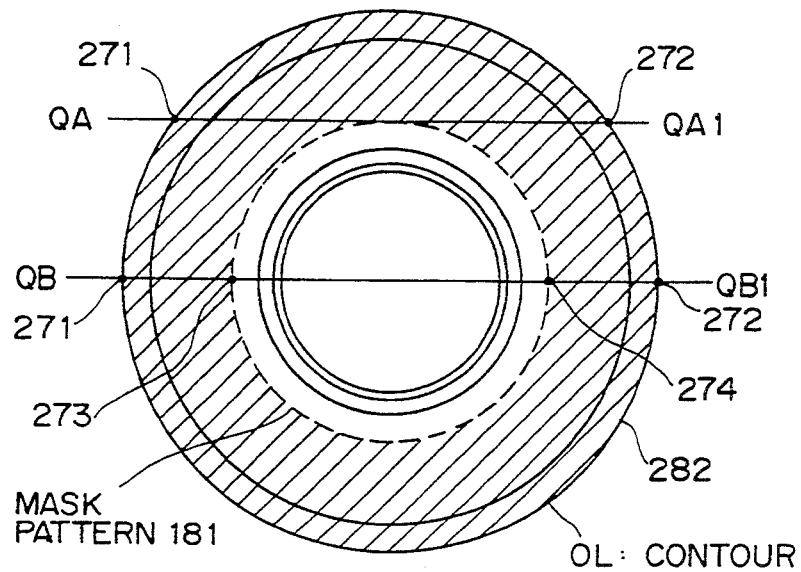
FIGS. 27A, 27B and 27C are views for explaining the operation of the area detecting circuit.
Figure 27B:
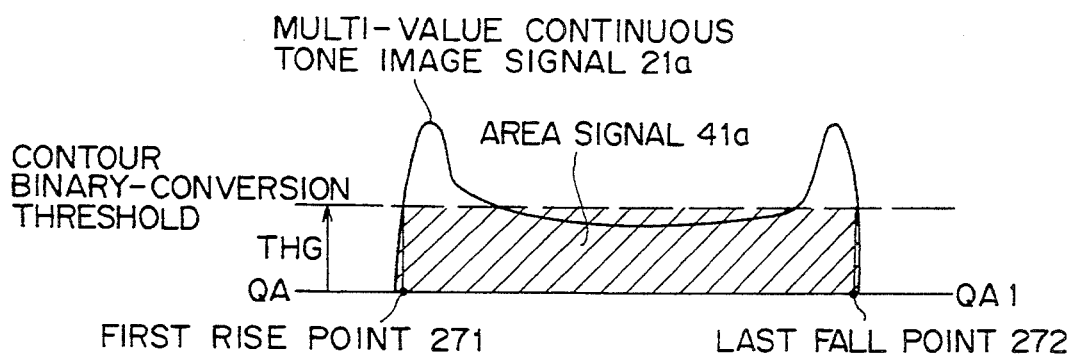
Figure 27C:
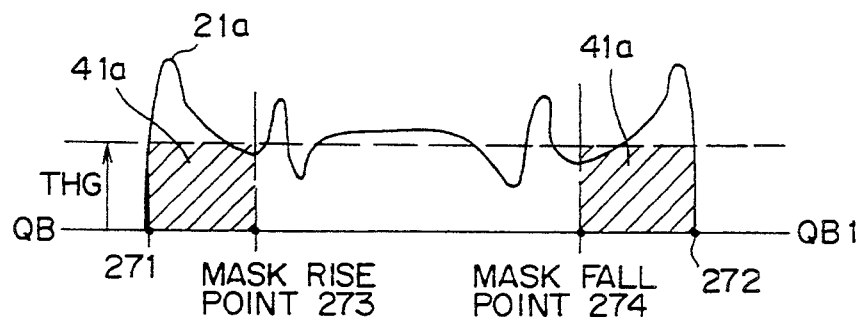

FIGS. 27A through 27C show the operation of the above described area detecting circuit 41, that is, the operation for detecting the test area (namely, the contour of a container). That is, FIG. 27A is a top view of the container 282, where OL shows the contour, the lines QA-QA1 and QB-QB-1 show scanning lines (or section), and 181 is a mask pattern. FIG. 27B indicates the relationship between the intensity carnations (continuous tone image signal) along the section QA - QA1 and the area to be tested. FIG. 27C shows the relationship between the intensity variations (continuous tone image signal) along the section QB - QB1 and the test area.

As described above, the area detecting circuit 41 receives a multi-value continuous tone image signal 21a from the frame memory 21 through the window gate circuit 25E, and converts it to a binary number using a threshold THG (referred to as a binary contour threshold for convenience) as shown in FIG. 27B. Then, the first rise point 271 and the last fall point 272 of the binary signal are detected, and the range between the these points is defined as a process range.

A signal indicating the process range, that is, the signal indicating "1" for the diagonal-shaded portion shown in FIG. 27B is outputted as the area signal 41a. The area signal 41a and the continuous tone signal 42a for one scanning line temporarily stored by the line memory 42 corresponding to the area signal 41a are ANDed through the AND gate 43 for outputting the above described continuous tone signal 43a for the test area.

Alternatively, the area signal 41a can be obtained from the window signal obtained from the mask pattern data 22a from the window memory 22 (that is, a signal indicating the area excluding the mask pattern area), or as a combination of the area signal 41a and the window signal.

The area between the points 273 and 274 shown in FIG. 27C corresponds to the area of the mask pattern 181 shown in FIG. 27A, where 273 is a mask rise point, and 274 is a mask fall point. In this example, the mask pattern 181 masks the area in which the variation of the continuous tone image signal 21a of the container bottom is anticipated to be somewhat complicated.

In this case, the window signal can be obtained as "1" in the area excluding the area between the points 273 and 274 in the mask area. The signal obtained by combining the original area signal indicating "1" only between the first rise point 271 and the last fall point and the window signal, that is, the signal indicating "1" only in the diagonal-shaded portion between the points 271 and 273 and between the points 274 and 272 shown in FIG. 27C is the area signal 41a finally outputted from the area detecting circuit 41.

The test area indicated by diagonal shaped portion as shown in FIG. 27C can be assigned the optimum number α of picture elements and the threshold THD in equations (1), (2), (1A), and (2A) shown in FIGS. 7A and 7B.

Thus, the optimum number α of picture elements according to the optical characteristics of the inner surface of a container and the threshold THD are selected by concentrically creating a number of the mask patterns 181 or the window patterns, thereby improving the efficiency in detection.

Figure 28:
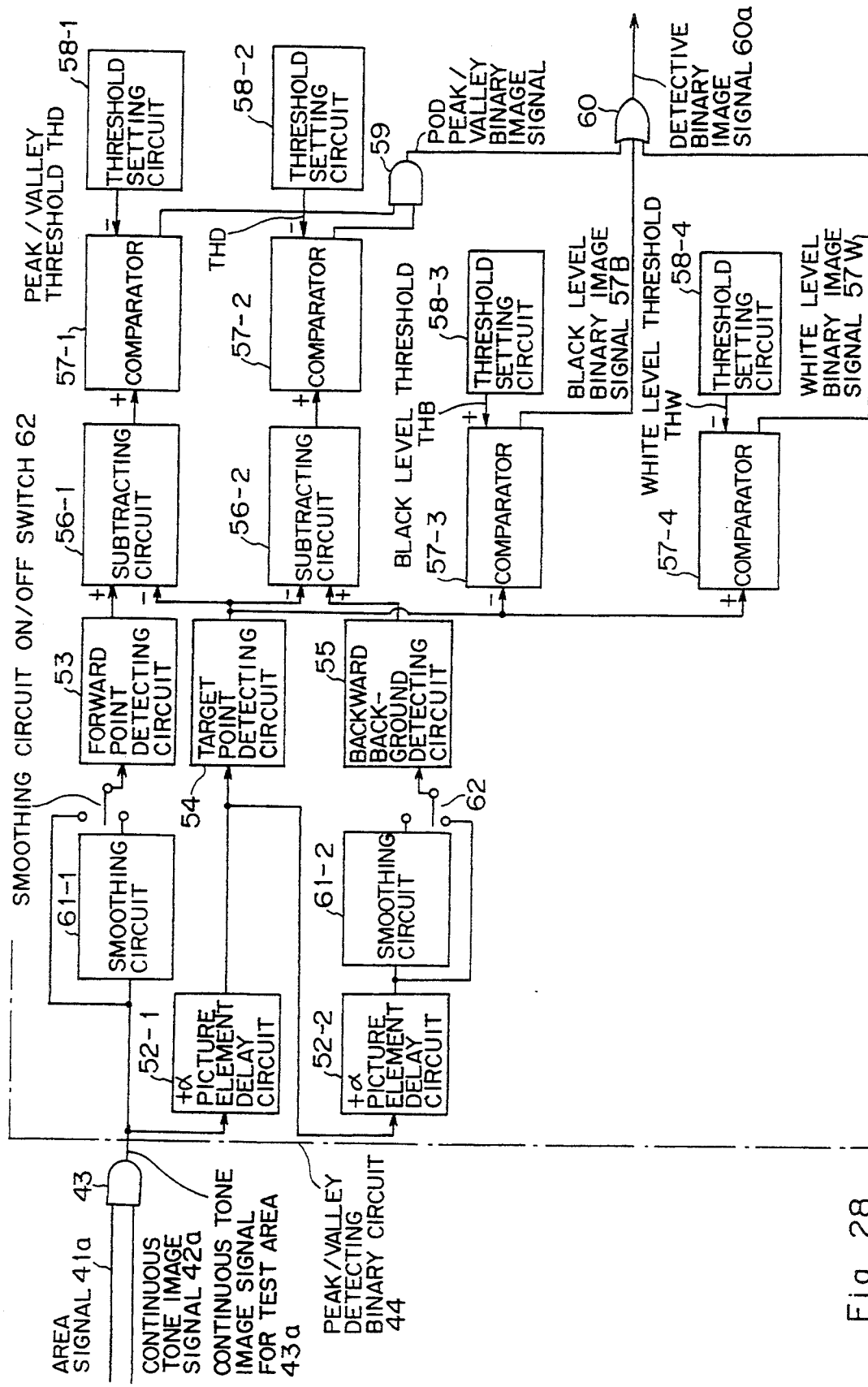
FIG. 28 is a block diagram for explaining in detail the configuration of the peak/valley detecting circuit in an embodiment of the present invention.

FIG. 28 is a block diagram of an embodiment of the detailed configuration of the peak/valley detection and binary-conversion circuit 44 shown in FIG. 26. However, with this configuration, a valley (defect) is detected. In the case of a peak (defect) detection, the subtraction of subtraction circuits 56-1 and 56-2 is inverted, or an input image signal 43a applied to the peak/valley detection and binary-conversion circuit 44 is inverted. In this case, the function of a comparator 57-3 (black level determination by a fixed binary conversion) and that of a comparator 57-4 (white level determination by a fixed binary conversion) are exchanged with each other.

Next, the function shown in FIG. 28 is explained below. FIG. 28 shows the execution of the principle shown in FIG. 26. In FIG. 28, +α picture element delay circuits 52-1 and 52-2 sequentially delay an input image signal 43a (that is, a test area continuous tone image signal outputted by the AND gate 43 shown in FIG. 26) by picture elements in the scanning direction.

Smoothing circuits 61-1 and 61-2 smooth an image signal if necessary to reduce the influence of noises; and a smoothing circuit ON/OFF switch 62 switches ON or OFF the smoothing function.

The smoothing circuit 61-1 is provided corresponding to the forward background point detecting circuit 53, and likewise, the smoothing circuit 61-2 is provided corresponding to the backward background point detecting circuit 55. For the purpose of improving the sensitivity in detecting a defect in a target point (that is, improving the function of detecting a defective picture image by a small peak/valley or small intensity variations, namely, by a small threshold value), the smoothing circuit is not provided for a target point detecting circuit 54 described later.

A forward background detecting circuit 53 receives as an original input image signal a test area continuous tone image signal 43a or a smoothed signal for it to detect a forward background point. A target point detecting circuit 54 receives an output image signal of the +α picture element delay circuit 32-1 to detect a target point. A backward background detecting circuit 35 receives an image signal outputted by the +α picture element delay circuit 52-2 or a smoothed signal for it to detect a backward background point. Each of the detecting circuits 53, 54, and 55 simultaneously latches the picture element values PO(i+α,j), PO(i,j), and PO(i−α,j) described by referring to FIG. 7 if the smoothing circuit 61-1 and 61-2 are omitted (that is, the smoothing circuit is short-circuited by the switch 62) when the delay circuits 52-1 and 52-2 are used.

When the smoothing circuits 61-1 and 61-2 are used, the above described picture element values PO(i+, j) and PO(i−,j) are replaced with the results of the following expressions (3) and (4) respectively.

$$PO(i+\alpha, j) = \{k = O\Sigma^{n-1} PO(i+\alpha+k, j)\}/n \quad (3)$$

$$PO(i-\alpha, j) = \{k = O\Sigma^{n-1} PO(i-\alpha-k, j)\}/n \quad (4)$$

That is, the smoothing circuit 61-1 replaces the picture element value of the forward background point with an average value of n forward picture element values including the picture element value PO(i+α, j) of the forward background point and those of the points beyond it. Likewise, the smoothing circuit 61-2 2 replaces the picture element value of the backward background point with an average value of n backward picture element values including the picture element value PO(i−α,j) of the backward background point and those of the points beyond it.

The average values are not calculated with the background point set as a median to prevent the picture element value PO(i,j) of a target point from being involved in calculating the average values.

An average value obtained by expression (3) or (4) can be replaced with a median in n picture element values (that is, the value at the middle point when n values are arranged in order).

Each piece of the above described image data latched by the detecting circuits 53, 54, and 55 shown in FIG. 28 are applied to the subtracting circuits 56-1 and 56-2 and the difference is calculated according to the contents of expressions (1) and (2) shown in FIG. 7. The difference is compared by comparators 57-1 and 57-2 with a peak/valley value THD each being predetermined by threshold setting circuits 58-1 and 58-2. Thus, a peak/valley binary image signal POD shown in FIG. 7 (a defective bottom in this case) can be obtained as an output from the AND gate 59 for ANDing the comparators 57-1 and 57-2.

The comparators 57-3 and 57-4 detect a defective picture element in a relatively large area. The comparator 57-3 receives image data of a target picture element outputted by the target point detecting circuit 54 which does not receive a smoothed image signal. Then, it compares the received data with a black level threshold THB determined by the threshold setting circuit 58-3, and detects and outputs a black level binary image signal 57B indicating a black level defective picture element.

Likewise, the comparator 57-4 receives data of a target picture element, compares it with a white level threshold THW determined by a threshold setting circuit 58-4, and detects and outputs a white level binary image signal 57W indicating a white level defective picture element.

An OR gate 60 ORs the signals thus detected as defective picture element detection signals including a peak/valley binary image signal POD, a black level binary image signal 57B, and a white level binary image signal 57W, and outputs a defective binary image signal 60a.

A black level defective picture element detector (the comparator 57-3, etc.) and a white level defective picture element detector (the comparator 57-4, etc.) operate concurrently with the peak/valley detector/binary-converter (an AND gate 59, etc.). These units separately test an image, and the results are finally put together and outputted as final determination.

Next, an image scanning method is explained below. FIG. 7A shows the continuous tone of an image at a section Q-Q1. In expressions (1), (2), (1A), and (2A), α means the number of picture elements, and is a parameter indicating the frequency of an image signal at a defective portion (that is, the width of a peak or a valley). However, as shown in FIG. 7A, continuous tone image signals for the inner surface of a non-defective container complexly comprise various frequency components. Therefore, the inner surface of a container must be divided if necessary and each of them must be assigned an optimum parameter.

However, the intensity variations in background picture elements can be simplified by appropriately determining the scanning direction of the image, thereby improving the detection precision.

Figure 29A:
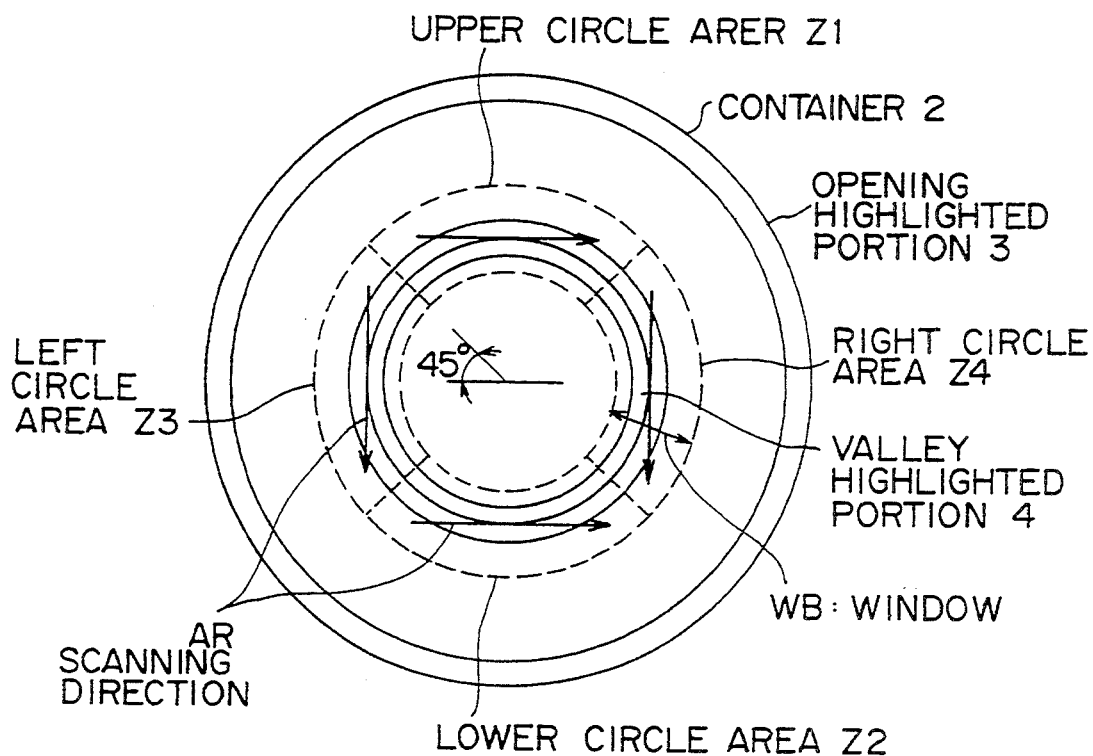
FIGS. 29A to 29C show the embodiment of the screen scanning method of the present invention.
Figure 29B:
Figure 29C:
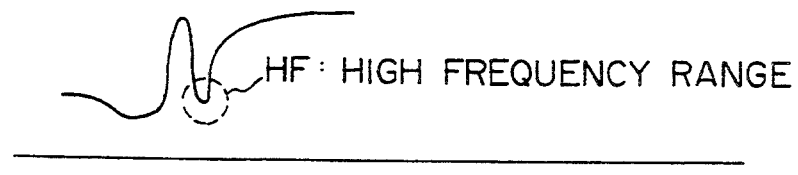

FIGS. 29A to 29C are views for explaining an embodiment of an image scanning method, where a window WB is divided into the following four areas each being selected as a target area to be searched for a defect; Z1, Z2, Z3, and Z4 are respectively upper circle area, lower circle area, left circle area, and right circle area. That is, in FIG. 29A, the highlighted bottom portion 4 having complicated intensity variations in the container 2 is selected through the window WB and a peak is detected and binary-converted. If the intensity variations are checked horizontally, for example, in the left circle area Z3 of the window WB, the intensity variations occur at a high frequency in portions such as "HF" shown in FIG. 29C, thereby affecting the detection sensitivity. However, if the left circle area Z3 of FIG. 29A is scanned in the direction indicated by the arrow AR, intensity variations can be obtained at a low frequency as the background as shown in FIG. 29B, while the defective portions are detected at a sufficiently high frequency, thereby improving the detective precision.

Figure 30:
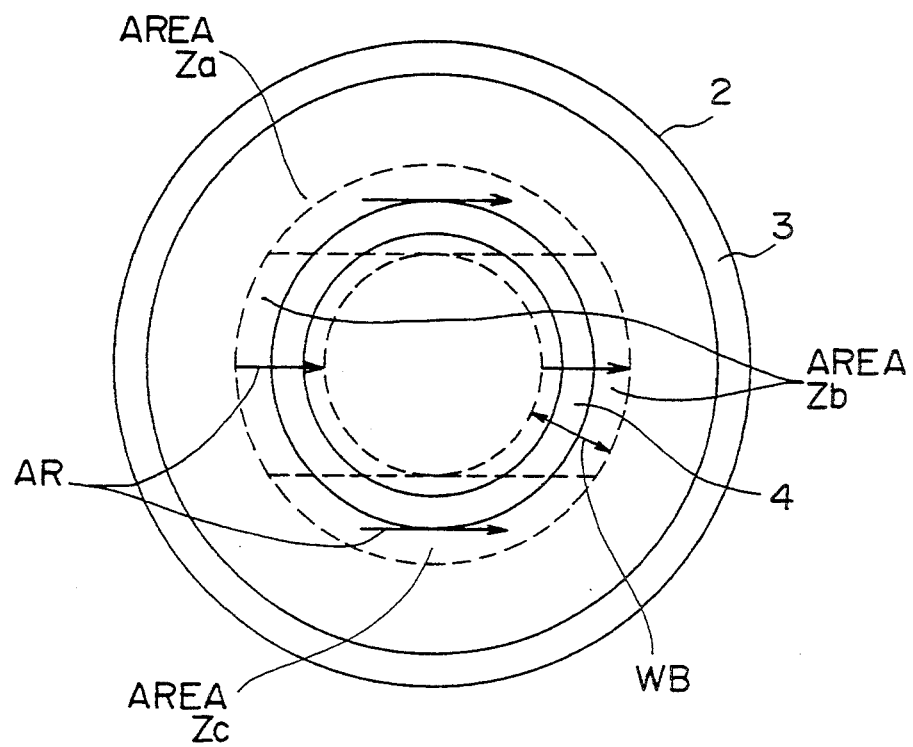
FIG. 30 shows the embodiment of the screen scanning method of the present invention.

FIG. 30 is a view for explaining an embodiment of a simple picture scanning method. In FIG. 30, an image is scanned horizontally as indicated by the arrow AR, and the window WB is divided into three areas Za, Zb, and ZG. In this case, a threshold for detecting a peak/valley in the areas Za and Zc and a threshold for detecting a peak/valley in the area Zb are determined separately to perform an optimum detection according to the frequency of the background intensity.

In this case, the defect detection sensitivity is low in the area Zb. However, the detection sensitivity in the areas Za and Zc can be enhanced.

Figure 31:
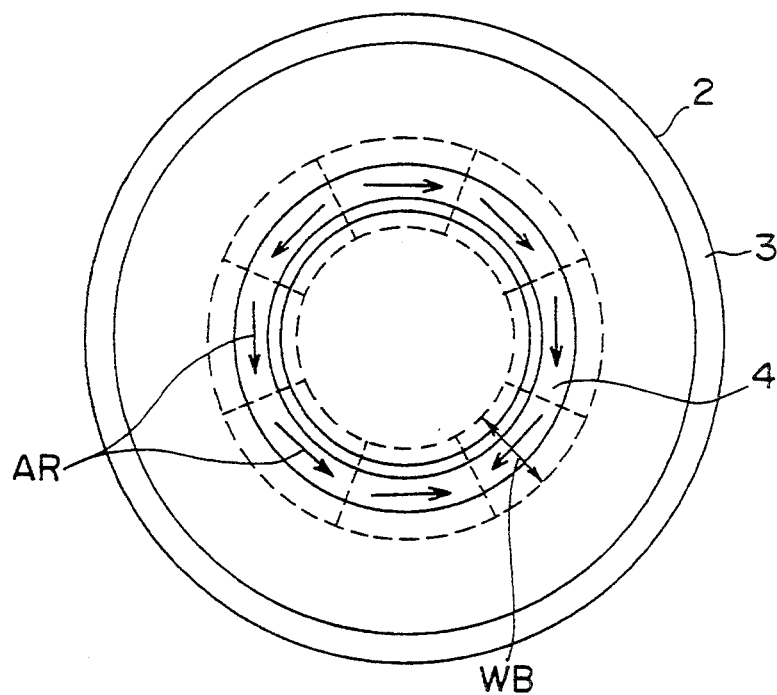
FIG. 31 shows the embodiment of the screen scanning method of the present invention.

FIG. 31 shows a variation of the embodiment shown in FIG. 29A. In FIG. 29A, the scanning area is radially and equally divided into four fan-shaped areas. By contrast, in FIG. 31, the area is equally divided into eight fan-shaped areas, and an optimum scanning direction AR is assigned respectively, thereby improving the detection sensitivity much more than the case in FIG. 29A.

Figure 32A:
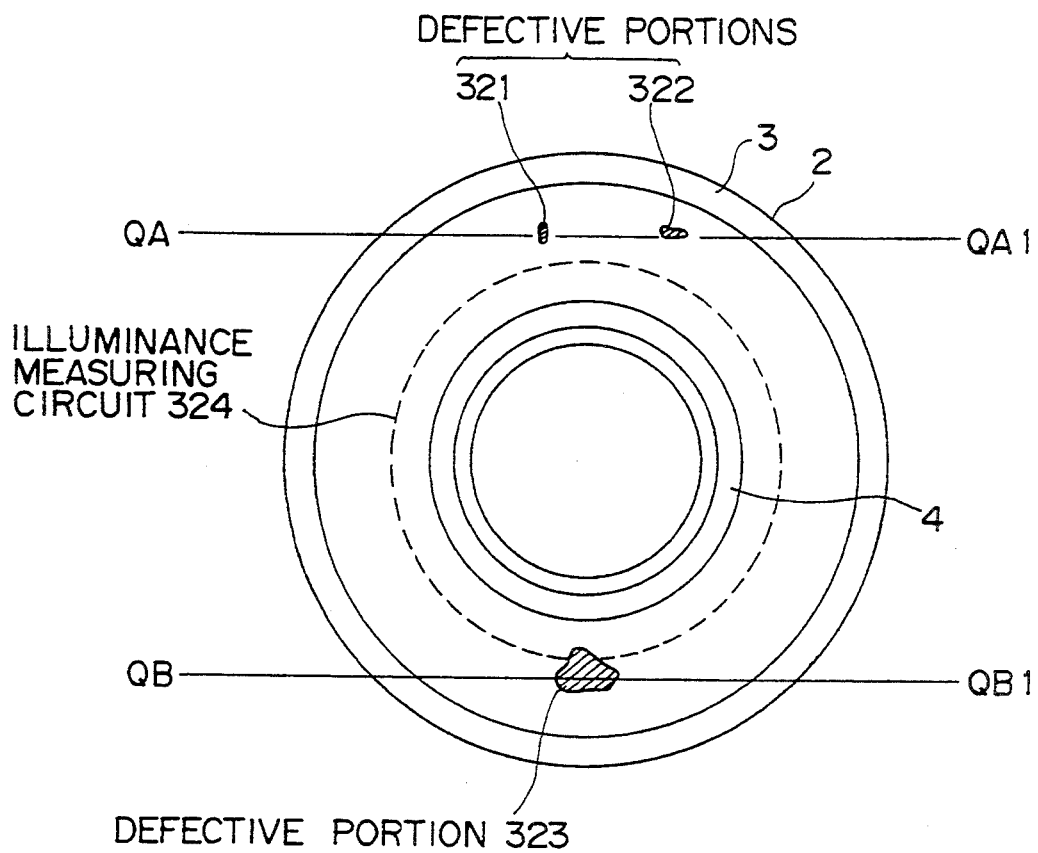
FIGS. 32A to 32C show the relationship between the defect detecting method of the present invention and the shape of the defective portion.
Figure 32B:
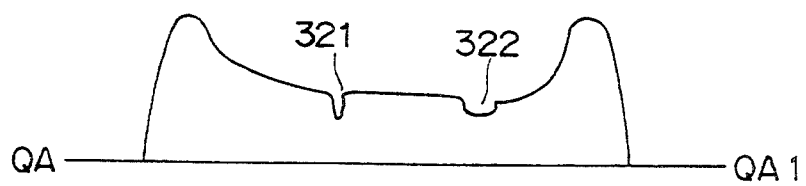
Figure 32C:
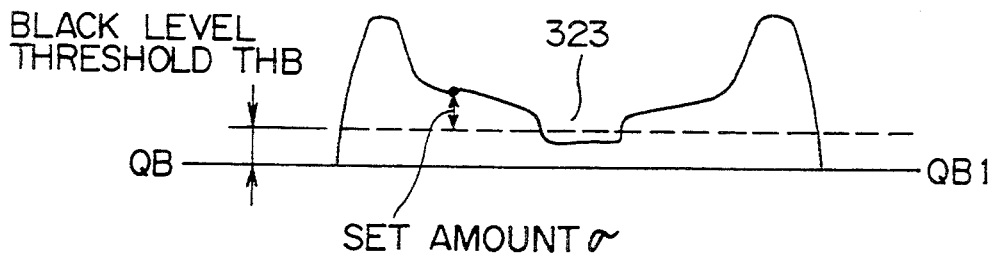

FIGS. 32A to 32C are views for explaining the relationship between a defect detecting method based on the present invention and the shape of a defective portion. In FIG. 32A, defective portions 321–323 is detected in the image of the container 2. Figure 32B shows the intensity variations in the scanning line QA-QA1 shown in FIG. 32A. Defective oval portions 321 an 322 show different intensity frequencies depending on the direction of their longer diameter. Therefore, the defect detection sensitivity can be improved by picking up the amount corresponding to the number a of picture elements in expressions (1) and (2) several times and repeating-the check.

FIG. 32C shows the intensity variations in the scanning line QB-QB1 shown in FIG. 32A. A defective portion 323 in this section is relatively large, and the variation in the continuous image signal is represented at a low frequency but sufficient to detect a black spot in contrast with its background.

Since the defective portion 323 must be detected at a low frequency, it cannot be successfully detected unless the number a of the above described picture elements is unpractically large enough in the valley-detection and binary-conversion process. In such a case, using the fixed binary conversion method shown in FIG. 28, a defective portion 323 is isolated and detected as a black level as shown in FIG. 32C by setting a black level threshold THB by the threshold setting circuit 58-3 shown in FIG. 28, thereby supplementing the detective sensitivity in the valley-detection and binary-conversion process.

A black-level threshold THB can be determined by, for example, obtaining an average value of picture element intensity data of a circumference (an illuminating measurement circle) such as a circumference 324 shown in FIG. 32A, and subtracting a predetermined amount $\alpha$ from the average value.

The present invention performs a circularity test on the highlighted portions of the inner surface of a container. As a result, not only the deformation of a container or an abnormal concave in it, but the dust attracted to a highlighted portion of it can be detected with a high detective precision. Accordingly, a large window area can be scanned at a time (that is, the number of windows can be reduced) by parallel performing the circularity test and the black/white spot test by the conventional defect test method, thereby speeding up the whole process.

The present invention performs a circularity test on a highlighted portion of the inner surface of a container after specifying the position of the container by obtaining the coordinates of the middle point between the first rise point and the last fall point in the scanning line of the binary image of the highlighted opening portion of a container. As a result, not only the deformation of a container (can) or an abnormal concave in it, but the dust attracted to a highlighted portion of it can be detected with a high detective precision. Accordingly, a large window area can be scanned at a time (that is, the number of windows can be reduced) by parallelly performing the circularity test and the black/white spot test by the conventional defect test method, thereby speeding up the whole process.

The present invention specifies the position of the container by obtaining the coordinates of the middle point between the first rise point and the last fall point in the scanning line of the binary image of the highlighted opening portion of a container.

Then, it performs a circularity test on a highlighted portion of an inner surface of a container after obtaining the projected amount of a binary image of the highlighted opening portion (the projection being made in the direction perpendicular to the container adjacent direction), searching from the inner side to the outer side of a container for the difference in the projected amount, detecting adjacent points on a predetermined condition, and isolating a target area from the area containing adjacent containers. As a result, not only the deformation of a container or an abnormal concave in it, but the dust attracted to a highlighted portion of it can be detected with a high detective precision. Accordingly, a large window area can be scanned at a time (that is, the number of windows can be reduced) by parallelly performing the circularity test and the black/- white spot test by the conventional defect test method, thereby speeding up the whole process.

The cylindrical container's inner surface tester illuminates from above in the axis direction of a container by a ring illumination 1 the inner surface of an axis-symmetrical cylindrical container 2. A TV camera picks up the illuminated area of the cylindrical container 2 from above in the axis direction. Then, the picked-up image is analyzed to determine a black or white spot inside the cylindrical container 2.

The cylindrical container's inside surface tester comprises a defective peak/valley determiner (for example, an antecedent of an AND gate in a peak/valley detection and binary-conversion circuit 44), an image test area divider, and a value changer.

The defective peak/valley determiner determines that a target picture element is defective if two differences obtained by subtracting the value PO(i,j) of a target picture element in the same picture element scanning line for a continuous tone image signal 43a which is obtained by scanning the above described picked-up image from the values PO(i+α, j) and PO(i−α, j) of two background picture elements (hereinafter referred to as a forward background picture element and a backward background picture element respectively) a predetermined number of picture elements (hereinafter referred to as α picture elements) backward or forward of the target picture element indicate the same polarity, if an absolute value of one of the above described two differences is larger than a predetermined first threshold (THD, for example) corresponding to the polarity, and if the other absolute value is larger than a predetermined second threshold (THD, for example).

The divider divides (into Z1-Z4, Za-Zc, etc.) the test area of a target image of the defective peak/valley determiner according to the optical features of a cylindrical container's inner surface illuminated by the above described illuminator.

The value changer changes at least one value among the number of the above described α picture elements, the first threshold, and the second threshold.

The cylindrical container's inner surface tester further comprises a unit for repeating the process performed by the defective peak/valley determiner by changing the number of α picture elements for one of the above described test areas.

The cylindrical container's inner surface tester further comprises a black level defect determiner (a comparator 57-3, etc.) for determining a defective picture element whose continuous tone image signal 43a has a value smaller than a black level threshold THB, a third threshold predetermined for each test area.

The cylindrical container's inner surface tester further comprises a white level defect determiner (a comparator 57-4, etc.) for determining a defective picture element whose continuous tone image signal 43a has a value larger than a white level threshold THW, a fourth threshold predetermined for each test area.

The cylindrical container's inner surface tester further comprises a unit for obtaining a complement of 1 or 2 for the continuous tone image signal 43a to generate an inverted continuous tone image signal, converting the signal to the continuous tone image signal 43a, and providing it for the defective peak/valley determiner, thereby detecting a picture element having a defective peak/valley without inverting the above described polarity.

The cylindrical container's inner surface tester further comprises a unit for obtaining a complement of 1 or 2 for the continuous tone image signal 43a to generate an inverted continuous tone image signal, converting the signal to the continuous tone image signal 43a, and providing it for the black level defect determiner, thereby detecting a picture element having a white level defect through the black level defect determiner.

The cylindrical container's inner surface tester further comprises a unit for selecting for each test area the direction AR which allows the lowest possible frequency in the variation of a continuous tone image signal among a plurality of predetermined image scanning directions such as horizontal, vertical and oblique directions.

The cylindrical container's inner surface tester further comprises a smoothing circuit 61-1 for outputting as the value of the above described forward background picture element an average value of the values of picture elements in a section comprising a first predetermined number (n, for example) of picture elements containing the above described forward background picture element in the above described scanning line, and a smoothing circuit 61-2 outputting as the value of the above described backward background picture element an average value of the values of picture elements in a section comprising a second predetermined number (n, for example) of picture elements containing the above described forward background picture element in the above described scanning line.

Since the cylindrical container inner surface tester comprises the above described two units which output a median of the values of picture elements in a corresponding section instead of the above described average value, it can correctly detect a defect even though uneven illuminance is caused by highlighted portions illuminated by an illuminator inside a cylindrical container.

Figure 33:
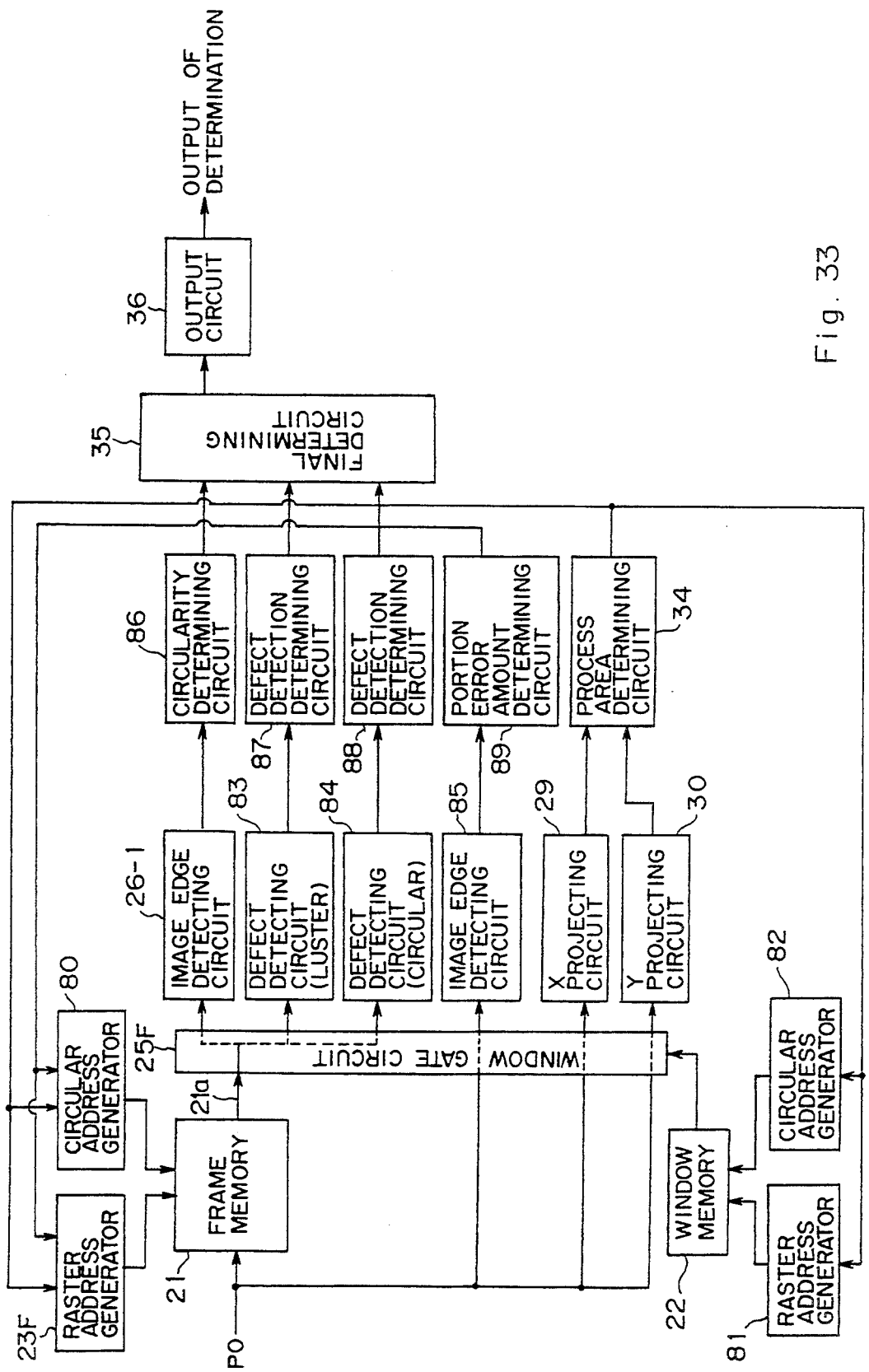
FIG. 33 is a block diagram of the hardware configuration of an embodiment of the present invention.

Next, FIG. 33 is the block diagram of the hardware of the other embodiment of the present invention. In FIG. 33, a continuous tone image signal PO consisting of 8 bits, for example, is obtained by A/D converting a video signal generated by raster-scanning the screen of a TV camera (not shown in FIG. 33); a frame memory 21 receives the multi-value continuous tone image signal PO and stores it as multi-value screen data; a raster address generator 23 generates a raster address for the frame memory; a circular address generator 80 generates an address for the frame memory 21 to circularly scan an image at; a window memory 22 stores a ring mask patttern for each window as shown in FIG. 2B; a raster address generator 81 generates a raster address for the window memory 22 in the same way as that performed by the generator 23F; likewise, a circular address generator 82 generates an address for the window memory 22 to circularly scan an image at. With this configuration, the generation of raster addresses and circular addresses can be switched by switching from the generators 23F and 81 to 80 and 82 or vice versa.

A window gate circuit 25F masks a multi-value continuous tone signal PO or an image signal 21a read from the frame memory 21 with the mask pattern data from the window memory 22, and passes an image signal PO or an image signal 21a read from the frame memory 21 in the specified window area only.

An image edge detecting circuit 26-1 has a function of detecting the edge of an image, that is, the outermost points (the points in the outer circumference) and the innermost points (the points in the inner circumference) of the highlighted ring portion. The inputted image signal is converted to a binary representation according to a predetermined threshold used for detecting the position of a target image and testing the circularity, and the coordinates of the rise point and the fall point of the binary signal indicating the image edge are stored in the memory of the image edge detecting circuit. A circuit 86 tests the circularity of a test object according to the coordinates of the points on the outer or the inner circumference detected by the image edge detecting circuit 26-1.

A defect detecting circuit 83 receives through the window gate circuit 25F the image signal 21a read from the frame memory 21 by raster-scanning the image in the frame memory 21, and detects picture elements indicating black spots, etc. A defect detection determining circuit 87 sums up the detected picture elements indicating a defect and determines whether a defect exists.

A defect detecting circuit 84 receives through the window gate circuit 25F the image signal 21a read from the frame memory 21 by circularly scanning the image in the frame memory 21, and detects a picture element indicating a defective concave. A defect detection determining circuit 88 sums up the picture elements indicating a defect and determines whether a defect exists. A circuit 35-1 receives the determination results from the circularity determining circuit 86 and the defect detection determining circuits 87 and 88, and obtains the overall determination, and an output circuit 20 outputs a positive or negative defect determination result according to the output determination signal from the overall determination circuit 35-1.

Next, an X projecting circuit 9 obtains an X-direction projecting pattern for a target image using the latest multi-value signal PO passing through the window gate circuit 25F. Likewise, a Y projecting circuit obtains a Y-direction projecting pattern for a target image. A circuit 34 obtains the area of the test container image not adjacent to other container images according to the data outputted by the two projecting circuits 29 and 30.

That is, when a cylindrical container to be tested passes through a predetermined point, a static image of the test container can be captured from above the container using a strobe light or an exposure controlled by a shutter. During the capture operation, the image is transmitted to the X projecting circuit 29 and the Y projecting circuit 30 so as to extract the characteristics of the projected pattern. When a fixed binary image is projected, the projecting circuits 29 and 30 have a function of converting to the binary representation.

Figure 34:
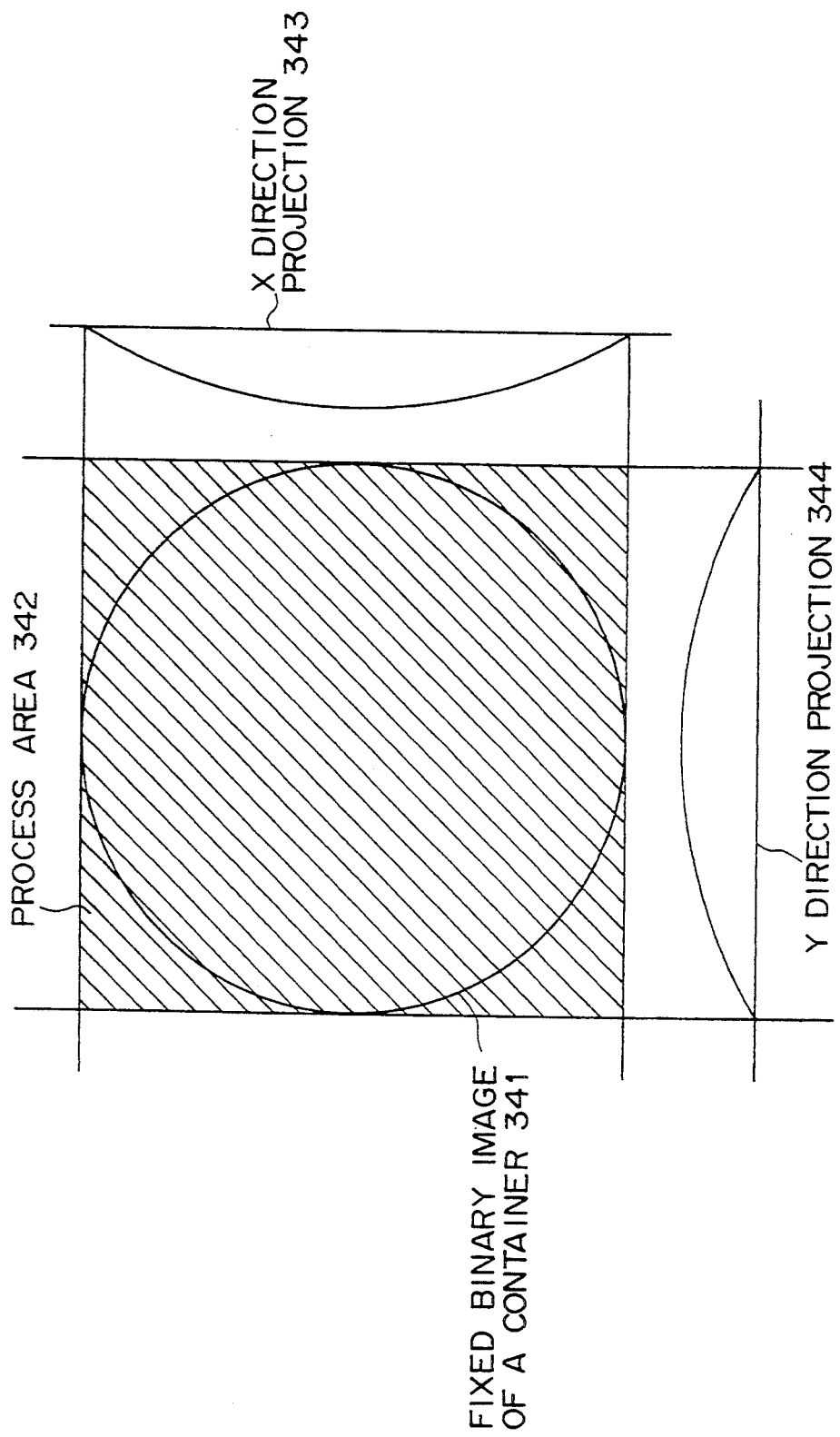
FIG. 34 shows a method of determining the process area for a container.

FIG. 34 shows a method of detecting the bounding rectangle of the container (that is, the process area indicated by diagonal shaded according to the amount of the X-direction projection 343 and the Y-direction projection 344 using the fixed binary image 341 of the container. If containers are carried adjacently on a conveyor, the process area 342 is determined after a process area separation determination circuit 34 separates adjacent containers.

Next, an image edge detecting circuit 85 and a position error amount determining circuit 89 generate a window at a correct position relative to the target image.

Figure 35:
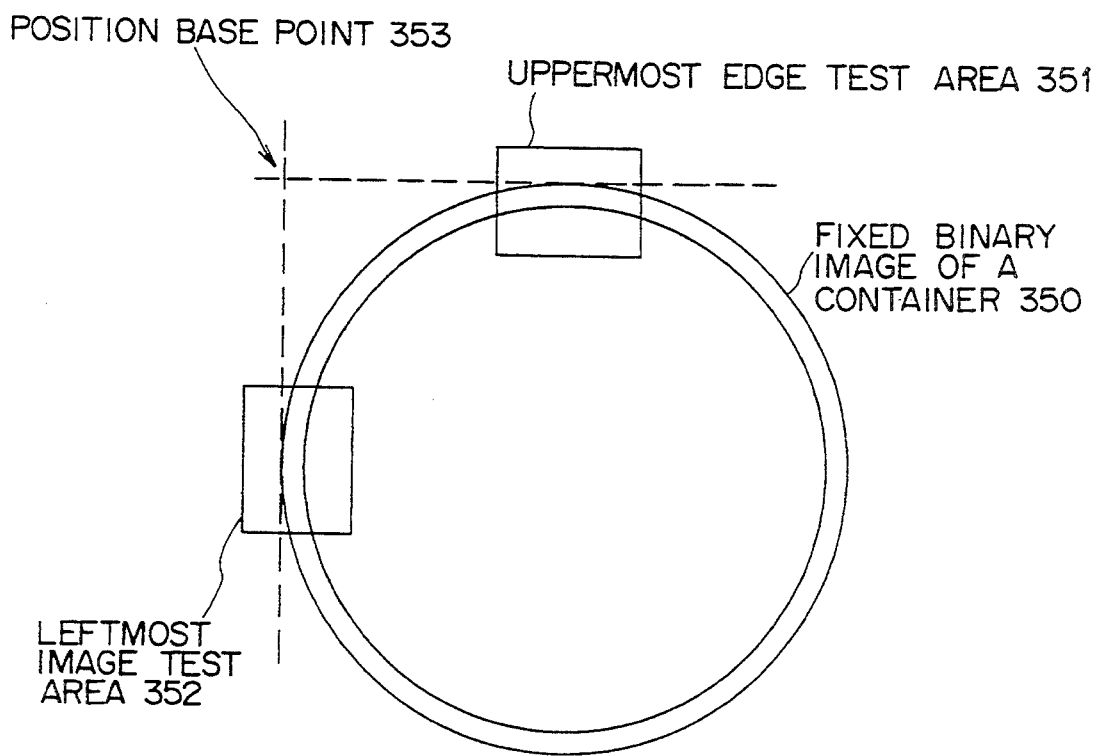
FIG. 35 shows a method of detecting the error in the position of a container.

FIG. 35 shows the operation of the image edge detecting circuit 85. The edge detecting circuit 85 receives the latest multi-value continuous tone image signal PO during the operation of the above described projecting circuits 29 and 30, and generates a fixed binary image 350 of a bottom highlighted portion so that the center of the target image can be easily detected. However, the threshold used in this process is generally different from that used by the image edge detecting circuit 26-1.

Then, the coordinates of the edges in a predetermined area for the fixed binary image 350 (in this example, the uppermost edge in the uppermost edge test area 351 and the leftmost edge in the leftmost edge test area 352), that is, the coordinates of the position base point 353 are detected.

The position error amount determining circuit 89 compares the coordinates of the position base point 353 with predetermined base coordinates, and detects the difference between the center position of the currently detected target image and the center position of the predetermined window.

Each of the processes performed by the image edge detecting circuit 26-1, the defect detecting circuit 83, the image edge detecting circuit 85, the X projecting circuit 29, and the Y projecting circuit 30, but not by the defect detecting circuit 84, is performed using the raster address generators 23F and 81. Then, control is transferred to the circular address generators 80 and 82 to generate a circular address and operate the defect detecting circuit 84.

Figure 1A:
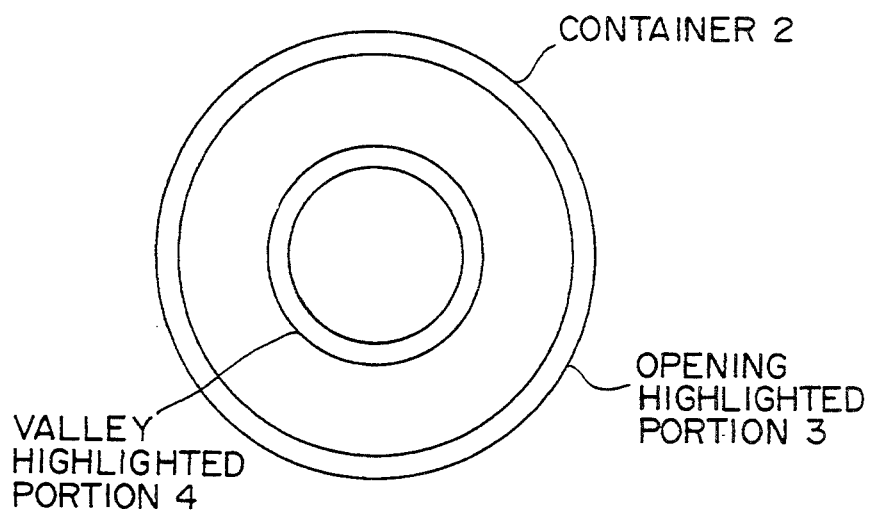
FIGS. 1A and 1B show the highlighted portion inside a container.
Figure 1B:
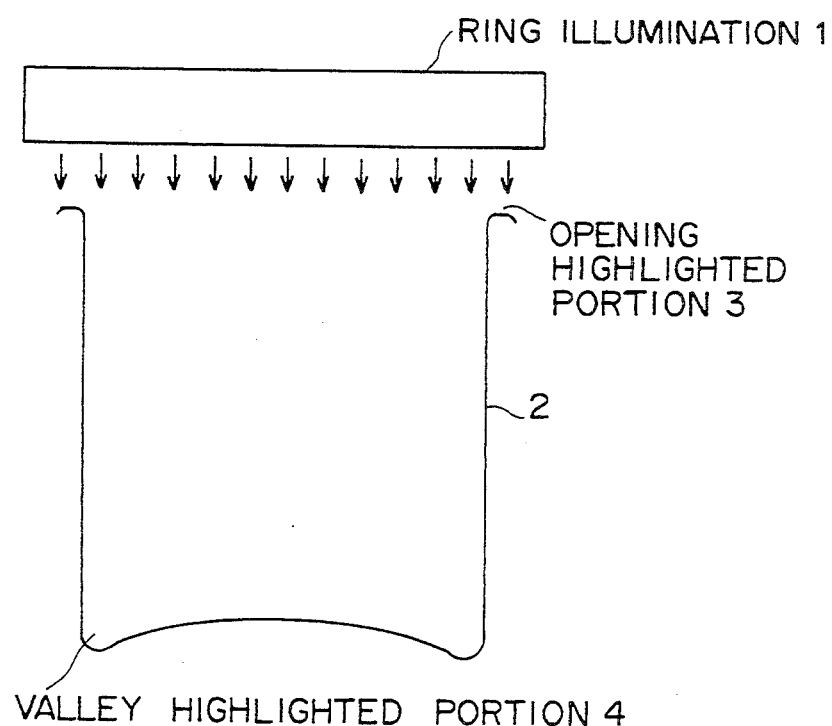
Figure 36:
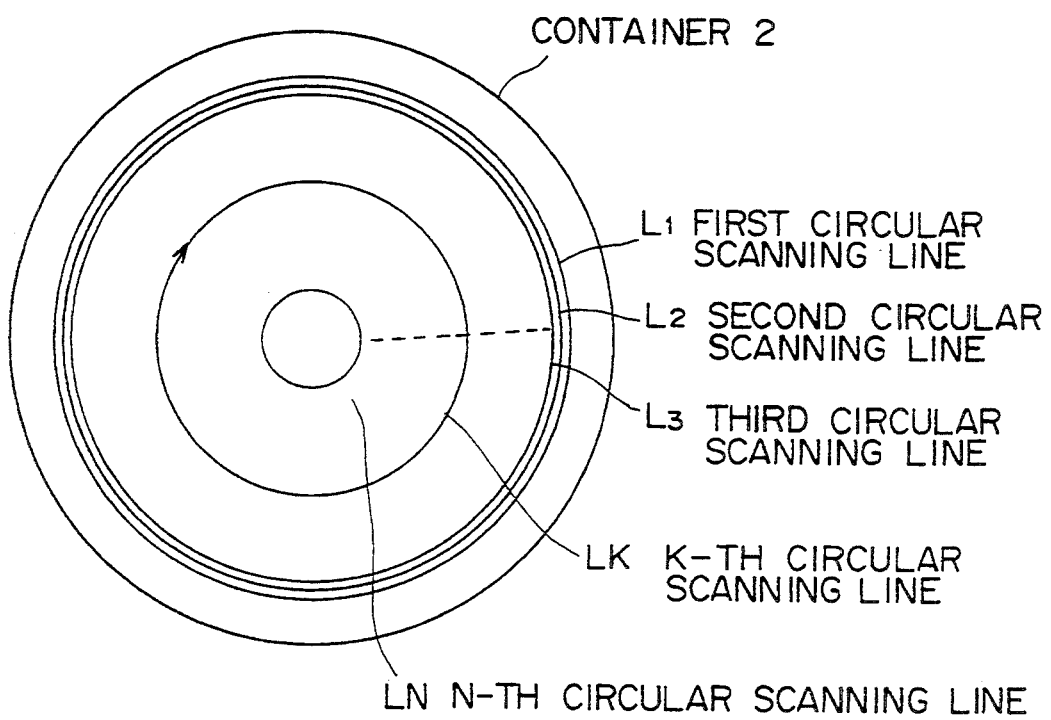
FIG. 36 shows a method of generating a circular address in the present invention.

FIG. 36 shows the method of generating a circular address. In this example, the concentric ring scanning lines (circular scanning lines) L (L1-Ln) are generated for searching the side of the container 2, that is, the image area between the opening highlighted portion 3 and the bottom highlighted portion 4 shown in FIGS. 1A and 1B, at intervals of one or more picture element (the interval is determined depending on the size of a defective concave to be detected). The image is circularly scanned clockwise and sequentially for each scanning line L from L1, L2, . . . Lk, . . . Ln with the scanning lines switched one after another. As described later in FIG. 40, circular addresses are generated such that the X and Y coordinates of target picture elements arranged at every two or more picture elements are specified sequentially in the order of the scanning operation.

Instead of the above described concentric circular scanning lines, the circular scanning lines can be a spiral scanning line in which the scanning radius changes sequentially over each cycle (in this case, the radius gets smaller).

Figure 37A:
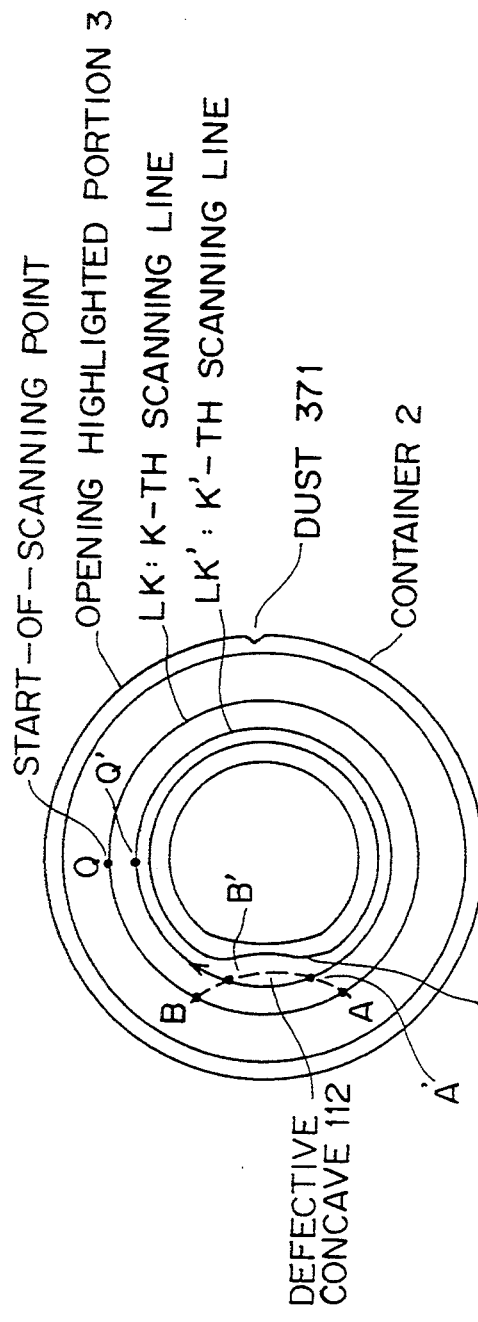
FIGS. 37A to 37B show an example of an image of a container having a concave portion.
Figure 37B:
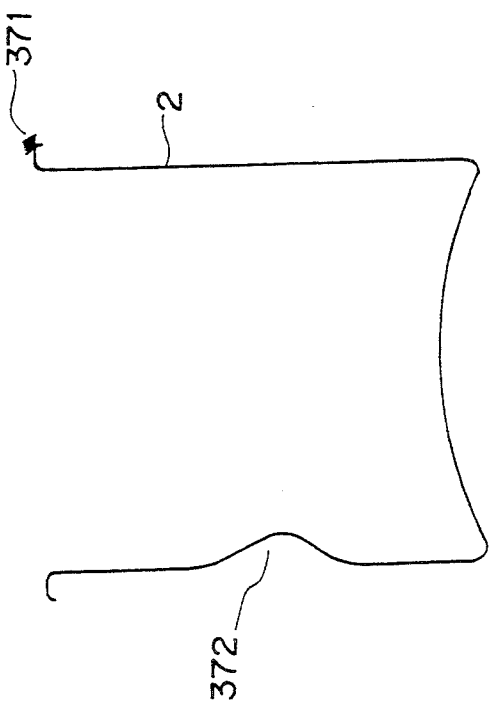

FIGS. 37A and 37B show an example of a continuous tone image which indicates that the side of the container 2 shown in FIG. 27B has a defective concave 372. In this case, a defective concave 372 exists between A and B on the k-th scanning line Lk, and between A' and B' on the scanning line Lk' of the circular scanning lines. Points Q and Q' indicate a start-of-scanning point on the circular scanning lines.

Figure 38:
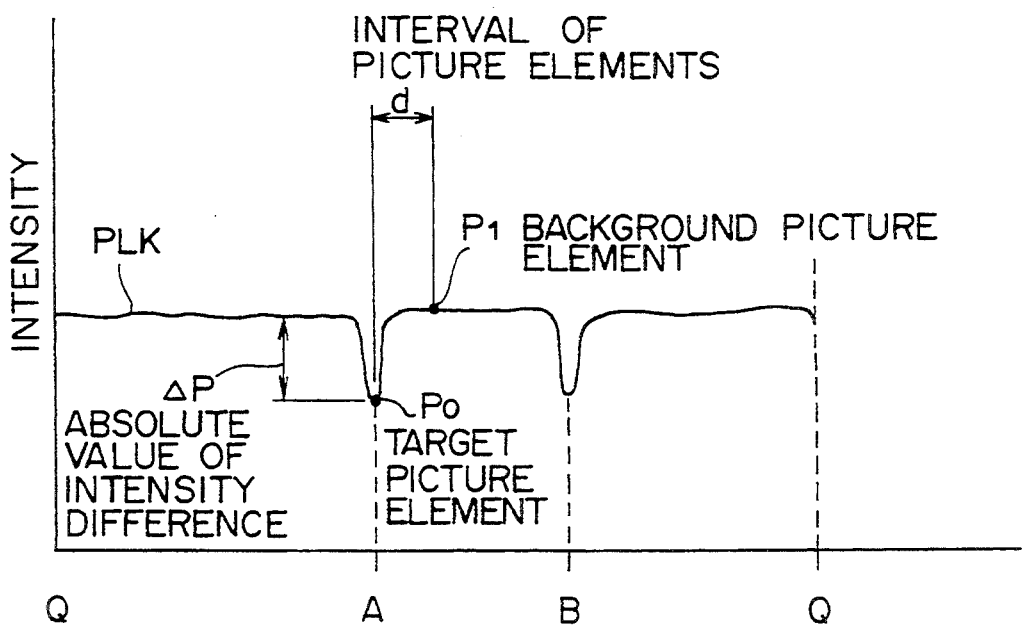
FIG. 38 shows an embodiment of the intensity variations on a scanning line, and shows the principle of the defect detecting circuit based on the circular method.

FIG. 38 shows a view for explaining the principle of the defect detecting circuit 84 of the circular method shown in FIG. 33. PLk shown in FIG. 38 shows an example of intensity variations of the image data on the k-th scanning line Lk. The characters Q, A, and B on the horizontal axis shown in FIG. 38 corresponds to the characters shown in FIG. 37A. P0 indicates a target picture element and its value, and P1 indicates a background picture element and its value. The background picture element is a predetermined number d of picture elements away from the target picture element.

The defect detecting circuit 84 compares the threshold THP predetermined for the window containing the k-th scanning line Lk with the absolute value of the difference between the above described picture element values P0 and P1 calculated as follows.

$$\Delta P = \|P0-P1\|$$

If $\Delta IP > THP$, it is determined that the target picture element P0 indicates a defective inner surface such as a defective concave, etc.

Figure 39:
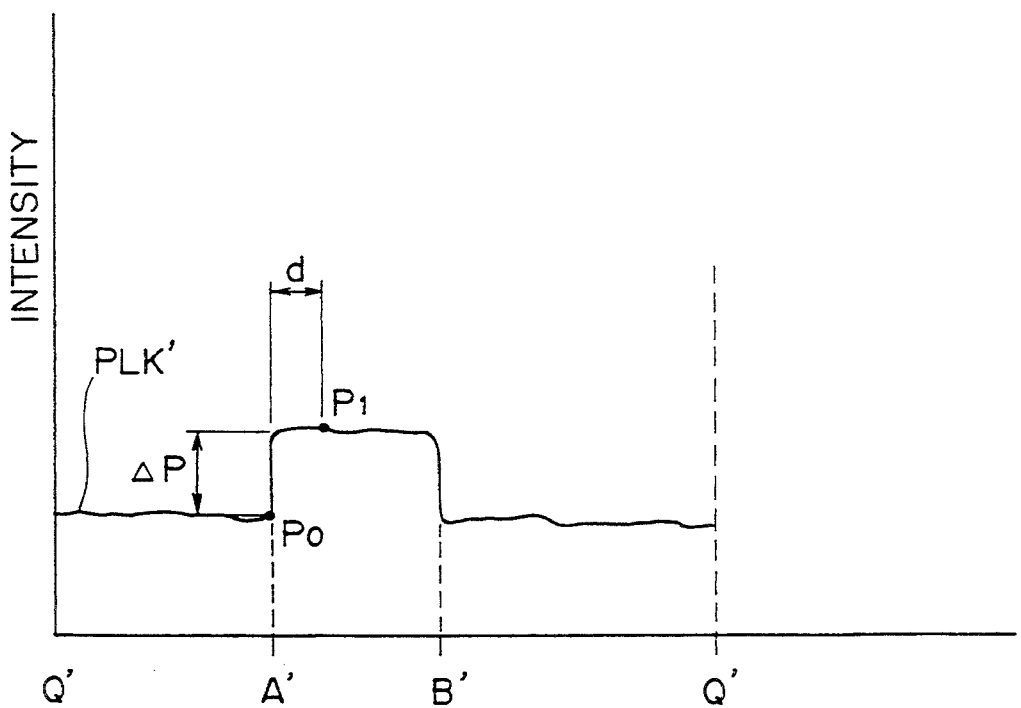
FIG. 39 shows another embodiment of the intensity variations on the scanning line, and shows the principle of the defect detecting circuit based on the circular method.

FIG. 39 shows another view for explaining the principle of the defect detecting circuit 84. PLk' in FIG. 39 shows an example of the intensity variations of the picture element data on the k-th scanning line Lk'. The characters Q', A', and B' on the horizontal axis shown in FIG. 39 correspond to the characters shown in FIG. 37A. The k'-th scanning line Lk' shown in FIG. 37A runs through the low intensity portion existing along outside the bottom highlighted portion 4. If a defective concave exists on this portion, the defective concave is highlighted as shown in FIG. 39, and the sign for the intensity difference P0−P1 is inverted from that shown in FIG. 38. However, as shown in FIG. 38, the defect detecting circuit 84 shown in FIG. 39 compares the threshold THP predetermined for the window containing the k'th scanning line Lk' with the absolute value of the difference in intensity variation obtained as follows.

$$\Delta P = \|P0-P1\|$$

If $\Delta P > THP$, it is determined that the target picture element P0 indicates a defective inner surface such as a defective concave, etc.

Figure 40:
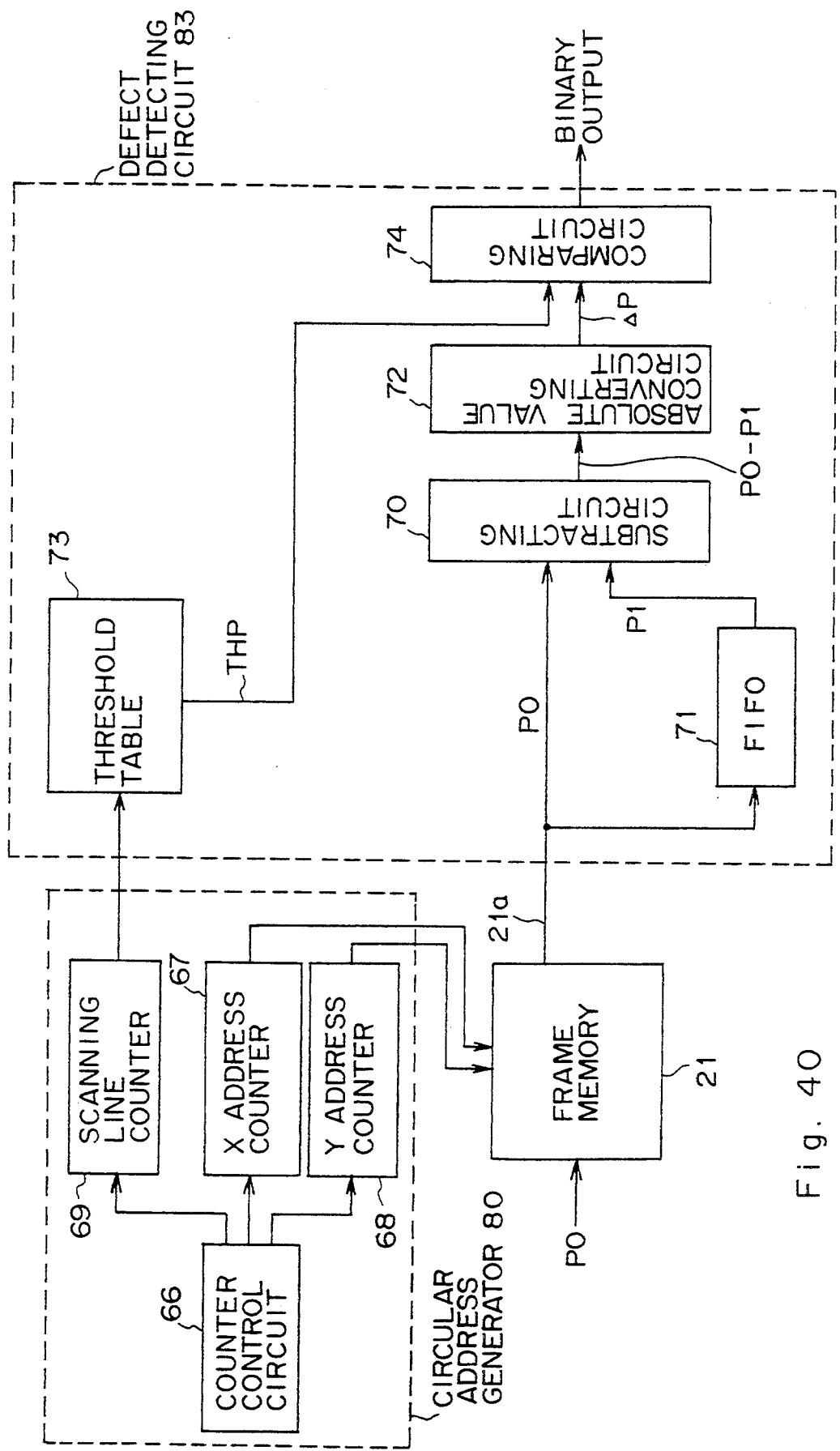
FIG. 40 shows an embodiment of the configuration of the circular address generator and the defect detecting circuit based on the circular method.

FIG. 40 is a block diagram of the configuration of the circular address generator 80 and the defect detecting circuit 84 shown in FIG. 33. The counter control circuit 66 in the circular address generator 80 controls an X address counter 67 and a Y address counter 68 in the circular address generator 80 to sequentially output from the counters 67 and 68, to the frame memory 21, X and Y addresses as circular addresses of each target picture element in the order of scanning lines L1, L2, ..., Ln shown in FIG. 36. The scanning counter 69 is provided in the circular address generator 80, and the value indicated by the counter 69 is incremented by 1 each time the test image is scanned along one circle.

In the defect detecting circuit 83, a continuous tone image signal (picture element value) 21a read according to the above described circular addresses from the frame memory 21 is sequentially inputted to a subtracting circuit 70 and a FIFO 71. The FIFO 71 delays the inputted image signal la by the number d (the above described interval of target picture elements).

Therefore, the subtracting circuit 70 receives the image signal 21a as a value P0 of the target picture element shown in FIG. 38, receives a picture element value outputted by the FIFO 71 as a value P1 of the background picture element separate from the target picture element shown in FIG. 38 by the number d (the above described interval of target picture elements), and obtains the difference between therein (P0-P1). The absolute value converting circuit 72 obtains the absolute value $(\|P0-P1\| = \Delta P)$ of the difference P0−P1.

The threshold table 73 in the defect detecting circuit 84 outputs a threshold THP according to the address outputted by the scanning line counter 69 (that is, the address for each of scanning lines L1, L2, ..., Ln). At this time, the threshold THP in a window can be set to the same value.

A comparing circuit 74 compares the above described absolute value $\Delta P$ of the difference in intensity with the threshold THP, and outputs a binary conversion signal as the determination of whether or not the target picture element indicates a defective concave, etc., according to whether or not $\Delta P > THP$ exists.

Figure 41:
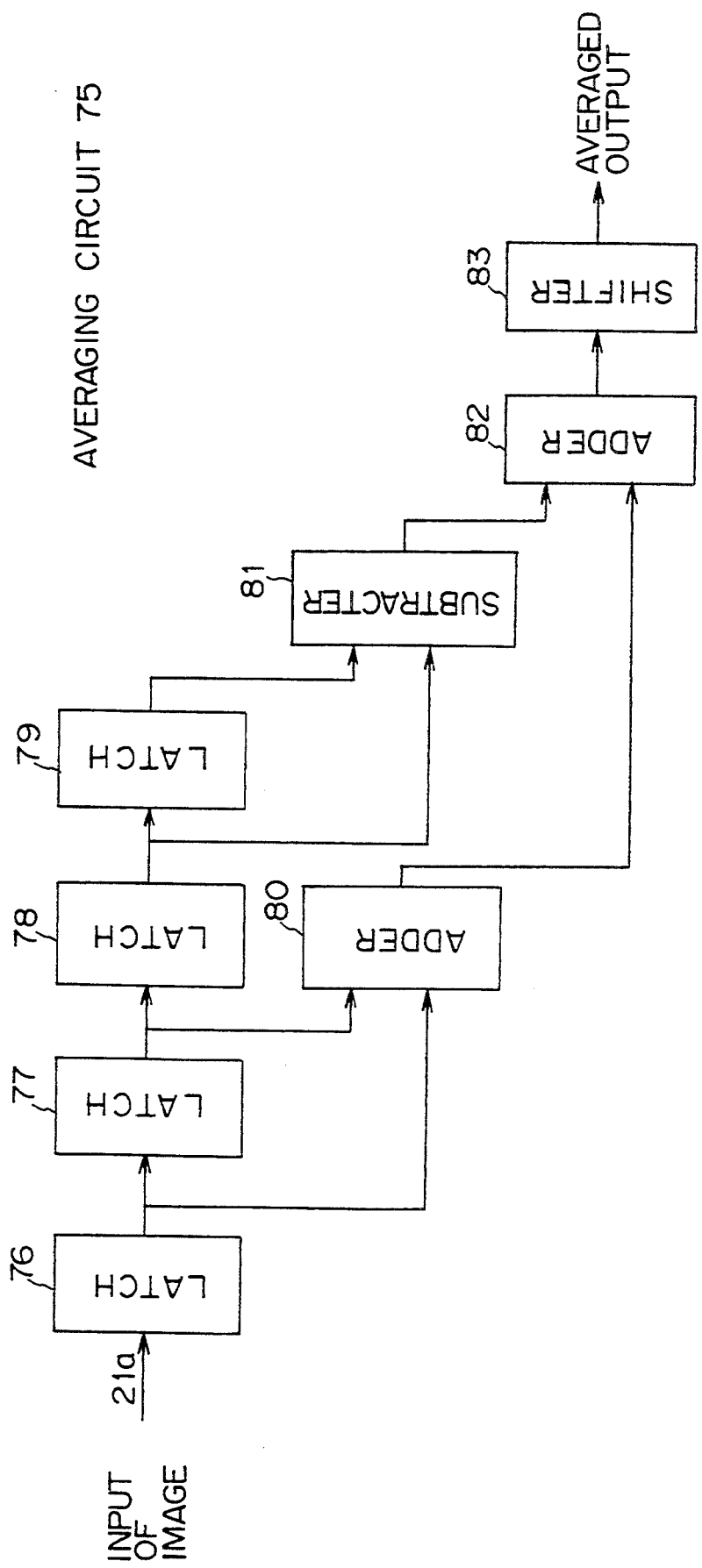
FIG. 41 shows an embodiment of the circuit for applying a moving average to the background picture element values.

FIG. 41 shows an example of the configuration of an averaging circuit 106 for applying a moving average to the picture element value P1 outputted by the FIFO 71 shown in FIG. 40. The circuit 75 is provided in series with the FIFO 71 shown in FIG. 39 (in this example, between the frame memory 1 and the FIFO 71). The averaging circuit 75 calculates the moving average of four picture elements sequentially inputted in series. While an inputted image signal (picture element value) 1a is transmitted to latches 76, 77, 78, and 79 sequentially in this circuit 75, the image data in latches 76 and 77 are added by an adder 80, and the image data in latches 78 and 79 are added by an adder 81. Then, the addition results are added by an adder 82, and thus, the sum of four picture element values is obtained. A shifter 83 calculates an averaged output by shifting the resultant sum by two bits to right (that is, the sum is divided by 4).

Figure 42:
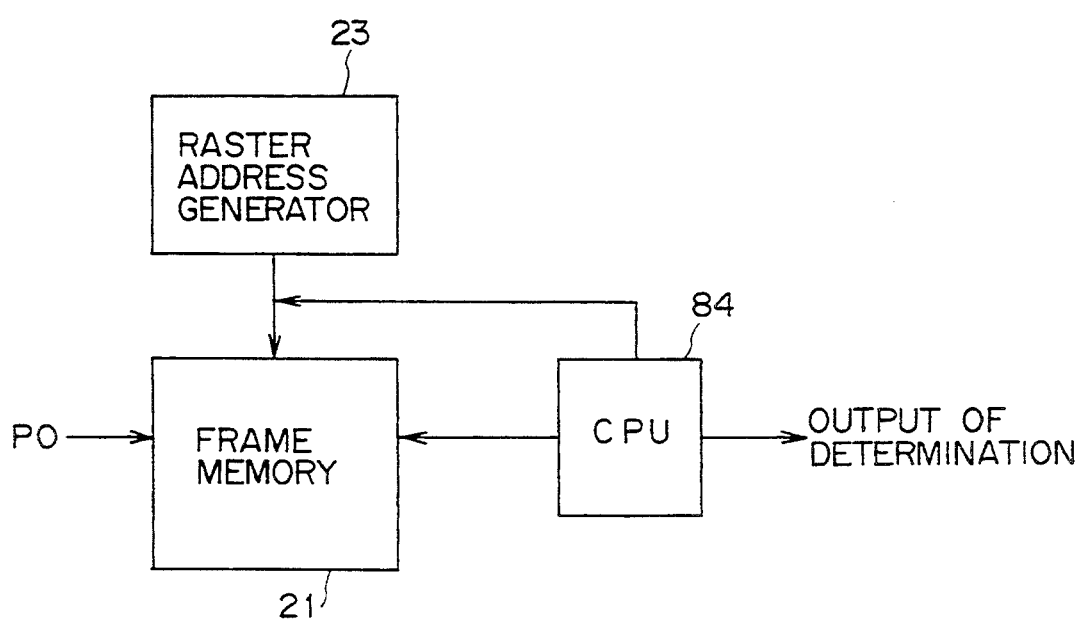
FIG. 42 is a block diagram of an embodiment of the configuration in which circular addresses is generated by software.

FIG. 42 shows an example in which a CPU 84 replaces using software the functions of the circuit excluding the frame memory 21 and the raster address generator 23F shown in FIG. 33. In this case, since the circular address generating circuits 4 and 6 operating as the hardware for accessing the frame memory 21 are not provided independently, it is supposed that the processing time of the CPU 84 is longer. Therefore, it is required that the processing time of the CPU 84 be shortened and the interval between circular scanning lines L should be appropriately extended, or the interval between target picture elements on the scanning line L should be extended.

Figure 43:
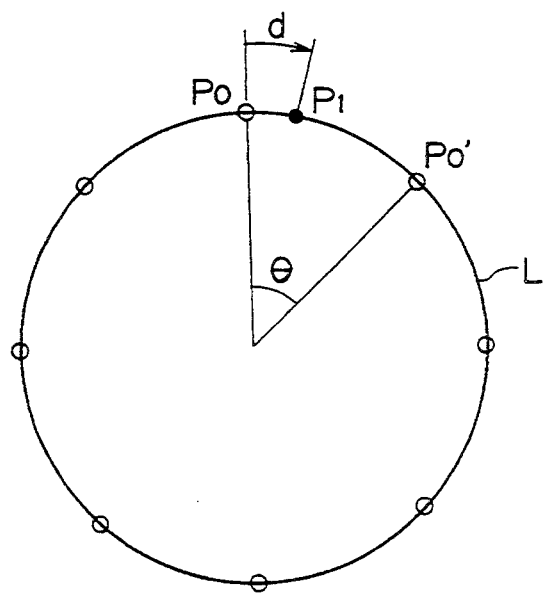
FIG. 43 is an embodiment of the process by the CPU shown FIG. 42.

FIG. 43 shows an example of shortening the processing time. First, the data of the target picture element P0 on the circular scanning line L are read. Then, the data of the background picture element P1 separated from P0 by the number d of picture elements are read. The absolute value of the intensity difference between the two picture elements is obtained ($\|P0-P1\|$). Then, the absolute value of the intensity difference is compared with the predetermined threshold THP and the target picture element P0 is converted to-the binary representation to determine whether or not the target picture element indicates a defect. If it does not indicate a defect, control is transferred to the next target picture element P0' separated from the present one by $\theta$, and the above described process is performed on it. The scanning operation completes when all circular scanning lines are processed.

The defect detection determining circuit 88 determines such that the number of picture elements indicating a defect is accumulated over one or more circular scanning lines, the number is compared with a predetermined area threshold, and then it is determined whether or not the inner surface of the test container has a defect.

The average intensity of the picture elements forming a predetermined two-dimensional local area (for example, an area of 3 picture elements×3 picture elements) centered on the background picture element P1 can replace the average intensity of a predetermined number of picture elements (a one-dimensional local area) arranged on the circular scanning line L centered on the background picture element P1 shown in FIG. 41.

Figure 44:
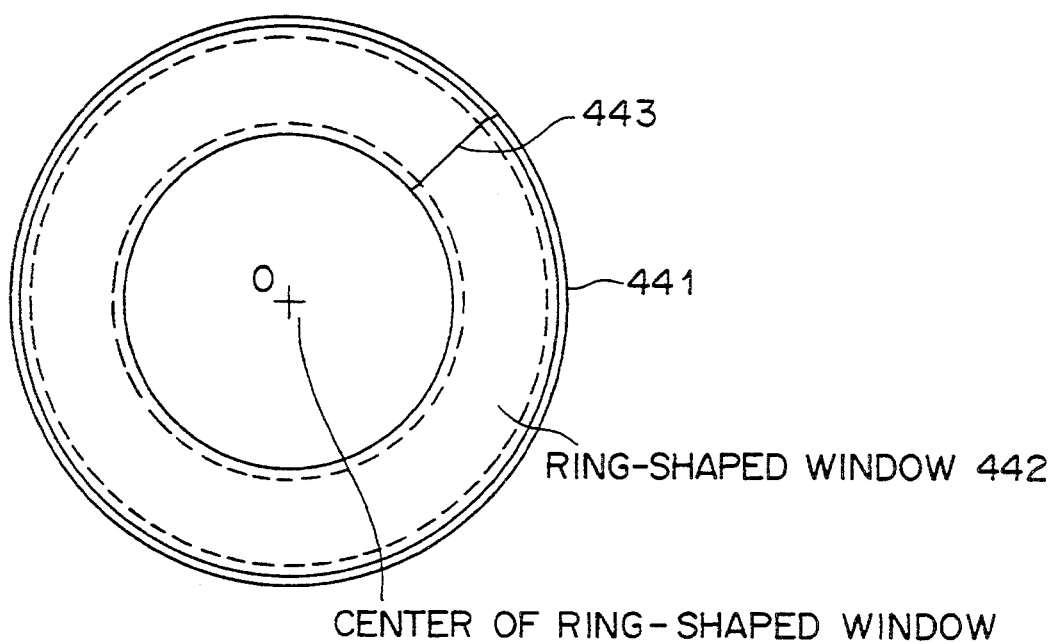
FIG. 44 indicates a ring-shaped window provided to detect the position of the joint in a cylindrical container according to the present invention.

FIG. 44 shows the image of the paper cup 441, that is, a cylindrical container, captured from above to be tested. According to the present invention, a ring-shaped window 442 is specified in a container side shown in the image. The ring-shaped window comprises two concentric circles, that is, an inner circumference shown in broken line and an outer circumference. The ring-shaped window 442 has a center O and contains the joint 443 inside. Thus, after setting the ring-shaped window 442, the area of the ring-shaped window 442 in a frame memory is specified as an area to be tested, and a multi-value continuous tone image signal in the test area is converted to a binary image signal according to a predetermined threshold. Then, the coordinate of the binary image of only the joint 443 can be obtained by scanning the binary image signal and storing the coordinate of a signal change point for each scanning line.

Figure 45:
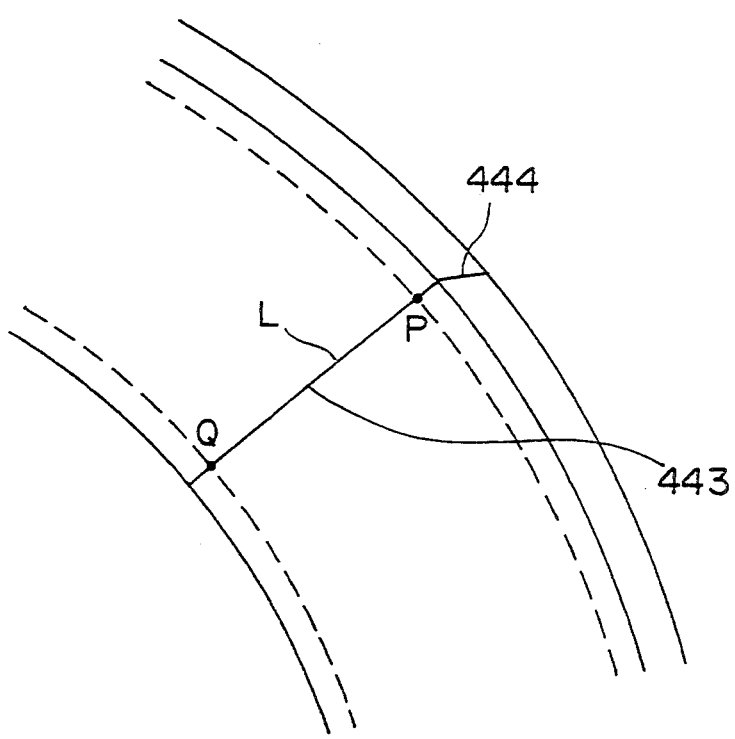
FIG. 45 indicates the intersection of the ring-shaped window the joint line of the cylindrical container.

FIG. 45 is an enlarged drawing of the joint 443. As described above, the joint 443 is approximated as a straight line L. The straight line L can be obtained by, for example, obtaining a regression line from the coordinate of each picture element forming the joint 443, and by obtaining a line KE as an approximation by calculating the distance between each picture element forming the joint 443 and the center 0 of the ring-shaped window 442, and determining the point K nearest to the point O and the point E farthest from the point O. After obtaining the equation of the line L as described above, an intersection P of the line L and the ring-shaped window 442 is obtained. FIG. 45 also shows an intersection Q of the line L and the inner circumference of the ring-shaped window 442.

Figure 46A:
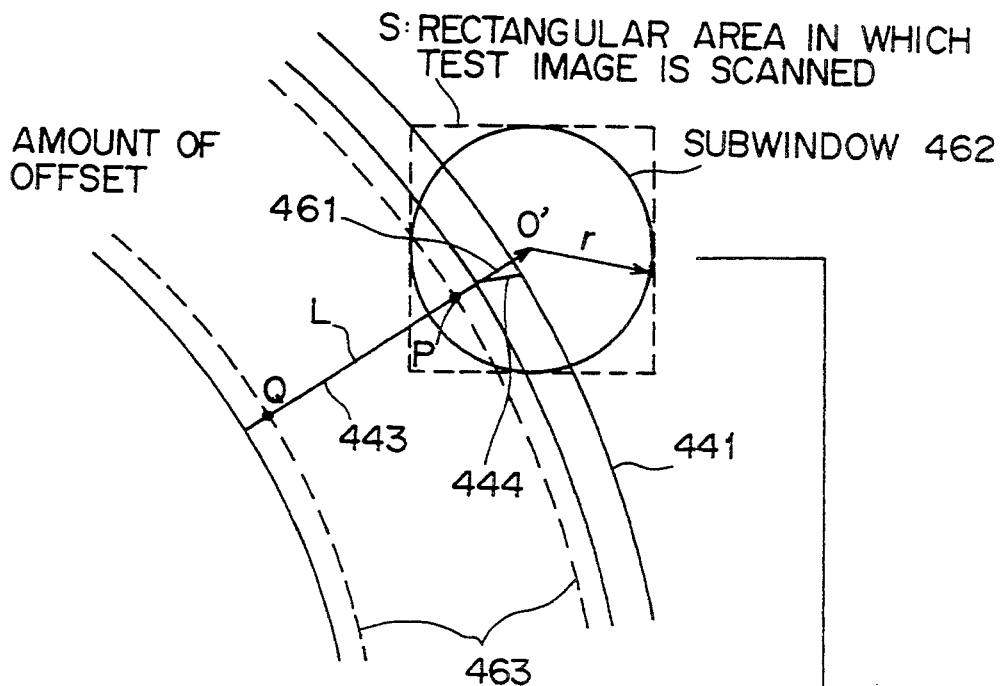
FIGS. 46A to 46C indicate a method of setting a subwindow containing the joint of the cylindrical container and a target area.

FIG. 46A shows the method of generating an area to be tested around the top-end joint 444. That is, after the above described process, a point O' is obtained by adding an offset value 461 to the coordinate of the intersection P in the direction extended from the intersection P toward the circumference as shown in FIG. 46A. Then, a subwindow 462 having the central point O' and a radius r is generated. Although the form of the subwindow is not limited to a circle, a circle is preferable because the container 441 (paper cup 441) is actually a cylindrical container, the container 441 easily rotates, and the position of the joint 443 is not fixed in the test image. Thus, the subwindow 442 is generated around the top-end joint 444 as a test area.

Figure 46B:
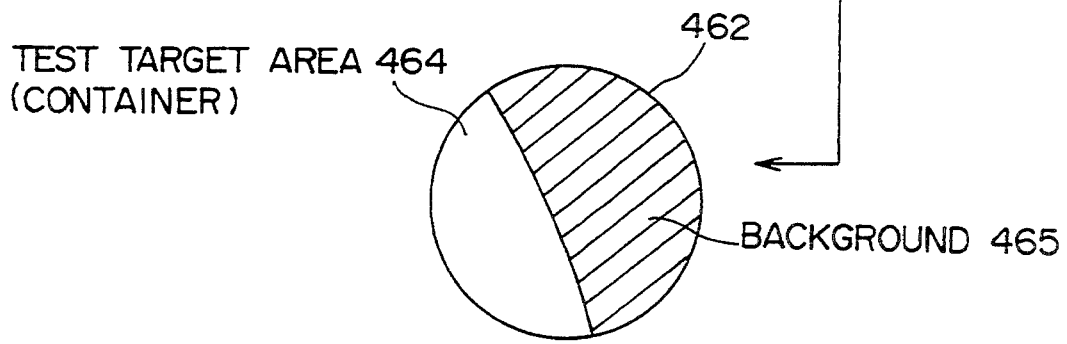

Next, FIG. 46B shows an enlarged image of the subwindow 462. First, a test target area 464 is a part of the image of the container in the subwindow 462. The position of the subwindow 462 in the image depends on the position of the joint 443 movable according to the rotation of each container. Accordingly, the form of the target area 464 in the subwindow 462 is not fixed, but varies with the rotation of each container. A background 465 is distinguished from the target area 464 by showing it in black without luster so that it cannot be taken for a picture element indicating a black spot. This can be easily realized because the image of the inner surface of the container 441 can be illuminated brightly compared with the image indicating the area outside the container 441, that is, the background 465. Then, the subwindow 462 is scanned and the test target area 464 is segmented according to an appropriate threshold TH1, thereby setting a scanning line 466 associated with only the inside of the test target area 464.

Figure 46C:
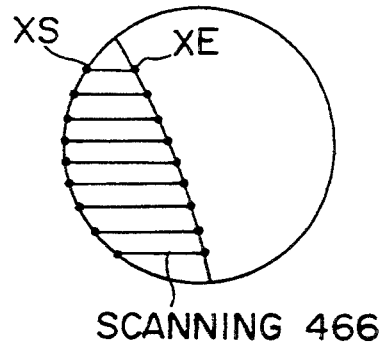

When a picture element indicating a black spot is to be detected, a binary signal start point XS and a binary signal end point XE are obtained for each scanning line 466. Then, the area between the start point XS and the end point XE is specified as a test target area for each scanning line. Thus, the test target area in the subwindow 462 can be limited to the area 464 as shown in FIGS. 46B and 46C.

Furthermore, as another method of determining the test target area 464 in the subwindow 462, a background-excluded binary image is stored in a memory for storing data of a test target area. In this case, the frame memory is scanned again and an AND operation is performed for each picture element corresponding to a binary image in the memory for storing data of a target area in the subwindow 462 when a picture element indicating a black spot is to be detected.

Figure 47:
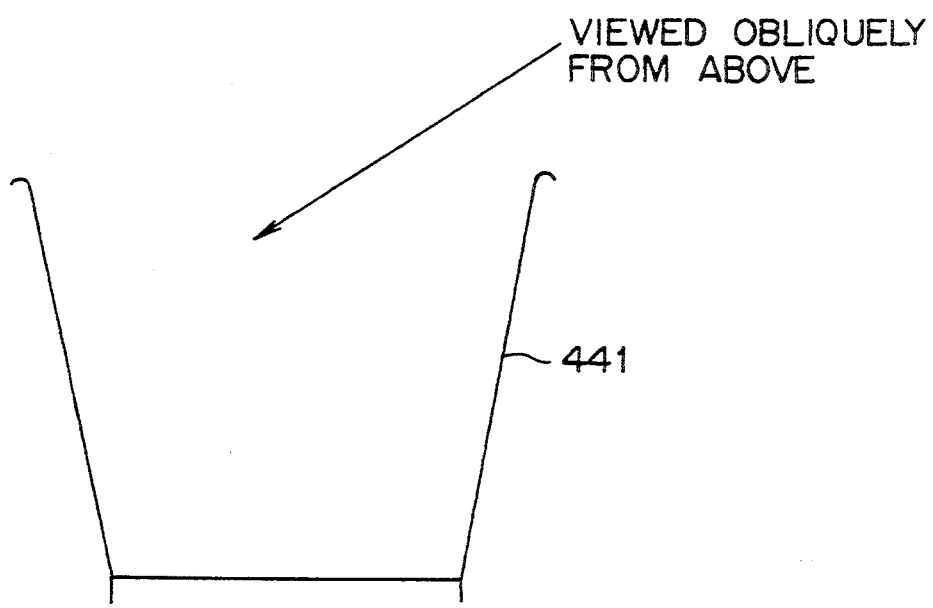
FIG. 47 shows another example of the capture direction a cylindrical container.

FIG. 47 shows the case where the inner side of the container 441 is captured obliquely from above. If the inner side is captured obliquely, more screens are required to test over the inner side completely, but with higher resolvability than in the case where it is captured right from above. FIGS. 48, 49, 50A, 50B and 50C showing the image obtained when the container is captured obliquely from above correspond to FIGS. 44, 45, 46A, 46B and 46C respectively.

Figure 48:
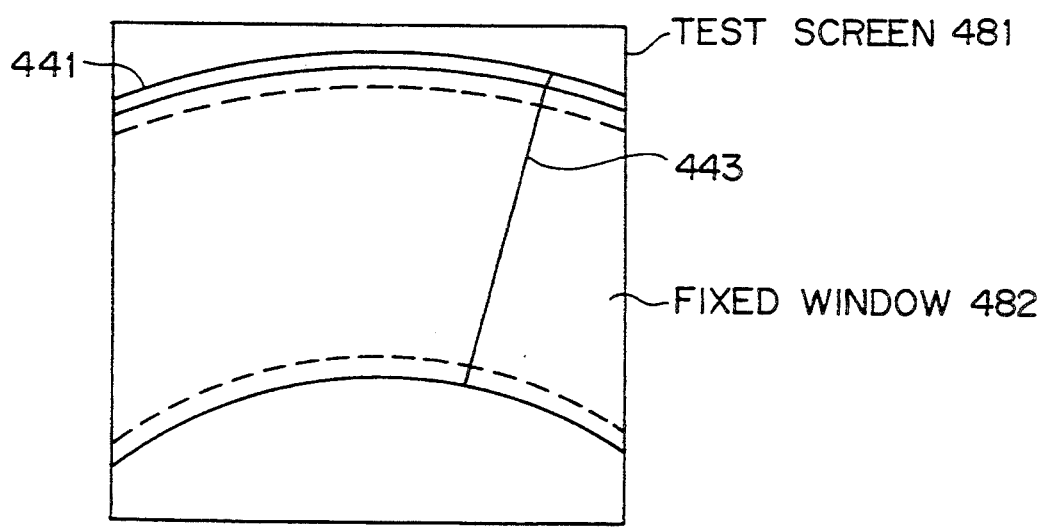
FIG. 48 indicates a fixed window provided to detect the position of a joint for an image captured in the direction described above.

In FIG. 48, a fixed window 482 is provided in a test screen 481 (a screen of a display unit such as a CRT, etc.). The test method is almost the same as the case where the container 441 is captured right from above except the capture direction and the window form.

Thus, according to the present invention, a black spot is detected around the top-end joint 444 in the container 441 by specifying the subwindow 462 of a predetermined form having a predetermined center point O' in the extension of the joint line L after the position of the linear joint 443 in a cylindrical container has been detected. As a result, a spot can be efficiently detected around the joint with high precision at a high speed.

Figure 51:
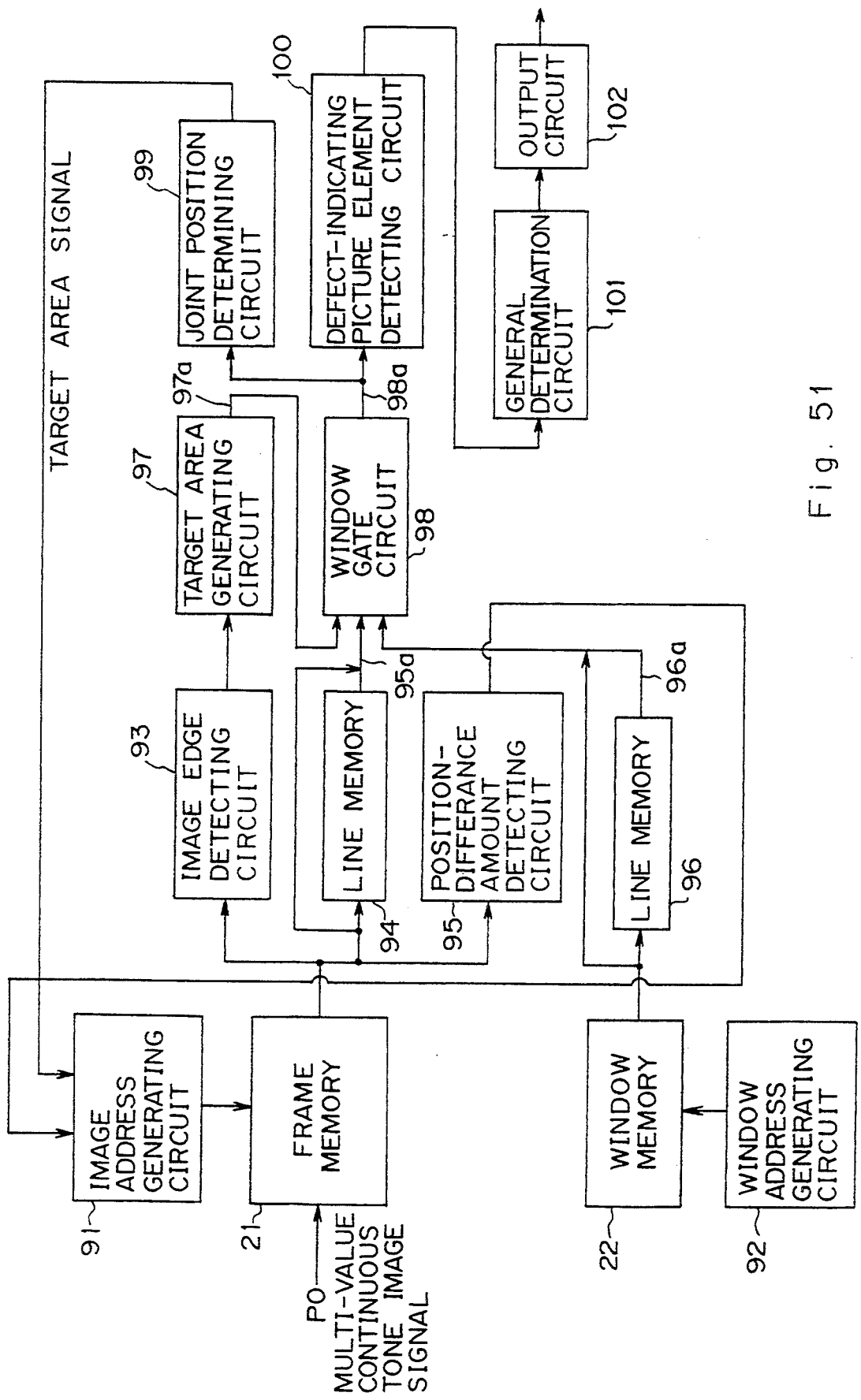
FIG. 51 is a block diagram of the hardware configuration of the cylindrical container inner surface tester according to an embodiment of the present invention.

FIG. 51 is the block diagram of the hardware of the cylindrical container inner surface tester according to the first embodiment of the present invention. According to the explanation below, FIGS. 6, 44 through 46 are also referred to.

In FIG. 51, a frame memory 21 stores a multi-value continuous tone image P0 obtained by capturing the cylindrical container 441 (a paper cup 441 shown in FIG. 6) to be tested from above. An image address generating circuit 91 provides for the above described frame memory 21 an address at which a multi-value continuous tone image P0 is stored. A window memory 22 stores as a graphic pattern the ring-shaped window 442 and the subwindow 442 where the position of the joint 443 of the cylindrical container 441 is detected. A window address generating circuit 92 generates an address at which the above described graphic pattern is generated for the window memory 22.

An image edge detecting circuit 93 detects a circuit for detecting a test target area 464 in the subwindow 462, and the image edge detecting circuit 93 is provided with a binary conversion circuit for segmenting the background 465 and the container (test target area) 464 in the subwindow 462, and stores the coordinate of a change point of a binary signal. A line memory 94 delays a multi-value continuous tone image signal inputted from the frame memory 21 by one horizontal scanning process. A position difference amount detecting circuit 95 detects the difference of the capture position of the cylindrical container 441 in the frame memory 21. Another line memory 96 delays an image mask signal inputted from the window memory 22 by one horizontal scanning process.

Each of output signals 94a and 96a from the line memory 94 and 96 are outputted to a window gate circuit 98, and a multi-value continuous tone image signal is ANDed with an image mask signal and selected for each picture element.

A target area generating circuit 97 generates coordinate data from a binary conversion start point XS to a binary conversion end point XE of an image edge detected by the image edge detecting circuit 93. A target area signal 97a is outputted to the window gate circuit 98.

An output 98a of the window gate circuit 98 is provided for a joint position determining circuit 99 or a defect-indicating picture element detecting circuit 100. The defect-indicating picture element detecting circuit 100 detects a picture element indicating a black spot by a method of detecting, for example, the valley of a signal change as a defective portion converted to a binary representation. A general determination circuit 101 obtains the number of picture elements indicating a black spot and obtains the area of a black spot. If the area is larger than a predetermined area threshold, the circuit determines that the tested container 441 is defective. A signal indicating whether or not a container finally determined by the general determination circuit 101 is acceptable is outputted externally through the output circuit 102.

Next, an operation of the above described embodiment is explained in order.

First, a multi-value continuous tone image signal P0, that is, the capture data of the container 441, is stored in the frame memory 21 as a test image. The first scanning operation is performed for the frame memory 21 so as to detect the position difference of the container 441.

Namely, the image address generating circuit 91 generates an address of all or a part of a rectangular area for a multi-value continuous tone image signal P0 stored in the frame memory 21. At this time, the multi-value continuous tone image signal outputted from the frame memory 21 is applied to the position difference amount detecting circuit 95, and the position difference of the container 441 is detected in the test image. The position of a cylindrical container can be detected using a middle point between the first rise point where the outline of the outer circle of a cylindrical container appears and the last fall point in a scanning line of a binary image.

Next, in detecting the position of the above described joint 443, the amount of a position difference of the container 441 outputted by the position difference amount detecting circuit 95 is applied to the image address generating circuit 91. Then, the second scanning operation is performed for the frame memory 21. During the second scan over a -test image, the position of the container 441 is corrected according to the amount of a position difference. After the correction, a multi-value continuous tone image signal skips the line memory 94 and is directly applied to the window gate circuit 98. Simultaneously, the pattern data of the ring-shaped window 442 stored in the window memory 22 are sequentially read synchronously with the scanning operation over a test image in picture element units, and the read pattern data are applied to the window gate circuit 98 with another line memory 96 bypassed. The window gate circuit 98 ANDs the above described two input signals, generates a multi-value continuous tone image signal in the ring-shaped window 442 shown in FIG. 44 and containing only the joint 443, and outputs the result to the joint position determining circuit 99.

The joint position determining circuit 99 converts to a binary an inputted multi-value continuous tone image signal, detects the coordinate of each picture element in the binary representation, determines the regression line L of each picture element, and calculates the coordinate of the intersection P of the line L and the outer circumference of the ring-shaped window. Then, it calculates the generation reference coordinate of the subwindow 462 (the coordinate of the center O' of the subwindow 462 in the present example) by adding a predetermined offset value to the coordinate of the intersection P, and determines the rectangular area S circumscribing the subwindow 462 (FIG. 46) for use in a test image scanning for the subwindow 462 generated according to the reference coordinate. Then, it outputs the area data indicating the rectangular area S to the image address generating circuit 91.

Next, the third scanning operation is performed for the frame memory 21. During the scanning operation, the area around the top-end joint 444 is scanned by scanning the frame memory 21 in the above described rectangular area S, and the resultant multi-value continuous tone image signal is applied to the image edge detecting circuit 93 and the line memory 94. Synchronously, the pattern data of the subwindow 462 are read from the window memory 22, and the read pattern data are applied to the line memory 96. The line memories 94 and 96 delay an inputted signal by one horizontal scanning line according to an FIFO method, and an arithmetic operation is performed by the image edge detecting circuit 93 and the target area generating circuit 97 during the delay period to determine the test image area in the subwindow 462. That is, the image edge detecting circuit 93 converts an inputted multi-value continuous tone image signal to a binary value, and detects a signal start point coordinate XS and a signal end point coordinate XE in one scanning line in the binary signal. During the detecting process, a test image and a signal from the subwindow 462 are temporarily stored in the line memories 94 and 96 respectively. Then, at the scanning operation after detecting the coordinate points XS and XE by the image edge detecting circuit 93, the target area generating circuit 97 generates an image gate signal between the coordinate points of the binary signal start point XS and the binary signal end point XE, and applies it to the window gate circuit 98. Simultaneously, the outputs from the line memories 94 and 96 are applied to the window gate circuit 98. The window gate circuit 98 outputs to the defect-indicating picture element detecting circuit 100 a multi-value continuous tone image signal, obtained by ANDing these three signals, in the subwindow 462 containing only the top-end joint 444. According to the signal, the defect-indicating picture element detecting circuit 100 then detects a picture element indicating a defect in the subwindow 462 area.

Thus, in the above described embodiment, a target area is detected (between the coordinate points XS and XE) in each scanning operation by the target area generating circuit 97 in a series of 3 scanning operations performed for the frame memory 21; a multi-value continuous tone image signal in the area is sequentially outputted in each scanning process; and only a multi-value continuous tone image signal in the test target area 464 except the background 465 in the subwindow 462 is outputted to the defect-indicating picture element detecting circuit 100.

Figure 52:
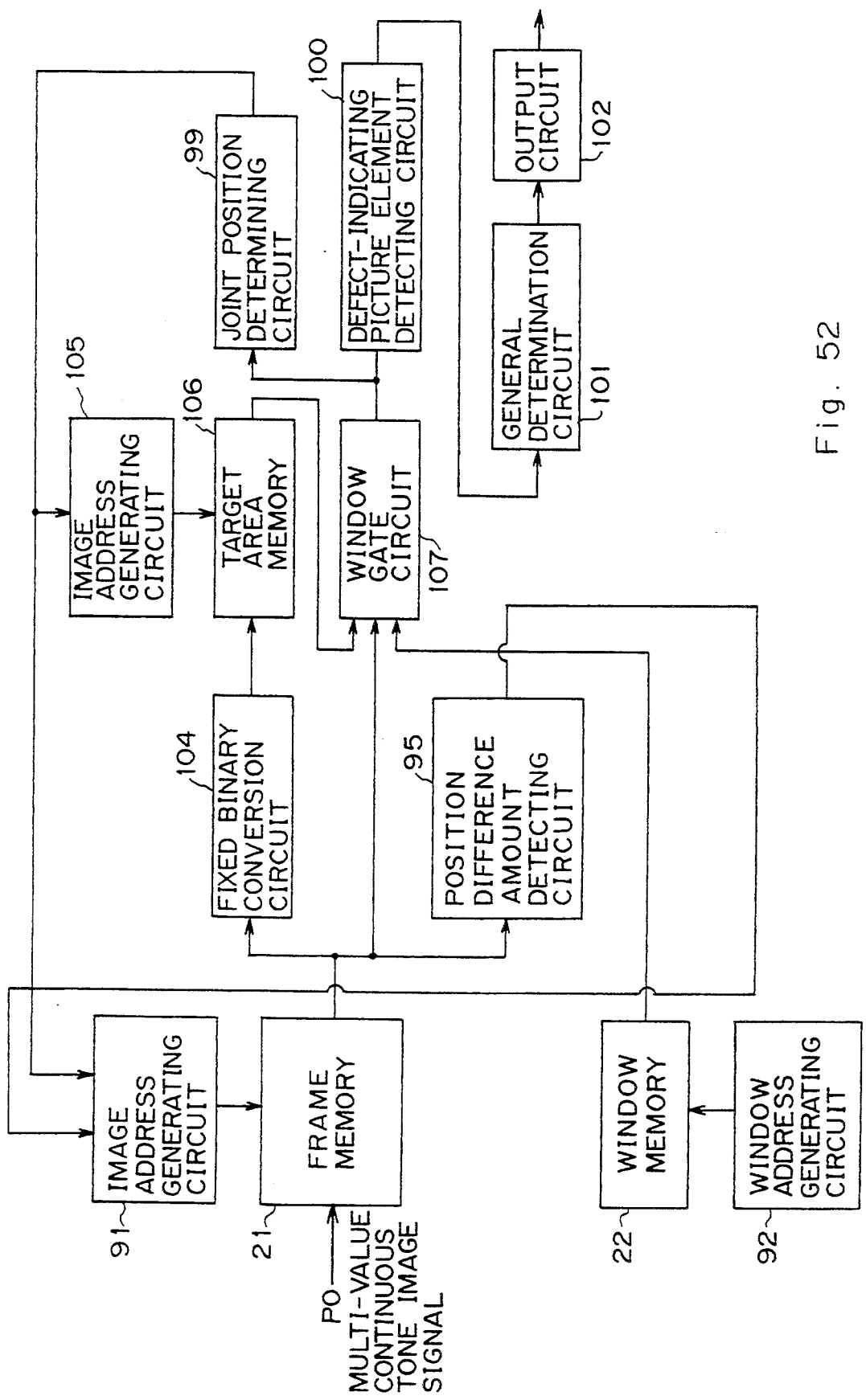
FIG. 52 is a block diagram of the hardware configuration of the cylindrical container inner surface tester according to the embodiment of the present invention.

FIG. 52 is the block diagram showing the configuration of the hardware of the cylindrical container inner surface tester according to the other embodiment of the present invention. A binary conversion circuit 104 converts to a binary value a multi-value continuous tone image signal read from the area corresponding to the rectangular area S of the frame memory 21. A target area memory 106 stores a binary image of the container 441 except the background 465. An image address generating circuit 105 provides an address of a binary image to be stored in the target area memory 106. A window gate circuit 107 has a similar function as the window gate circuit 98 shown in FIG. 51. Other portions assigned the same number in the configuration as that shown in FIG. 51 has also the same function.

According to the second embodiment, the pattern data in the target area 464 of the container 441 with the area corresponding to the background 465 excluded from the rectangular area S are temporarily stored in the target area memory 106 in the third scanning operation performed for the frame memory 21. Then, in the fourth scanning operation, an area corresponding to the rectangular area S in the frame memory 21 is scanned again. At this time, a multi-value continuous tone image signal, an area signal of pattern data read from the target area memory 106, and an area signal of the subwindow 462 read from the window memory 22 are applied to the window gate circuit 107. The window gate circuit 107 ANDs these three signals, and outputs only the multi-value continuous tone image signal of the target area 464 in the subwindow 462 to the defect-indicating picture element detecting circuit 100.

Figure 49:
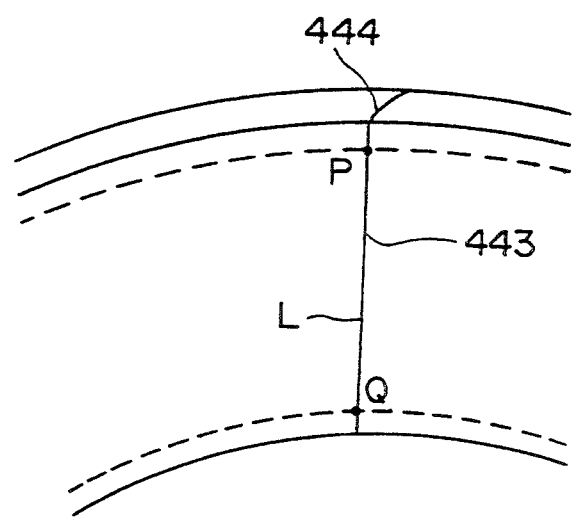
FIG. 49 indicates an intersection of the joint line of the above described image and the ring-shaped window.
Figure 50A:
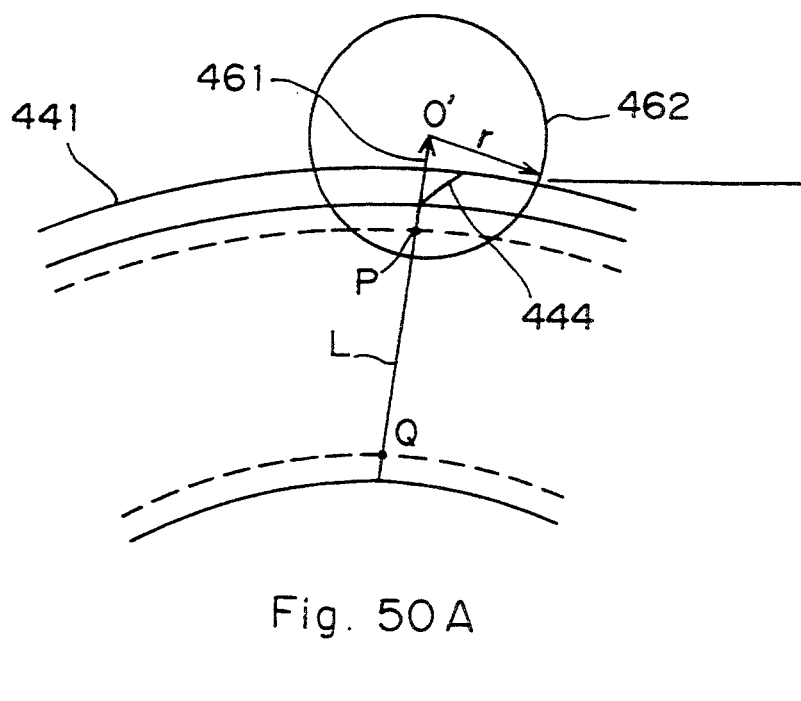
FIGS. 50A to 50C indicate a method of setting a subwindow in the above described fixed window and a target area.
Figure 50B:
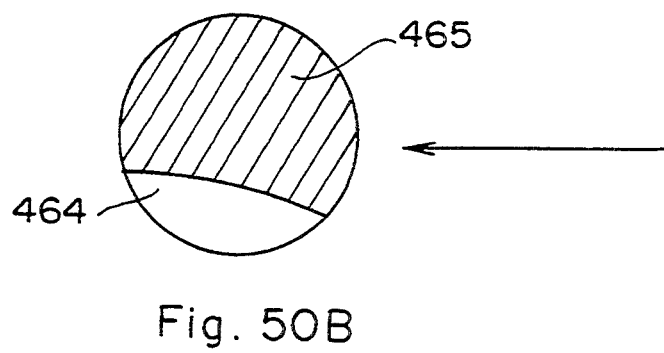
Figure 50C:
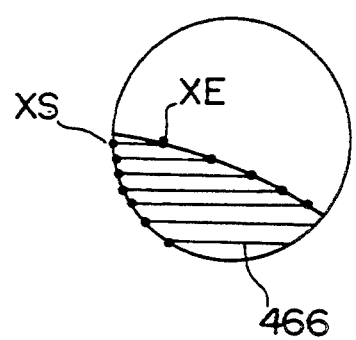

Next, the other embodiment in the present invention is explained below. In this embodiment, the upper part of the inner surface of the container 441 is captured obliquely from a predetermined point above as shown in FIG. 49. In this case, the container is captured in a plurality of directions (three directions, for example) making an equal angle to each other round the center of the container. As a result, the joint 443 is necessarily included in the test screen 481. The test screen shown in FIG. 48 is one of the screens captured by a plurality of capturing devices.

In this case, an image of the container 441 is captured as a part of an oval image. Therefore, an oval-shaped window (fixed window) 412 is required in place of the ring-shaped window 442 shown in FIG. 44. Since the form of the container 441 and the capture directions are fixed, the fixed window 482 can be easily generated. Furthermore, the difference of the position of the container 441 is detected to generate the fixed window 482 such that a middle point between the first rise point where the outer circumference of the container 441 appears and the last fall point in a horizontal scanning line of a binary image as in the previous embodiment is obtained. The processes after the position of the joint 443 has been detected are the same as those in the previous embodiments.

Therefore, in the present embodiment, since only the ring-shaped window 442 has to be replaced with the fixed window 482 in the window memory 22, the hardware configuration shown in FIGS. 51 and 52 can be used as is.

What is claimed is:

1. A cylindrical container inner surface tester for illuminating from above an opening of a test container located at a predetermined position with the opening set levelly, for capturing said opening through a TV camera, and for detecting black and white spots on the inner surface of said cylindrical container by analyzing using defect detecting means an image obtained by said TV camera, said tester comprising:

a frame memory for storing as image data a multi-value continuous tone image signal A/D-converted from a continuous tone image signal obtained by scanning said captured image, and an area detecting unit for generating a binary image signal by binary-converting, using a predetermined threshold (THG), a multi-value continuous tone image signal read by horizontally or vertically scanning the frame memory and for determining as a test area an area between a first rise point and a last fall point of each scanning line of said binary image signal.

2. The cylindrical container inner surface tester according to claim 1 further comprising:

masking means for masking, with predetermined mask pattern data an area having a different optical characteristic in the test area detected by said area detecting unit.

3. A cylindrical container inner surface tester for illuminating from above an opening of a test container located at a predetermined position with said opening set levelly, for capturing said opening through a TV camera, and for detecting black and white spots on the inner surface of said cylindrical container by analyzing, using defect detecting means, an image obtained by said TV camera, said tester comprising:

determining means for determining a defect when the image of the inner surface of said cylindrical container is scanned along a ring or spiral scanning line (hereinafter referred to as a circular scanning line) which is centered on a central portion of the image and varies sequentially per cycle of a radius varying every one or more picture elements predetermined, and then the absolute value indicating a difference between the intensity of the target picture elements among a plurality of picture elements arranged at intervals such that one or more picture elements are arranged between two target picture elements and the intensity of background picture element in a predetermined number of a plurality of picture elements forward or backward of a target picture element is compared with a threshold, predetermined according to a position of the circular scanning line, and such processes are repeated for each target picture element, and said determining means determines a defective container inner surface when an absolute value is larger than a difference value detected between said intensity values.

4. The cylindrical container inner surface tester according to claim 3, wherein said threshold is set every occasion of the circular scanning line.

5. The cylindrical container inner surface tester according to claim 3 or 4, wherein the intensity of said background picture element equals an average intensity of the picture elements in a predetermined one-dimensional or two-dimensional local area centered on said background picture element.

6. A cylindrical container inner surface tester for determining a spot on an inner surface of a side of an axis-symmetrical cylindrical container of a predetermined form having a linear joint in said side surface, by illuminating the inside of said cylindrical container from above, capturing an image, through a TV camera, of the illuminated surface of said cylindrical container from above in an axis direction of said cylindrical container, and analyzing the captured image, said tester comprising:

a frame memory for storing a multi-value continuous tone image signal obtained by A/D-converting a continuous tone image signal obtained by scanning said captured image;

area specifying means for generating a ring-shaped window pattern such that an image of said linear joint in the side of said container is included in said pattern;

change point storage means for converting to a binary value according to a predetermined threshold a multi-value continuous tone image signal read by a horizontal or vertical scanning operation from an area specified by a ring-shaped window pattern generated by said area specifying means, and for storing for each scanning operation of a signal change point coordinate of a binary image signal generated by said converting process;

position determining means for determining a position of a line similar to said joint in the side surface of said container according to a signal change point coordinate stored in said change point storing means;

intersection calculating means for calculating an intersection coordinate between a line determined by said position determining means and said ring-shaped window pattern;

reference coordinate determining means for determining a generation reference coordinate of a subwindow by adding a predetermined offset value to said intersection coordinate obtained by said intersection calculating means; and target area extracting means for generating a subwindow of a predetermined form according to the generation reference coordinate of a subwindow determined by said reference coordinate determining means, and for determining, as a test target area to be searched for a spot, an image area in said frame memory corresponding to the area of said subwindow.

7. The cylindrical container inner surface tester according to claim 6, further comprising:

binary image signal generating means for generating a binary image signal by converting to a binary value a multi-value continuous tone image signal in said sub-window according to a predetermined threshold for use in detecting a background of said cylindrical container, wherein said target area extracting means determines as a test target area, to be searched for a spot, an image area, in said frame memory, corresponding to an area obtained by excluding the background of said cylindrical container from said subwindow area.

8. A cylindrical container inner surface tester for determining a spot on an inner surface of a side of an axis-symmetrical cylindrical container of a predetermined form having a linear joint in its side surface, by illuminating the inner surface of said cylindrical container from above, capturing an image through a TV camera, of the illuminated surface of said cylindrical container from above oblique to an axis direction of said cylindrical container, and analyzing the captured image, said tester comprising:

a frame memory for storing a multi-value continuous tone image signal obtained by A/D-converting a continuous tone image signal obtained by scanning said captured image;

area specifying means for generating a fixed window pattern such that an image of said linear joint in the side of said container is included in said pattern;

change point storage means for converting to a binary value according to a predetermined threshold a multi-value continuous tone image signal read by a horizontal or vertical scanning operation from an area specified by a fixed window pattern, generated by said area specifying means, and for storing for each scanning operation a signal change point coordinate of a binary image signal generated by said converting process;

position determining means for determining a line position similar to said joint in the side surface of said container according to the signal change point coordinate stored in said change point storing means;

intersection calculating means for calculating an intersection coordinate between a line determined by said position determining means and said window pattern;

reference coordinate determining means for determining a generation reference coordinate for a subwindow by adding a predetermined offset value to said intersection coordinate obtained by said intersection calculating means;

target area extracting means for generating a subwindow of a predetermined form according to the generation reference coordinate of a subwindow determined by said reference coordinate determining means, and for determining as a test target area, to be searched for a spot, an image area, in said frame memory, corresponding to the area of said subwindow.

9. The cylindrical container inner surface tester according to claim 8, further comprising:

binary image signal generating means for generating a binary image signal by converting to a binary value a multi-value continuous tone image signal in said sub-window according to a predetermined threshold for use in detecting an background of said cylindrical container, wherein said target area extracting means determines as a test target area, to be searched for a spot, an image area, in said frame memory, corresponding to an area obtained by excluding the background of said cylindrical container from said subwindow area.

* * * * *

UNITED STATES PATENT AND TRADEMARK OFFICE
CERTIFICATE OF CORRECTION

PATENT NO. : 5,412,203
DATED : May 2, 1995
INVENTOR(S) : Toyama

It is certified that error appears in the above-indentified patent and that said Letters Patent is hereby corrected as shown below:

Column 5, line 54, delete "POD(i,j)=i" and insert --POD(i,j)=1--.

Column 12, line 61, delete "(PO(i+a),j)," and insert --(PO(i+α),j),--.

Column 15, line 19, delete "PO(i-α,j)" and insert --(PO(i+α,j)--.

Column 15, line 42, delete "|PO-P1Δ|" and insert --||PO-P1||--.

Column 17, line 47, delete "Generated" and insert --generated--.

Column 17, line 54, delete "b-" and insert --b=--.

Column 19, line 55, delete "SSA" and insert --S5A--.

UNITED STATES PATENT AND TRADEMARK OFFICE
CERTIFICATE OF CORRECTION

PATENT NO. : 5,412,203
DATED : May 2, 1995
INVENTOR(S) : Toyama

It is certified that error appears in the above-indentified patent and that said Letters Patent is hereby corrected as shown below:

Column 21, line 41, delete "binary." and insert --binary--.

Column 22, line 24, delete "opening." and insert --opening--.

Column 22, line 44, delete "$\alpha$" and insert --$\beta$--.

Column 24, line 11, delete "-the" and insert --the--.

Column 25, line 62, delete "PO(i+,j)" and insert --PO(i+$\alpha$,j)--.

Column 25, line 63, delete "PO(i-,j)" insert --PO(i-$\alpha$,j)--.

Column 25, line 66, delete "{k=o$\Sigma^{n-1}$" and insert --$\{\sum_{k=o}^{n-1}$--.

Column 25, line 68, delete "{k=o$\Sigma^{n-1}$" and insert --$\{\sum_{k=o}^{n-1}$--.

Column 26, line 7, delete "61-2 2" and insert --61-2--.

UNITED STATES PATENT AND TRADEMARK OFFICE
CERTIFICATE OF CORRECTION

PATENT NO. : 5,412,203
DATED : May 2, 1995
INVENTOR(S) : Toyama

Page 3 of 4

It is certified that error appears in the above-indentified patent and that said Letters Patent is hereby corrected as shown below:

Column 27, line 35, delete "ZG" and insert --Zc--.

Column 27, line 62, delete "a" and insert --$\alpha$--.

Column 27, line 64, delete "-the" and insert --the--.

Column 28, line 5, delete "a" and insert --DC--.

Column 33, line 9, delete "$\Delta$IP" and insert --$\Delta$P--.

Column 33, line 61, delete "therein" and insert --them--.

Column 34, line 47, delete "||P0-P1 and insert --||P0-PI||--.

Column 34, line 50, delete "-the" and insert --the--.

Column 37, line 59, delete "-test" and insert --test--.

UNITED STATES PATENT AND TRADEMARK OFFICE
CERTIFICATE OF CORRECTION

PATENT NO.   : 5,412,203
DATED        : May 2, 1995
INVENTOR(S)  : Toyama

It is certified that error appears in the above-indentified patent and that said Letters Patent is hereby corrected as shown below:

Column 40, line 25, after "data" insert a --,--.

Signed and Sealed this

Twelfth Day of December, 1995

Attest:

BRUCE LEHMAN

Attesting Officer

Commissioner of Patents and Trademarks